US009080178B2

(12) United States Patent
Palsson et al.

(10) Patent No.: US 9,080,178 B2
(45) Date of Patent: Jul. 14, 2015

(54) *ESCHERICHIA COLI* METABOLIC ENGINEERING OXYGEN INDEPENDENT PLATFORM STRAINS AND METHODS OF USE THEREOF

(75) Inventors: Bernhard Palsson, San Diego, CA (US); Vasiliy A. Portnoy, San Diego, CA (US)

(73) Assignee: The Regents Of The University Of California, Oakland, CA (US)

( * ) Notice: Subject to any disclaimer, the term of this patent is extended or adjusted under 35 U.S.C. 154(b) by 139 days.

(21) Appl. No.: 13/166,560

(22) Filed: Jun. 22, 2011

(65) Prior Publication Data

US 2012/0064581 A1   Mar. 15, 2012

Related U.S. Application Data

(60) Provisional application No. 61/363,863, filed on Jul. 13, 2010.

(51) Int. Cl.
| | |
|---|---|
| C12P 7/18 | (2006.01) |
| C12P 13/04 | (2006.01) |
| C12N 15/70 | (2006.01) |
| C12P 7/56 | (2006.01) |
| C12N 9/02 | (2006.01) |

(52) U.S. Cl.
CPC .............. *C12N 15/70* (2013.01); *C12N 9/0053* (2013.01); *C12P 7/18* (2013.01); *C12P 7/56* (2013.01); *C12P 13/04* (2013.01)

(58) Field of Classification Search
CPC ........ C12N 9/0053; C12N 15/70; C12P 7/56; C12P 7/18; C12P 13/04
USPC .............................. 435/252.33, 440; 536/23.2
See application file for complete search history.

(56) References Cited

PUBLICATIONS

Portnoy et al., Applied and Environmental Microbiology 74(24):7561-7569, 2008.*
Bunch et al., Microbiology 143(1):187-195, 1997.*
Winstedt et al. (2000) "Terminal Oxidases of *Bacillus subtilis* Strain 168: One Quinol Oxidase, Cytochrome $aa_3$ or Cytochrome $bd$, Is Required for Aerobic Growth," J. Bacteriol., 182(23):6557-6564.
Yun et al. (1990) "Cloning and DNA sequencing of the *fbc* operon encoding the cytochrome bc1 complex from *Rhodobacter sphaeroides*," 194(2): 399-411.
Zamboni et al. (2003) "Knockout of the high-coupling cytochrome $aa_3$ oxidase reduces TCA cycle fluxes in *Bacillus subtilis*," FEMS Microbiology Letter 226: 121-126.
Dubrac et al. (2000) "Fur Positive Regulation of Iron Superoxide Dismutase in *Escherichia coli*: Functional Analysis of the sodB Promoter," J Bacteriol. Jul. 2000; 182(13): 3802-3808.
Adams and Jia, "Structural and Biochemical Evidence for an Enzymatic Quinone Redox Cycle in *Escherichia coli*: Identification of a Novel Quinol Monooxygenase." *J of Biological Chemistry*, 280(9):8358-8363 (2005).

Alexeeva, et al., "Requirement of arcA for Redox Regulation in *Escherichia coli* under Microaerobic but Not Anaerobic or Aerobic Conditions." *J Bacteriol*, 185(1):204-209 (2003).
Barrett, et al., "NCBI GEO: Archive for High-Throughput Functional Genomic Data." *Nucleic Acids Res*, 37(Database issue):D885-890 (2009).
Becker, et al., "Quantitative Prediction of Cellular Metabolism with Constraint-Based Models: The Cobra Toolbox." *Nat. Protocols*, 2(3):727-738 (2007).
Bekker, et al., "Changes in the Redox State and Composition of the Quinone Pool of *Escherichia coli* During Aerobic Batch-Culture Growth." *Microbiology*, 153(Pt 6):1974-1980 (2007).
Bekker, et al., "The ArcBA Two-Component System of *Escherichia coli* Is Regulated by the Redox State of Both the Ubiquinone and the Menaquinone Pool." *J Bacteriol*, 192(3):746-754 (2010).
Bell and Bernhar, "Phenotype phase plane analysis using interior point methods." *Computers & Chemical Engineering*, 29(3):481-486 (2005).
Brondsted and Atlung, "Anaerobic Regulation of the Hydrogenase 1 (Hya) Operon of *Escherichia coli*." *J Bacteriol*, 176(17):5423-5428 (1994).
Calhoun, et al., "Energetic Efficiency of *Escherichia coli*: Effects of Mutations in Components of the Aerobic Respiratory Chain." *J Bacteriol*, 175(10):3020-3025 (1993).
Chang, et al., "Homofermentative Production of D- or L-Lactate in Metabolically Engineered *Escherichia coli* RR1." *Appl Environ Microbiol*, 65(4):1384-1389 (1999).
Cherepanov and Wackernagel, "Gene Disruption in *Escherichia coli*: TcR and KmR Cassettes with the Option of Flp-Catalyzed Excision of the Antibiotic-Resistance Determinant." *Gene*, 158(1):9-14 (1995).
Cho, et al., "Pcr-Based Tandem Epitope Tagging System for *Escherichia coli* Genome Engineering." *Biotechniques*, 40(1):67 (2006).
Compan and Touati, "Anaerobic Activation of arcA Transcription in *Escherichia coli*: Roles of FNR and arcA." *Molecular Microbiology*, 11(5):955-964 (1994).
Conradt, et al., "Pyruvate Formate-Lyase (Inactive Form) and Pyruvate Formate-Lyase Activating Enzyme of *Escherichia coli*: Isolation and Structural Properties." *Arch Biochem Biophys*, 228(1):133-142 (1984).

(Continued)

*Primary Examiner* — Delia Ramirez
(74) *Attorney, Agent, or Firm* — Medlen & Carroll, LLP

(57) ABSTRACT

The invention provides transgenic *Escherichia coli* cells comprising a mutation in cydAB gene, and/or cyoABCD gene, and/or cbdAB gene, and/or ygiN gene, wherein the mutation reduces (preferably, but not necessarily, by 100%) the cytochrome oxydase activity of a protein encoded by cydAB gene, and/or cyoABCD gene, and/or cbdAB gene, and/or ygiN gene. In a preferred embodiment, the mutation is a deletion of the cydAB gene, cyoABCD gene, and cbdAB gene. In another embodiment, the mutation is a deletion of the cydAB gene, cyoABCD gene, cbdAB gene, and ygiN gene. In another embodiment, the transgenic *Escherichia coli* cell, which comprises a deletion of cydAB gene, and/or cyoABCD gene, and/or cbdAB gene, and/or ygiN gene a) has substantially the same level of growth in oxic conditions as the level of growth in anoxic conditions of *Escherichia coli* that lacks said deletion of cydAB gene, and/or cyoABCD gene, and/or cbdAB gene, and/or ygiN gene, and b) is capable of converting glucose to D-lactate and/or amino acid and/or 2,3-butanediol (2,3-BDO) under one or both of oxic conditions and anoxic conditions.

10 Claims, 24 Drawing Sheets

(56) References Cited

PUBLICATIONS

Covert, et al., "Integrating High-Throughput and Computational Data Elucidates Bacterial Networks." *Nature*, 429(6987):92-96 (2004).

Dassa, et al., "A New Oxygen-Regulated Operon in *Escherichia coli* Comprises the Genes for a Putative Third Cytochrome Oxidase and for pH 2.5 Acid Phosphatase (Appa)." *Mol Gen Genet*, 229(3):341-352 (1991).

Datsenko and Wanner, "One-Step Inactivation of Chromosomal Genes in *Escherichia coli* K-12 Using PCR Products." *Proc Natl Acad Sci U S A*, 97(12):6640-6645 (2000).

Edgar, et al., "Gene Expression Omnibus: NCBI Gene Expression and Hybridization Array Data Repository." *Nucleic Acids Res*, 30(1):207-210 (2002).

Edwards and Palsson, "Metabolic Flux Balance Analysis and the in Silico Analysis of *Escherichia coli* K-12 Gene Deletions." *BMC Bioinformatics*, 1:1 (2000a).

Edwards and Palsson, "Robustness Analysis of the *Escherichia coli* Metabolic Network." *Biotechnol Prog*, 16(6):927-939 (2000b).

Edwards, et al., "In Silico Predictions of *Escherichia coli* Metabolic Capabilities Are Consistent with Experimental Data." *Nat Biotechnol*, 19(2):125-130 (2001).

Feist, et al., "A Genome-Scale Metabolic Reconstruction for *Escherichia coli* K-12 MG1655 That Accounts for 1260 ORFs and Thermodynamic Information." *Mol Syst Biol*, 3:121 (2007).

Feist and Palsson, "The Growing Scope of Applications of Genome-Scale Metabolic Reconstructions Using *Escherichia coli*." *Nat Biotechnol*, 26(6):659-667 (2008).

Fischer and Sauer, "Metabolic Flux Profiling of *Escherichia coli* Mutants in Central Carbon Metabolism Using Gc-Ms." *European J of Biochemistry*, 270(5):880-891 (2003).

Fong, et al., "In Silico Design and Adaptive Evolution of *Escherichia coli* for Production of Lactic Acid." *Biotechnol Bioeng*, 91(5):643-648 (2005).

Fong, et al., "Latent Pathway Activation and Increased Pathway Capacity Enable *Escherichia coli* Adaptation to Loss of Key Metabolic Enzymes." *J Biol Chem*, 281(12):8024-8033 (2006).

Gama-Castro, et al., "Regulondb (Version 6.0): Gene Regulation Model of *Escherichia coli* K-12 Beyond Transcription, Active (Experimental) Annotated Promoters and Textpresso Navigation." *Nucleic Acids Res*, 36(Database issue):D120-124 (2008).

Georgellis, et al., "Quinones as the Redox Signal for the Arc Two-Component System of Bacteria." *Science*, 292(5525):2314-2316 (2001).

Gunsalus and Park, "Aerobic-Anaerobic Gene Regulation in *Escherichia coli*: Control by the arcAB and FNR Regulons." *Res Microbiol*, 145(5-6):437-450 (1994).

Herring, et al., "Comparative Genome Sequencing of *Escherichia coli* Allows Observation of Bacterial Evolution on a Laboratory Timescale." *Nat Genet*, 38(12):1406-1412 (2006).

Hua, et al., "Metabolic Characterization of *Escherichia coli* Strains Adapted to Growth on Lactate." *Appl Environ Microbiol*, 73(14):4639-4647 (2007).

Iuchi and Lin, "arcA (Dye), a Global Regulatory Gene in *Escherichia coli* Mediating Repression of Enzymes in Aerobic Pathways." *Proc Natl Acad Sci U S A*, 85(6):1888-1892 (1988).

Iuchi and Lin, "Adaptation of *Escherichia coli* to Redox Environments by Gene Expression." *Mol Microbiol*, 9(1):9-15 (1993).

Iverson, et al., "Structure of the *Escherichia coli* Fumarate Reductase Respiratory Complex." *Science*, 284(5422):1961-1966 (1999).

Jaworowski, et al., "Genetic Identification and Purification of the Respiratory NADH Dehydrogenase of *Escherichia coli*." *Biochemistry*, 20(7):2041-2047 (1981).

Jervis, et al., "The $O_2$ Sensitivity of the Transcription Factor FNR Is Controlled by Ser24 Modulating the Kinetics of [4fe-4s] to [2fe-2s] Conversion." *Proc Natl Acad Sci U S A*, 106(12):4659-4664 (2009).

Joyce, et al., "Experimental and Computational Assessment of Conditionally Essential Genes in *Escherichia coli*." *J of Bacteriology*, 188(23):8259-8271 (2006).

Kanehisa, et al., "KEGG for Representation and Analysis of Molecular Networks Involving Diseases and Drugs." *Nucleic Acids Res*, 38(Database issue):D355-360 (2010).

Kang, et al., "Genome-Wide Expression Analysis Indicates That FNR of *Escherichia coli* K-12 Regulates a Large Number of Genes of Unknown Function." *J Bacteriol*, 187(3):1135-1160 (2005).

Karp, et al., "Multidimensional Annotation of the *Escherichia coli* K-12 Genome." *Nucleic Acids Res*, 35(22):7577-7590 (2007).

Keseler, et al., "EcoCyc: A Comprehensive View of *Escherichia coli* Biology." *Nucleic Acids Res*, 37(Database issue):D464-470 (2009).

Kita, et al., "Terminal Oxidases of *Escherichia coli* Aerobic Respiratory Chain. II. Purification and Properties of Cytochrome B558-D Complex from Cells Grown with Limited Oxygen and Evidence of Branched Electron-Carrying Systems." *J Biol Chem*, 259(5):3375-3381 (1984).

Knappe and Sawers, "A Radical-Chemical Route to Acetyl-CoA: The Anaerobically Induced Pyruvate Formate-Lyase System of *Escherichia coli*." *FEMS Microbiol Rev*, 6(4):383-398 (1990).

Lee, et al., "Systems Metabolic Engineering of *Escherichia coli* for L-Threonine Production." *Mol Syst Biol*, 3:149 (2007).

Lee, et al., "Metabolic Engineering of *Escherichia coli* for Enhanced Production of Succinic Acid, Based on Genome Comparison and in Silico Gene Knockout Simulation." *Appl Environ Microbiol*, 71(12):7880-7887 (2005).

Lynch and Lin, "Transcriptional Control Mediated by the arcA Two-Component Response Regulator Protein of *Escherichia coli*: Characterization of DNA Binding at Target Promoters." *J of Bacteriology*, 178(21):6238-6249 (1996).

Murray and Conway, "Multiple Regulators Control Expression of the Entner-Doudoroff Aldolase (E D A) of *Escherichia coli*." *J of Bacteriology*, 187(3):991-1000 (2005).

Neidhardt, et al., "Culture Medium for Enterobacteria." *J Bacteriol*, 119(3):736-747 (1974).

Newton and Gennis "In Vivo Assembly of the Cytochrome D Terminal Oxidase Complex of *Escherichia coli* from Genes Encoding the Two Subunits Expressed on Separate Plasmids." *Biochim Biophys Acta*, 1089(1):8-12 (1991).

Portnoy, et al., "Aerobic Fermentation of D-Glucose by an Evolved Cytochrome Oxidase-Deficient *Escherichia coli* Strain." *Appl Environ Microbiol*, 74(24):7561-7569 (2008).

Puustinen, et al., "Properties of the Two Terminal Oxidases of *Escherichia coli*." *Biochemistry*, 30(16):3936-3942 (1991).

Rasmussen, et al., "Carbon Metabolism Regulates Expression of the *pfl* (Pyruvate Formate-Lyase) Gene in *Escherichia coli*." *J of Bacteriology*, 173(20):6390-6397 (1991).

Salmon, et al., "Global Gene Expression Profiling in *Escherichia coli* K12: The effects of oxygen availability and FNR." *J Biol Chem*, 278 (32): 29837-29855 (2003).

Schilling, et al., "Combining Pathway Analysis with Flux Balance Analysis for the Comprehensive Study of Metabolic Systems." *Biotechnol Bioeng*, 71(4):286-306 (2000).

Scott, et al., "DNA Target Sequence and FNR-Dependent Gene Expression." *FEBS Lett*, 541(1-3):97-101 (2003).

Shestopalov, et al., "Aeration-Dependent Changes in Composition of the Quinone Pool in *Escherichia coli*. Evidence of Post-Transcriptional Regulation of the Quinone Biosynthesis." *FEBS Lett*, 404(2-3):272-274 (1997).

Shioi, et al., "Signal Transduction in Chemotaxis to Oxygen in *Escherichia coli* and *Salmonella typhimurium*." *J Bacteriol*, 170(12):5507-5511 (1988).

Spiro and Guest, "FNR and Its Role in Oxygen-Regulated Gene Expression in *Escherichia coli*." *FEMS Microbiol Rev*, 6(4):399-428 (1990).

Spiro and Guest, "Adaptive Responses to Oxygen Limitation in *Escherichia coli*." *Trends Biochem Sci*, 16(8):310-314 (1991).

Storey and Tibshirani "Statistical Significance for Genomewide Studies." *Proc Natl Acad Sci U S A*, 100(16):9440-9445 (2003).

Sturr, et al., "Purification of a Cytochrome *bd* Terminal Oxidase Encoded by the *Escherichia coli* App Locus from a DeltaCyo DeltaCyd Strain Complemented by Genes from *Bacillus firmus* OF4." *J Bacteriol*, 178(6):1742-1749 (1996).

(56) References Cited

OTHER PUBLICATIONS

Sutton, et al., "Kinetic Analysis of the Oxidative Conversion of the [4Fe-4S]2+ Cluster of FNR to a [2Fe-2S]2+ Cluster." *J Bacteriol*, 186(23):8018-8025 (2004).

Szyperski "Biosynthetically Directed Fractional 13c-Labeling of Proteinogenic Amino Acids." *European J of Biochemistry*, 232(2):433-448 (1995).

van Winden, et al., "Correcting Mass Isotopomer Distributions for Naturally Occurring Isotopes." *Biotechnol Bioeng*, 80(4):477-479 (2002).

Wendisch, et al., "Metabolic Engineering of *Escherichia coli* and *Corynebacterium glutamicum* for Biotechnological Production of Organic Acids and Amino Acids." *Curr Opin Microbiol*, 9(3):268-274 (2006).

Yagi and Matsuno-Yagi, "The Proton-Translocating Nadh-Quinone Oxidoreductase in the Respiratory Chain: The Secret Unlocked." *Biochemistry*, 42(8):2266-2274 (2003).

Zhu, et al., "Homolactate Fermentation by Metabolically Engineered *Escherichia coli* Strains." *Appl Environ Microbiol*, 73(2):456-464 (2007).

* cited by examiner

*(A)* cydA gene (SEQ ID NO:01)

ATGTTAGATATAGTCGAACTGTCGCGCTTACAGTTTGCCTTGACCGCGATGTACCACTTCCTTTTTGTGCCA
CTGACGCTCGGTATGGCGTTCCTGCTGGCCATTATGGAAACGGTCTACGTCCTCTCCGGCAAACAGATTTAT
AAAGATATGACCAAGTTCTGGGGCAAGTTGTTTGGTATCAACTTCGCTCTGGGTGTGGCTACCGGTCTGAC
CATGGAGTTCCAGTTCGGGACTAACTGGTCTTACTATTCCCACTATGTAGGGGATATCTTCGGTGCGCCGCT
GGCAATCGAAGGTCTGATGGCCTTCTTCCTCGAATCCACCTTTGTAGGTCTGTTCTTCTTCGGTTGGGATCG
TCTGGGTAAAGTTCAGCATATGTGTGTCACCTGGCTGGTGGCGCTCGGTTCAAACCTGTCCGCACTGTGGA
TTCTGGTTGCGAACGGCTGGATGCAAAACCCAATCGCGTCCGATTTCAACTTTGAAACTATGCGTATGGAGA
TGGTGAGCTTCTCCGAGCTGGTGCTTAACCCGGTTGCTCAGGTGAAATTCGTTCACACTGTAGCGTCTGGTT
ATGTGACTGGCGCGATGTTCATCCTCGGTATCAGCGCATGGTATATGCTGAAAGGTCGTGACTTCGCCTTC
GCTAAACGCTCCTTTGCTATCGCTGCCAGCTTCGGTATGGCTGCTGTTCTGTCTGTTATTGTTCTGGGTGAT
GAATCCGGCTACGAAATGGGCGACGTGCAGAAAACCAAACTGGCTGCTATTGAAGCCGAGTGGGAAACGCA
ACCTGCGCCTGCTGCCTTTACTCTGTTCGGCATTCCTGATCAGGAAGAGGAGACGAACAAATTTGCGATTCA
GATCCCTTACGCACTGGGCATCATTGCAACGCGTTCCGTGGATACCCCGGTTATCGGCCTGAAAGAGCTGA
TGGTGCAGCATGAAGAACGCATTCGTAACGGGATGAAGGCGTACTCTCTGCTCGAACAACTGCGTTCTGGT
TCTACCGACCAGGCGGTTCGTGACCAGTTCAATAGCATGAAGAAAGACCTCGGTTACGGTCTGCTGCTGAA
ACGCTATACGCCAAACGTGGCTGATGCGACTGAAGCGCAGATTCAACAGGCAACCAAAGACTCCATCCCGC
GTGTAGCGCCGCTGTACTTTGCGTTCCGTATCATGGTGGCGTGTGGCTTCCTGCTTCTGGCAATCATCGCGC
TCTCTTTCTGGAGTGTCATCCGCAACCGCATTGGCGAGAAAAAATGGCTTCTGCGCGCCGCGCTGTACGGT
ATTCCGCTGCCGTGGATTGCTGTAGAAGCGGGCTGGTTCGTGGCTGAATATGGCCGCCAACCGTGGGCTAT
CGGTGAAGTGCTGCCGACAGCTGTGGCGAACTCGTCACTGACCGCAGGCGATCTCATCTTCTCAATGGTGC
TGATTTGCGGCCTGTATACCCTGTTCCTGGTGGCAGAATTGTTCTTAATGTTCAAGTTTGCACGCCTCGGCC
CAAGCAGCCTGAAAACCGGTCGCTATCACTTTGAGCAGTCTTCCACGACTACTCAGCCGGCACGCTAA

*(B)* cydB gene (SEQ ID NO:02)

ATGATCGATTATGAAGTATTGCGTTTTATCTGGTGGCTGCTGGTTGGCGTTCTGCTGATTGGTTTTGCAGTC
ACTGACGGTTTCGACATGGGGGTGGGCATGCTCACCCGTTTCCTCGGTCGTAACGACACCGAGCGTCGAAT
TATGATTAACTCCATTGCACCACACTGGGACGGTAACCAGGTTTGGCTGATCACCGCGGGCGGCGCACTCT
TTGCTGCCTGGCCGTGGTCTATGCCGCTGCGTTCTCCGGCTTCTATGTGGCGATGATCCTCGTGCTGGCGT
CTTTGTTCTTCCGTCCGGTCGGTTTTGACTACCGCTCCAAGATTGAAGAAACCCGCTGGCGTAACATGTGGG
ACTGGGGCATCTTCATTGGTAGCTTCGTTCCGCCGCTGGTAATTGGTGTAGCGTTCGGTAACCTGTTGCAG
GGCGTACCGTTCAACGTTGATGAATATCTGCGTCTGTACTACACCGGTAACTTCTTCCAGTTGCTTAACCCG
TTCGGCCTGCTGGCAGGCGTGGTGAGCGTAGGGATGATCATTACTCAGGGCGCAACCTATCTGCAAATGCG
TACCGTGGGCGAACTGCACCTGCGTACCCGTGCAACGGCTCAGGTGGCTGCGCTGGTGACACTGGTCTGTT
TCGCACTGGCTGGCGTATGGGTGATGTACGGTATCGATGGTTATGTCGTGAAATCGACAATGGACCATTAC
GCAGCCTCTAACCCACTGAATAAAGAAGTGGTTCGTGAAGCTGGCGCATGGCTGGTTAACTTCAACAACAC
GCCAATTCTGTGGGCTATTCCGGCACTGGGTGTGGTTCTGCCGCTGCTGACCATCCTGACTGCACGTATGG
ATAAAGCCGCGTGGGCGTTTGTGTTCTCCTCCCTGACGCTGGCCTGCATCATCCTGACAGCCGGTATCGCA
ATGTTCCCGTTTGTGATGCCGTCCAGCACCATGATGAACGCAAGTCTGACAATGTGGGATGCAACTTCCAG
CCAGCTGACGCTTAACGTCATGACCTGGGTTGCGGTGGTTCTGGTACCGATCATTCTGCTCTACACCGCCTG
GTGTTACTGGAAAATGTTCGGTCGTATCACCAAAGAAGATATTGAACGTAACACCCACTCTCTGTACTAA

*(C)* cyoA gene (SEQ ID NO:03)

ATGAGACTCAGGAAATACAATAAAAGTTTGGGATGGTTGTCATTATTTGCAGGCACTGTATTGCTCAGTGGC
TGTAATTCTGCGCTGTTAGATCCCAAAGGACAGATTGGTCTGGAGCAACGTTCACTGATACTGACGGCATTT
GGCCTGATGTTGATTGTCGTTATTCCCGCAATCTTGATGGCTGTTGGTTTCGCCTGGAAGTACCGTGCGAGC
AATAAAGATGCTAAGTACAGCCCGAACTGGTCACACTCCAATAAAGTGGAAGCTGTGGTCTGGACGGTACC
TATCTTAATCATCATCTTCCTTGCAGTACTGACCTGGAAAACCACTCACGCTCTTGAGCCTAGCAAGCCGCT
GGCACACGACGAGAAGCCCATTACCATCGAAGTGGTTTCCATGGACTGGAAATGGTTCTTCATCTACCCGG
AACAGGGCATTGCTACCGTGAATGAAATCGCTTTCCCGGCGAACACTCCGGTGTACTTCAAAGTGACCTCC

AACTCCGTGATGAACTCCTTCTTCATTCCGCGTCTGGGTAGCCAGATTTATGCCATGGCCGGTATGCAGACT
CGCCTGCATCTGATCGCCAACGAACCCGGCACTTAT

GACGGTATCTCCGCCAGCTACAGCGGCCCGGGCTTCTCAGGCATGAAGTTCAAAGCTATTGCAACACCGGA
TCGCGCCGCATTCGACCAGTGGGTCGCAAAAGCGAAGCAGTCGCCGAACACCATGTCTGACATGGCTGCGT
TCGAAAAACTGGCCGCGCCTAGCGAATACAACCAGGTGGAATATTTCTCCAACGTGAAACCAGACTTGTTT
GCCGATGTAATTAACAAGTTTATGGCTCACGGTAAGAGCATGGACATGACCCAGCCAGAAGGTGAGCACAG
CGCACACGAAGGTATGGAAGGCATGGACATGAGCCACGCGGAATCCGCCCATTAA (D) *cyoB* gene (SEQ ID NO:04)

ATGTTCGGAAAATTATCACTTGATGCAGTCCCGTTCCATGAACCTATCGTCATGGTTACGATCGCTGGCATT
ATTTTGGGAGGTCTGGCGCTCGTTGGCCTGATCACTTACTTCGGTAAGTGGACCTACCTGTGGAAAGAGTG
GCTGACCTCCGTCGACCATAAACGCCTCGGTATCATGTATATCATCGTGGCGATTGTGATGTTGCTGCGTGG
TTTTGCTGACGCCATTATGATGCGTAGCCAGCAGGCTCTTGCCTCGGCGGGCGAAGCGGGCTTCCTGCCAC
CTCACCACTACGATCAGATCTTTACCGCGCACGGCGTGATTATGATCTTCTTCGTGGCGATGCCTTTCGTTA
TCGGTCTGATGAACCTGGTGGTTCCGCTGCAGATCGGCGCGCGTGACGTTGCGTTCCCGTTCCTCAACAAC
TTAAGCTTCTGGTTTACCGTTGTTGGTGTGATTCTGGTTAACGTTTCTCTCGGCGTGGGCGAATTTGCGCAG
ACCGGCTGGCTGGCCTATCCACCGCTATCGGGAATAGAGTACAGTCCGGGAGTCGGTGTCGATTACTGGAT
ATGGAGTCTCCAGCTATCCGGTATAGGTACGACGCTTACCGGTATCAACTTCTTCGTTACCATTCTGAAGAT
GCGCGCACCGGGCATGACCATGTTCAAGATGCCAGTATTTACCTGGGCATCACTGTGCGCGAACGTACTGA
TTATTGCTTCCTTCCCAATTCTGACGGTTACCGTCGCGTTGTTGACCCTGGATCGCTATCTGGGCACCCATT
TCTTTACCAACGATATGGGTGGCAACATGATGATGTACATCAACCTGATTTGGGCCTGGGGCCACCCGGAA
GTTTACATCCTGATCCTGCCTGTTTTCGGTGTGTTCTCCGAAATTGCGGCAACCTTCTCGCGTAAACGTCTG
TTTGGTTATACCTCGCTGGTATGGGCAACCGTCTGTATCACCGTGCTGTCGTTCATCGTTTGGCTGCACCAC
TTCTTTACGATGGGTGCGGGCGCGAACGTAAACGCCTTCTTTGGTATCACCACAATGATTATCGCCATCCCG
ACCGGGGTGAAGATCTTCAACTGGCTGTTCACCATGTATCAGGGCCGCATCGTGTTCCATTCTGCGATGCT
GTGGACCATCGGTTTTATCGTCACCTTCTCGGTGGGCGGGATGACTGGCGTGCTGCTGGCCGTACCGGGCG
CGGACTTCGTTCTGCATAACAGCCTGTTCCTGATTGCGCACTTCCATAACGTGATCATCGGCGGCGTGGTCT
TCGGCTGCTTCGCAGGGATGACCTACTGGTGGCCTAAAGCGTTCGGTTTCAAACTGAACGAAACCTGGGGT
AAACGCGCGTTCTGGTTCTGGATCATCGGCTTCTTCGTTGCCTTTATGCCACTGTATGCGCTGGGCTTCATG
GGCATGACCCGTCGTTTGAGCCAGCAGATTGACCCGCAGTTCCACACCATGCTGATGATTGCAGCCAGCGG
TGCAGTACTGATTGCGCTGGGTATTCTCTGCCTCGTTATTCAGATGTACGTTTCTATTCGCGACCGCGACCA
GAACCGTGACCTGACTGGCGACCCGTGGGGTGGCCGTACGCTGGAGTGGGCAACCTCTTCCCCGCCTCCGT
TCTATAACTTTGCCGTAGTGCCGCACGTTCACGAACGTGATGCATTCTGGGAAATGAAAGAGAAAGGCGAA
GCGTATAAAAAGCCTGACCACTATGAAGAAATTCATATGCCGAAAAACAGCGGTGCAGGTATCGTCATTGC
AGCTTTCTCCACCATCTTCGGTTTCGCCATGATCTGGCATATCTGGTGGCTGGCGATTGTTGGCTTCGCAGG
CATGATCATCACCTGGATCGTGAAAAGCTTCGACGAGGACGTGGATTACTACGTGCCGGTGGCAGAAATCG
AAAAACTGGAAAACCAGCATTTCGATGAGATTACTAAGGCAGGGCTGAAAAATGGCAACTGA (E) *cyoC* gene (SEQ ID NO:05)

ATGGCAACTGATACTTTGACGCACGCGACTGCCCACGCGCACGAACACGGGCACCACGATGCAGGCGGAAC
CAAAATCTTCGGATTTTGGATCTACCTGATGAGCGACTGCATTCTGTTCTCTATCTTGTTTGCTACCTATGCC
GTTCTGGTGAACGGCACCGCAGGCGGCCCGACAGGTAAGGACATTTTCGAACTGCCGTTCGTTCTGGTTGA
AACTTTCTTGCTGTTGTTCAGCTCCATCACCTACGGCATGGCGGCTATCGCCATGTACAAAAACAACAAAAG
CCAGGTTATCTCCTGGCTGGCGTTGACCTGGTTGTTTGGTGCCGGATTTATCGGGATGGAAATCTATGAATT
CCATCACCTGATTGTTAACGGCATGGGTCCGGATCGCAGCGGCTTCCTGTCAGCGTTCTTTGCGCTGGTCG
GCACGCACGGTCTGCACGTCACTTCTGGTCTTATCTGGATGGCGGTGCTGATGGTGCAAATCGCCCGTCGC
GGCCTGACCAGCACTAACCGTACCCGCATCATGTGCCTGAGCCTGTTCTGGCACTTCCTGGATGTGGTTTG
GATCTGTGTGTTCACTGTTGTTTATCTGATGGGGGCGATGTAA

*(F) cyoD* gene (SEQ ID NO:06)

ATGAGTCATTCTACCGATCACAGCGGCGCGTCCCATGGCAGCGTAAAAACCTACATGACAGGCTTTATCCT
GTCGATCATTCTGACGGTGATTCCGTTCTGGATGGTGATGACAGGAGCTGCCTCTCCGGCCGTAATTCTGG
GAACAATCCTGGCAATGGCAGTGGTACAGGTTCTGGTGCATCTGGTGTGCTTCCTGCACATGAATACCAAA
TCAGATGAAGGCTGGAACATGACGGCGTTTGTCTTCACCGTGCTAATCATCGCTATCCTGGTTGTAGGCTCC
ATCTGGATTATGTGGAACCTCAACTACAACATGATGATGCACTAA

*(G) cbdA* gene (SEQ ID NO:07)

ATGTGGGATGTCATTGATTTATCGCGCTGGCAGTTTGCTCTGACCGCGCTGTATCACTTTTTATTTGTACCC
CTTACCCTGGGGCTGATTTTTTTGCTGGCTATTATGGAAACCATTTACGTGGTCACCGGCAAAACAATCTAC
CGCGATATGACGCGCTTCTGGGGTAAGCTCTTCGGTATCAATTTTGCTCTTGGCGTGGCTACCGGCCTGAC
CATGGAGTTTCAGTTTGGTACTAACTGGTCATTCTATTCCAACTATGTGGGCGATATTTTTGGCGCACCGCT
GGCGATGGAAGCATTAATGGCCTTCTTCCTCGAATCCACCTTTGTCGGGCTGTTCTTCTTCGGCTGGCAACG
GCTGAATAAATACCAGCACCTGCTGGTGACGTGGCTGGTGGCGTTCGGTTCAAATCTCTCTGCGTTGTGGA
TATTGAATGCCAACGGTTGGATGCAATACCCGACCGGTGCGCATTTTGATATCGACACCCTGCGTATGGAG
ATGACCAGCTTCAGCGAGCTGGTCTTTAATCCGGTCAGCCAGGTGAAATTTGTGCACACCGTAATGGCGGG
CTACGTGACCGGGGCCATGTTTATTATGGCGATCAGCGCCTGGTATTTACTGCGCGGACGGGAGCGCAATG
TCGCATTACGCTCGTTTGCCATCGGTTCCGTCTTCGGTACTCTGGCGATTATCGGTACCCTGCAACTCGGAG
ACAGTTCTGCGTATGAAGTCGCGCAAGTACAACCGGTAAAACTGGCGGCGATGGAAGGGGAGTGGCAAAC
GGAACCTGCACCTGCACCGTTCCATGTGGTTGCCTGGCCGGAACAGGATCAAGAGCGTAACGCCTTTGCCC
TCAAAATTCCCGCGCTGCTAGGGATCCTCGCCACTCACTCATTAGATAAACCCGTGCCGGGTCTGAAGAATT
TGATGGCTGAAACCTACCCACGCCTTGCAACGCGGACGTATGGCCTGGCTGTTAATGCAGGAAATATCGCAA
GGCAATCGTGAGCCGCATGTGTTGCAGGCATTCCGGGGACTGGAAGGTGACCTGGGCTACGGCATGTTGCT
CTCCCGCTATGCGCCGGATATGAATCATGTCACAGCCGCACAGTACCAGGCGGCGATGCGTGGCGCGATAC
CTCAGGTTGCGCCGGTATTCTGGAGTTTCCGCATCATGGTGGGCTGTGGTTCCCTGCTGCTACTGGTGATG
CTGATTGCGCTTGTCCAGACGCTGCGTGGCAAAATCGACCAGCATCGCTGGGTGCTGAAAATGGCGCTCTG
GAGTTTGCCGTTGCCGTGGATTGCGATTGAAGCCGGGTGGTTTATGACCGAGTTTGGTCGTCAGCCGTGGG
CGATACAGGACATCTTACCGACATACTCCGCGCACTCCGCTTTAACCACAGGACAACTGGCTTTCTCACTGA
TCATGATCGTAGGGCTTTACACCCTGTTCTTAATCGCCGAAGTCTACCTGATGCAGAAATATGCCCGTCTGG
GGCCGAGCGCGATGCAGAGTGAACAACCGACGCAGCAACAGGGGTAA

*(H) cbdB* gene (SEQ ID NO:08)

ATGTTTGATTATGAAACATTGCGCTTCATCTGGTGGCTGCTGATTGGCGTGATCCTGGTGGTCTTTATGATC
TCCGACGGATTTGACATGGGGATCGGCTGTCTGCTGCCGCTGGTGGCGCGTAATGATGATGAACGCCGGAT
AGTGATAAACAGCGTTGGTGCACACTGGGAAGGCAACCAGGTCTGGTTGATCCTCGCTGGTGGGCATTAT
TTGCCGCCTGGCCCAGAGTGTATGCAGCGGCGTTTTCCGGCTTTTATGTGGCGATGATCCTGGTGCTGTGC
TCACTGTTCTTCCGCCCGCTGGCCTTTGATTATCGCGGAAAAATCGCCGATGCACGCTGGCGTAAAATGTG
GGACGCCGGTCTGGTCATCGGCAGTCTGGTGCCGCCGGTAGTCTTCGGTATCGCCTTCGGCAACTTGTTGC
TCGGCGTGCCGTTTGCCTTCACACCGCAATTACGCGTGGAGTATCTCGGCAGCTTCTGGCAACTGCTGACG
CCATTCCCTTTATTGTGCGGATTGCTCAGCCTTGGGATGGTGATTTGCAAGGTGGCGTCTGGTTACAACTG
AAAACTGTTGGTGTGATTCATCTGCGTTCACAGCTGGCGACCAAACGCGCTGCACTGTTGGTGATGCTGTG
CTTTTTGCTGGCGGGTTACTGGCTGTGGGTCGGTATTGATGGCTTTGTACTGCTCGCCCAGGATGCTAACG
GTCCTTCCAATCCGTTAATGAAACTGGTGGCAGTGCTACCTGGTGCCTGGATGAATAATTTTGTCGAGTCGC
CCGTTTTGTGGATCTTCCCGCTGCTGGGATTCTTCTGCCCATTGCTGACGGTGATGGCGATTTATCGTGGTC
GCCCGGGTTGGGGATTTTGATGGCATCATTGATGCAATTTGGCGTGATTTTCACGGCAGGCATCACGCTG
TTCCCCTTTGTCATGCCGTCAAGCGTGAGTCCGATCTCCAGCCTGACGTTGTGGGACAGTACTTCCAGTCAG
CTGACGCTGAGCATTATGTTGGTAATCGTGCTGATATTTTTGCCCATTGTGTTGCTCTACACTCTCTGGAGC
TACTACAAAATGTGGGGGCGCATGACAACAGAAACTCTCCGCCGTAACGAAAACGAGTTGTACTAA

*(I) ygiN* gene (SEQ ID NO:09)

ATGCTTACCGTAATCGCAGAAATCCGTACTCGTCCTGGTCAACATCACCGTCAGGCGGTATTGGATCAGTTT
GCTAAAATCGTTCCAACCGTACTGAAAGAAGAAGGTTGCCACGGCTATGCGCCAATGGTGGATTGCGCAGC
TGGCGTGAGTTTCCAGTCTATGGCACCGGATTCTATCGTGATGATTGAGCAGTGGGAAAGCATCGCGCATC
TTGAAGCGCATCTGCAAACCCCGCACATGAAGGCGTATAGCGAAGCCGTAAAAGGTGACGTGCTGGAGATG
AATATCCGTATTCTGCAGCCAGGGATTTAA

*(J) sodA* gene (SEQ ID NO:10)

ATGAGCTATACCCTGCCATCCCTGCCGTATGCTTACGATGCCCTGGAACCGCACTTCGATAAGCAGACCATG
GAAATCCACCACACCAAACACCATCAGACCTACGTAAACAACGCCAACGCGGCGCTGGAAAGCCTGCCAGA
ATTTGCCAACCTGCCGGTTGAAGAGCTGATCACCAAACTGGACCAGCTGCCAGCAGACAAGAAAACCGTAC
TGCGCAACAACGCTGGCGGTCACGCTAACCACAGCCTGTTCTGGAAAGGTCTGAAAAAAGGCACCACCCTG
CAGGGTGACCTGAAAGCGGCTATCGAACGTGACTTCGGCTCCGTTGATAACTTCAAAGCAGAATTTGAAAA
AGCGGCAGCTTCCCGCTTTGGTTCCGGCTGGGCATGGCTGGTGCTGAAAGGCGATAAACTGGCGGTGGTTT
CTACTGCTAACCAGGATTCTCCGCTGATGGGTGAAGCTATTTCTGGCGCTTCCGGCTTCCCGATTATGGGCC
TGGATGTGTGGGAACATGCTTACTACCTGAAATTCCAGAACCGCCGTCCGGACTACATTAAAGAGTTCTGG
AACGTGGTGAACTGGGACGAAGCAGCGGCACGTTTTGCGGCGAAAAAATAA

*(K) sodB* gene (SEQ ID NO:11)

ATGTCATTCGAATTACCTGCACTACCATATGCTAAAGATGCTCTGGCACCGCACATTTCTGCGGAAACCATC
GAGTATCACTACGGCAAGCACCATCAGACTTATGTCACTAACCTGAACAACCTGATTAAAGGTACCGCGTTT
GAAGGTAAATCACTGGAAGAGATTATTCGCAGCTCTGAAGGTGGCGTATTCAACAACGCAGCTCAGGTCTG
GAACCATACTTTCTACTGGAACTGCCTGGCACCGAACGCCGGTGGCGAACCGACTGGAAAAGTCGCTGAAG
CTATCGCCGCATCTTTTGGCAGCTTTGCCGATTTCAAAGCGCAGTTTACTGATGCAGCGATCAAAAACTTTG
GTTCTGGCTGGACCTGGCTGGTGAAAAACAGCGATGGCAAACTGGCTATCGTTTCAACCTCTAACGCGGGT
ACTCCGCTGACCACCGATGCGACTCCGCTGCTGACCGTTGATGTCTGGGAACACGCTTATTACATCGACTAT
CGCAATGCACGTCCTGGCTATCTGGAGCACTTCTGGGCGCTGGTGAACTGGGAATTCGTAGCGAAAAATCT
CGCTGCATAA

```
                          SEQUENCE LISTING

<160> NUMBER OF SEQ ID NOS: 27

<210> SEQ ID NO 1
<211> LENGTH: 1569
<212> TYPE: DNA
<213> ORGANISM: Escherichia coli

<400> SEQUENCE: 1
atgttagata tagtcgaact gtcgcgctta cagtttgcct tgaccgcgat gtaccacttc      60 cttttgtgc cactgacgct cggtatggcg ttcctgctgg ccattatgga aacggtctac     120
gtcctctccg gcaaacagat ttataaagat atgaccaagt tctggggcaa gttgtttggt     180
atcaacttcg ctctgggtgt ggctaccggt ctgaccatgg agttccagtt cgggactaac     240
tggtcttact attcccacta tgtaggggat atcttcggtg cgccgctggc aatcgaaggt     300
ctgatggcct tcttcctcga atccaccttt gtaggtctgt tcttcttcgg ttgggatcgt     360
ctgggtaaag ttcagcatat gtgtgtcacc tggctggtgg cgctcggttc aaacctgtcc     420
gcactgtgga ttctggttgc gaacggctgg atgcaaaacc caatcgcgtc cgatttcaac    480
```

-continued

```
tttgaaacta tgcgtatgga gatggtgagc ttctccgagc tggtgcttaa cccggttgct      540
caggtgaaat tcgttcacac tgtagcgtct ggttatgtga ctggcgcgat gttcatcctc      600
ggtatcagcg catggtatat gctgaaaggt cgtgacttcg ccttcgctaa cgctcctttt      660
gctatcgctg ccagcttcgg tatggctgct gttctgtctg ttattgttct gggtgatgaa      720
tccggctacg aaatgggcga cgtgcagaaa accaaactgg ctgctattga agccgagtgg      780
gaaacgcaac tgcgcctgc tgcctttact ctgttcggca ttcctgatca ggaagaggag       840
acgaacaaat tgcgattca gatcccttac gcactgggca tcattgcaac gcgttccgtg      900 gatacccccgg ttatcggcct gaaagagctg atggtgcagc atgaagaacg cattcgtaac     960
gggatgaagg cgtactctct gctcgaacaa ctgcgttctg gttctaccga ccaggcggtt    1020
cgtgaccagt tcaatagcat gaagaaagac ctcggttacg gtctgctgct gaaacgctat    1080
acgccaaacg tggctgatgc gactgaagcg cagattcaac aggcaaccaa agactccatc    1140
ccgcgtgtag cgccgctgta ctttgcgttc cgtatcatgg tggcgtgtgg cttcctgctt    1200
ctggcaatca tcgcgctctc tttctggagt gtcatccgca accgcattgg cgagaaaaaa    1260
tggcttctgc gcgccgcgct gtacggtatt ccgctgccgt ggattgctgt agaagcgggc    1320
tggttcgtgg ctgaatatgg ccgccaaccg tgggctatcg gtgaagtgct gccgacagct    1380
gtggcgaact cgtcactgac cgcaggcgat ctcatcttct caatggtgct gatttgcggc    1440 ctgtatacccc tgttcctggt ggcagaattg ttcttaatgt tcaagtttgc acgcctcggc    1500
ccaagcagcc tgaaaaccgg tcgctatcac tttgagcagt cttccacgac tactcagccg    1560
gcacgctaa                                                            1569
```

<210> SEQ ID NO 2
<211> LENGTH: 1139
<212> TYPE: DNA
<213> ORGANISM: Escherichia coli

<400> SEQUENCE: 2

```
atgatcgatt atgaagtatt gcgttttatc tggtggctgc tggttggcgt tctgctgatt       60
ggttttgcag tcactgacgg tttcgacatg ggggtgggca tgctcacccg tttcctcggt      120
cgtaacgaca ccgagcgtcg aattatgatt aactccattg caccacactg ggacggtaac      180
caggtttggc tgatcaccgc gggcggcgca ctctttgctg cctggccgtg gtctatgccg      240
ctgcgttctc cggcttctat gtggcgatga tcctcgtgct ggcgtctttg ttcttccgtc      300
cggtcggttt tgactaccgc tccaagattg aagaaacccg ctggcgtaac atgtgggact      360
ggggcatctt cattggtagc ttcgttccgc cgctggtaat tggtgtagcg ttcggtaacc      420
tgttgcaggg cgtaccgttc aacgttgatg aatatctgcg tctgtactac accggtaact      480
tcttccagtt gcttaacccg ttcggcctgc tgcaggcgt ggtgagcgta gggatgatca       540
ttactcaggg cgcaacctat ctgcaaatgc gtaccgtggg cgaactgcac ctgcgtaccc      600
gtgcaacggc tcaggtggct cgcgctggtga cactggtctg tttcgcactg ctggcgtat     660 gggtgatgta cggtatcgat ggttatgtcg tgaaatcgac aatggaccat tacgcagcct      720
ctaacccact gaataaagaa gtggttcgtg aagctggcgc atggctggtt aacttcaaca      780
acacgccaat tctgtgggct attccggcac tgggtgtggt tctgccgctg ctgaccatcc      840
tgactgcacg tatggataaa gccgcgtggg cgtttgtgtt ctcctccctg acgctggcct      900
gcatcatcct gacagccggt atcgcaatgt tcccgtttgt gatgccgtcc agcaccatga      960
tgaacgcaag tctgacaatg tgggatgcaa cttccagcca gctgacgctt aacgtcatga    1020
```

```
cctgggttgc ggtggttctg gtaccgatca ttctgctcta caccgcctgg tgttactgga    1080
aaatgttcgg tcgtatcacc aaagaagata ttgaacgtaa cacccactct ctgtactaa     1139

<210> SEQ ID NO 3
<211> LENGTH: 948
<212> TYPE: DNA
<213> ORGANISM: Escherichia coli

<400> SEQUENCE: 3
atgagactca ggaaatacaa taaaagtttg ggatggttgt cattatttgc aggcactgta      60
ttgctcagtg gctgtaattc tgcgctgtta gatcccaaag acagattgg tctggagcaa     120 cgttcactga tactgacggc atttggcctg atgttgattg tcgttattcc cgcaatcttg     180
atggctgttg gtttcgcctg gaagtaccgt gcgagcaata agatgctaa gtacagcccg      240 aactggtcac actccaataa agtggaagct gtggtctgga cggtacctat cttaatcatc     300
atcttccttg cagtactgac ctggaaaacc actcacgctc ttgagcctag caagccgctg     360
gcacacgacg agaagcccat taccatcgaa gtggtttcca tggactggaa atggttcttc     420 atctaccgg aacagggcat tgctaccgt aatgaaatcg ctttcccggc gaacactccg       480
gtgtacttca agtgacctc caactccgtg atgaactcct tcttcattcc gcgtctgggt     540
agccagattt atgccatggc cggtatgcag actcgcctgc atctgatcgc caacgaaccc    600
ggcacttatg acggtatctc cgccagctac agcggcccgg gcttctcagg catgaagttc    660
aaagctattg caacaccgga tcgcgccgca ttcgaccagt gggtcgcaaa agcgaagcag    720
tcgccgaaca ccatgtctga catggctgcg ttcgaaaaac tggccgcgcc tagcgaatac    780
aaccaggtgg aatatttctc caacgtgaaa ccagacttgt ttgccgatgt aattaacaag    840
tttatggctc acggtaagag catggacatg acccagccag aaggtgagca cagcgcacac    900
gaaggtatgg aaggcatgga catgagccac gcggaatccg cccattaa                 948

<210> SEQ ID NO 4
<211> LENGTH: 1992
<212> TYPE: DNA
<213> ORGANISM: Escherichia coli

<400> SEQUENCE: 4
atgttcggaa aattatcact tgatgcagtc ccgttccatg aacctatcgt catggttacg     60
atcgctggca ttattttggg aggtctggcg ctcgttggcc tgatcactta cttcggtaag   120
tggacctacc tgtggaaaga gtggctgacc tccgtcgacc ataaacgcct cggtatcatg   180
tatatcatcg tggcgattgt gatgttgctg cgtggttttg ctgacgccat tatgatgcgt   240
agccagcagg ctcttgcctc ggcgggcgaa gcgggcttcc tgccacctca ccactacgat   300
cagatcttta ccgcgcacgg cgtgattatg atcttcttcg tggcgatgcc tttcgttatc   360
ggtctgatga acctggtggt tccgctgcag atcgcgcgc gtgacgttgc gttcccgttc   420
ctcaacaact taagcttctg gttaccgtt gttggtgtga ttctggttaa cgtttctctc   480
ggcgtgggcg aatttgcgca gaccggctgg ctggcctatc caccgctatc gggaatagag   540
tacagtccgg gagtcggtgt cgattactgg atatggagtc tccagctatc cggtatag gt   600 acgacgctta ccgtatcaa cttcttcgtt accattctga agatgcgcgc accgggcatg    660
accatgttca gatgccagt atttacctgg catcactgt gcgcgaacgt actgattatt     720
gcttccttcc caattctgac ggttaccgtc gcgttgttga ccctggatcg ctatctgggc    780
```

-continued

```
acccatttct ttaccaacga tatgggtggc aacatgatga tgtacatcaa cctgatttgg    840
gcctggggcc acccggaagt ttacatcctg atcctgcctg ttttcggtgt gttctccgaa    900
attgcggcaa ccttctcgcg taaacgtctg tttggttata cctcgctggt atgggcaacc    960
gtctgtatca ccgtgctgtc gttcatcgtt tggctgcacc acttctttac gatgggtgcg   1020
ggcgcgaacg taaacgcctt ctttggtatc accacaatga ttatcgccat cccgaccggg   1080
gtgaagatct tcaactggct gttcaccatg tatcagggcc gcatcgtgtt ccattctgcg   1140
atgctgtgga ccatcggttt tatcgtcacc ttctcggtgg gcgggatgac tggcgtgctg   1200
ctggccgtac cgggcgcgga cttcgttctg cataacagcc tgttcctgat gcgcacttc    1260
cataacgtga tcatcggcgg cgtggtcttc ggctgcttcg cagggatgac ctactggtgg   1320
cctaaagcgt tcggtttcaa actgaacgaa acctggggta aacgcgcgtt ctggttctgg   1380
atcatcggct tcttcgttgc ctttatgcca ctgtatgcgc tgggcttcat gggcatgacc   1440
cgtcgtttga gccagcagat tgacccgcag ttccacacca tgctgatgat tgcagccagc   1500
ggtgcagtac tgattgcgct gggtattctc tgcctcgtta ttcagatgta cgtttctatt   1560
cgcgaccgcg accagaaccg tgacctgact ggcgacccgt ggggtggccg tacgctggag   1620
tgggcaacct cttccccgcc tccgttctat aactttgccg tagtgccgca cgttcacgaa   1680
cgtgatgcat tctgggaaat gaaagagaaa ggcgaagcgt ataaaaagcc tgaccactat   1740
gaagaaattc atatgccgaa aaacagcggt gcaggtatcg tcattgcagc tttctccacc   1800
atcttcggtt tcgccatgat ctggcatatc tggtggctgg cgattgttgg cttcgcaggc   1860
atgatcatca cctggatcgt gaaaagcttc gacgaggacg tggattacta cgtgccggtg   1920
gcagaaatcg aaaaactgga aaaccagcat ttcgatgaga ttactaaggc agggctgaaa   1980
aatggcaact ga                                                        1992
```

```
<210> SEQ ID NO 5
<211> LENGTH: 615
<212> TYPE: DNA
<213> ORGANISM: Escherichia coli

<400> SEQUENCE: 5
```

```
atggcaactg atactttgac gcacgcgact gcccacgcgc acgaacacgg gcaccacgat    60
gcaggcggaa ccaaaatctt cggattttgg atctacctga tgagcgactg cattctgttc   120
tctatcttgt ttgctaccta tgccgttctg gtgaacggca ccgcaggcgg cccgacaggt   180
aaggacattt tcgaactgcc gttcgttctg gttgaaactt tcttgctgtt gttcagctcc   240
atcacctacg gcatggcggc tatcgccatg tacaaaaaca caaaagcca ggttatctcc   300
tggctggcgt tgacctggtt gtttggtgcc ggatttatcg ggatggaaat ctatgaattc   360
catcacctga ttgttaacgg catgggtccg gatcgcagcg gcttcctgtc agcgttcttt   420
gcgctggtcg gcacgcacgg tctgcacgtc acttctggtc ttatctggat ggcggtgctg   480
atggtgcaaa tcgcccgtcg cggcctgacc agcactaacc gtacccgcat catgtgcctg   540
agcctgttct ggcacttcct ggatgtggtt tggatctgtg tgttcactgt tgtttatctg   600
atgggggcga tgtaa                                                     615
```

```
<210> SEQ ID NO 6
<211> LENGTH: 330
<212> TYPE: DNA
<213> ORGANISM: Escherichia coli

<400> SEQUENCE: 6
```

```
atgagtcatt ctaccgatca cagcggcgcg tcccatggca gcgtaaaaac ctacatgaca    60
ggctttatcc tgtcgatcat tctgacggtg attccgttct ggatggtgat gacaggagct   120
gcctctccgg ccgtaattct gggaacaatc ctggcaatgg cagtggtaca ggttctggtg   180
catctggtgt gcttcctgca catgaatacc aaatcagatg aaggctggaa catgacggcg   240
tttgtcttca ccgtgctaat catcgctatc ctggttgtag ctccatctg gattatgtgg   300 aacctcaact acaacatgat gatgcactaa                                    330

<210> SEQ ID NO 7
<211> LENGTH: 1545
<212> TYPE: DNA
<213> ORGANISM: Escherichia coli

<400> SEQUENCE: 7
atgtgggatg tcattgattt atcgcgctgg cagtttgctc tgaccgcgct gtatcacttt    60
ttatttgtac cccttaccct ggggctgatt tttttgctgg ctattatgga aaccatttac   120
gtggtcaccg gcaaaacaat ctaccgcgat atgacgcgct tctggggtaa gctcttcggt   180
atcaattttg ctcttggcgt ggctaccggc ctgaccatgg agtttcagtt tggtactaac   240
tggtcattct attccaacta tgtgggcgat attttttggcg caccgctggc gatggaagca   300
ttaatggcct tcttcctcga atccaccttt gtcgggctgt tcttcttcgg ctggcaacgg   360
ctgaataaat accagcacct gctggtgacg tggctggtgg cgttcggttc aaatctctct   420
gcgttgtgga tattgaatgc caacggttgg atgcaatacc cgaccggtgc gcattttgat   480
atcgacaccc tgcgtatgga gatgaccagc ttcagcgagc tggtctttaa tccggtcagc   540
caggtgaaat ttgtgcacac cgtaatggcg ggctacgtga ccggggccat gtttattatg   600
gcgatcagcg cctggtattt actgcgcgga cgggagcgca atgtcgcatt acgctcgttt   660
gccatcggtt ccgtcttcgg tactctggcg attatcggta ccctgcaact cggagacagt   720
tctgcgtatg aagtcgcgca agtacaaccg gtaaaactgg cggcgatgga agggagtgg   780 caaacggaac ctgcacctgc accgttccat gtggttgcct ggccggaaca ggatcaagag   840
cgtaacgcct ttgccctcaa aattcccgcg ctgctaggga tcctcgccac tcactcatta   900
gataaacccg tgccgggtct gaagaatttg atggctgaaa cctacccacg cttgcaacgc   960
ggacgtatgg cctggctgtt aatgcaggaa atatcgcaag gcaatcgtga gccgcatgtg  1020
ttgcaggcat tccggggact ggaaggtgac ctgggctacg gcatgttgct ctcccgctat  1080
gcgccggata tgaatcatgt cacagccgca cagtaccagg cggcgatgcg tggcgcgata  1140
cctcaggttg cgccggtatt ctggagtttc gcatcatgg tgggctgtgg ttccctgctg  1200
ctactggtga tgctgattgc gcttgtccag acgctgcgtg gcaaaatcga ccagcatcgc  1260
tgggtgctga aaatggcgct ctggagtttg ccgttgccgt ggattgcgat tgaagccggg  1320
tggtttatga ccgagtttgg tcgtcagccg tgggcgatac aggacatctt accgacatac  1380
tccgcgcact ccgctttaac cacaggacaa ctggctttct cactgatcat gatcgtaggg  1440
ctttacaccc tgttcttaat cgccgaagtc tacctgatgc agaaatatgc ccgtctgggg  1500
ccgagcgcga tgcagagtga acaaccgacg cagcaacagg ggtaa                 1545

<210> SEQ ID NO 8
<211> LENGTH: 1137
<212> TYPE: DNA
<213> ORGANISM: Escherichia coli
```

<400> SEQUENCE: 8

```
atgtttgatt atgaaacatt gcgcttcatc tggtggctgc tgattggcgt gatcctggtg      60
gtctttatga tctccgacgg atttgacatg gggatcggct gtctgctgcc gctggtggcg     120
cgtaatgatg atgaacgccg gatagtgata aacagcgttg gtgcacactg gaaggcaac      180
caggtctggt tgatcctcgc tggtggggca ttatttgccg cctggcccag agtgtatgca     240
gcggcgtttt ccggctttta tgtggcgatg atcctggtgc tgtgctcact gttcttccgc     300
ccgctggcct ttgattatcg cggaaaaatc gccgatgcac gctggcgtaa aatgtgggac     360
gccggtctgg tcatcggcag tctggtgccg cggtagtct tcggtatcgc cttcggcaac     420
ttgttgctcg gcgtgccgtt tgccttcaca ccgcaattac gcgtggagta tctcggcagc     480
ttctggcaac tgctgacgcc attccctta tgtgcggat tgctcagcct tgggatggtg      540
atttttgcaag gtggcgtctg gttacaactg aaaactgttg gtgtgattca tctgcgttca    600
cagctggcga ccaaacgcgc tgcactgttg gtgatgctgt gcttttttgct ggcgggttac    660
tggctgtggg tcggtattga tggctttgta ctgctcgccc aggatgctaa cggtccttcc    720
aatccgttaa tgaaactggt ggcagtgcta cctggtgcct ggatgaataa ttttgtcgag    780
tcgcccgttt tgtggatctt cccgctgctg ggattcttct gcccattgct gacggtgatg    840
gcgatttatc gtggtcgccc gggttgggga ttttgatgg catcattgat gcaatttggc    900
gtgattttca cggcaggcat cacgctgttc cctttgtca tgccgtcaag cgtgagtccg    960
atctccagcc tgacgttgtg ggacagtact tccagtcagc tgacgctgag cattatgttg   1020
gtaatcgtgc tgatatttt gcccattgtg ttgctctaca ctctctggag ctactacaaa   1080
atgtgggggc gcatgacaac agaaactctc cgccgtaacg aaaacgagtt gtactaa      1137
```

<210> SEQ ID NO 9  
<211> LENGTH: 315  
<212> TYPE: DNA  
<213> ORGANISM: Escherichia coli

<400> SEQUENCE: 9

```
atgcttaccg taatcgcaga aatccgtact cgtcctggtc aacatcaccg tcaggcggta      60
ttggatcagt ttgctaaaat cgttccaacc gtactgaaag aagaaggttg ccacggctat     120
gcgccaatgg tggattgcgc agctggcgtg agtttccagt ctatggcacc ggattctatc    180
gtgatgattg agcagtggga aagcatcgcg catcttgaag cgcatctgca aaccccgcac    240
atgaaggcgt atagcgaagc cgtaaaaggt gacgtgctgg agatgaatat ccgtattctg    300
cagccaggga tttaa                                                     315
```

<210> SEQ ID NO 10  
<211> LENGTH: 315  
<212> TYPE: DNA  
<213> ORGANISM: Escherichia coli

<400> SEQUENCE: 10

```
atgcttaccg taatcgcaga aatccgtact cgtcctggtc aacatcaccg tcaggcggta      60
ttggatcagt ttgctaaaat cgttccaacc gtactgaaag aagaaggttg ccacggctat     120
gcgccaatgg tggattgcgc agctggcgtg agtttccagt ctatggcacc ggattctatc    180
gtgatgattg agcagtggga aagcatcgcg catcttgaag cgcatctgca aaccccgcac    240
atgaaggcgt atagcgaagc cgtaaaaggt gacgtgctgg agatgaatat ccgtattctg    300
cagccaggga tttaa                                                     315
```

<210> SEQ ID NO 11
<211> LENGTH: 582
<212> TYPE: DNA
<213> ORGANISM: Escherichia coli

<400> SEQUENCE: 11

```
atgtcattcg aattacctgc actaccatat gctaaagatg ctctggcacc gcacatttct      60
gcggaaacca tcgagtatca ctacggcaag caccatcaga cttatgtcac taacctgaac     120
aacctgatta aggtaccgc gtttgaaggt aaatcactgg aagagattat tcgcagctct     180
gaaggtggcg tattcaacaa cgcagctcag gtctggaacc atactttcta ctggaactgc     240
ctggcaccga acgccggtgg cgaaccgact ggaaaagtcg ctgaagctat cgccgcatct     300
tttggcagct tgccgatttt caaagcgcag tttactgatg cagcgatcaa aaactttggt     360
tctggctgga cctggctggt gaaaaacagc gatggcaaac tggctatcgt ttcaacctct     420
aacgcgggta ctccgctgac caccgatgcg actccgctgc tgaccgttga tgtctgggaa     480
cacgcttatt acatcgacta tcgcaatgca cgtcctggct atctggagca cttctgggcg     540
ctggtgaact gggaattcgt agcgaaaaat ctcgctgcat aa                         582
```

<210> SEQ ID NO 12
<211> LENGTH: 80
<212> TYPE: DNA
<213> ORGANISM: Artificial Sequence
<220> FEATURE:
<223> OTHER INFORMATION: Synthetic

<400> SEQUENCE: 12

```
tgtgccactg acgctcggta tggcgttcct gctggccatt atggaaacgg tctacgtcct      60
gtgtaggctg gagctgcttc                                                  80
```

<210> SEQ ID NO 13
<211> LENGTH: 80
<212> TYPE: DNA
<213> ORGANISM: Artificial Sequence
<220> FEATURE:
<223> OTHER INFORMATION: Synthetic

<400> SEQUENCE: 13

```
tacagagagt gggtgttacg ttcaatatct tctttggtga tacgaccgaa cattttccag      60
attccgggga tccgtcgacc                                                  80
```

<210> SEQ ID NO 14
<211> LENGTH: 80
<212> TYPE: DNA
<213> ORGANISM: Artificial Sequence
<220> FEATURE:
<223> OTHER INFORMATION: Synthetic

<400> SEQUENCE: 14

```
atgagactca ggaaatacaa taaaagtttg ggatggttgt cattatttgc aggcactgta      60
gtgtaggctg gagctgcttc                                                  80
```

<210> SEQ ID NO 15
<211> LENGTH: 80
<212> TYPE: DNA
<213> ORGANISM: Artificial Sequence
<220> FEATURE:
<223> OTHER INFORMATION: Synthetic

```
<400> SEQUENCE: 15
ttagtgcatc atcatgttgt agttgaggtt ccacataatc cagatggagc ctacaaccag    60
attccgggga tccgtcgacc                                                80

<210> SEQ ID NO 16
<211> LENGTH: 80
<212> TYPE: DNA
<213> ORGANISM: Artificial Sequence
<220> FEATURE:
<223> OTHER INFORMATION: Synthetic

<400> SEQUENCE: 16
atgtgggatg tcattgattt atcgcgctgg cagtttgctc tgaccgcgct gtatcacttt    60
gtgtaggctg gagctgcttc                                                80

<210> SEQ ID NO 17
<211> LENGTH: 80
<212> TYPE: DNA
<213> ORGANISM: Artificial Sequence
<220> FEATURE:
<223> OTHER INFORMATION: Synthetic

<400> SEQUENCE: 17
ttagtacaac tcgttttcgt tacggcggag agtttctgtt gtcatgcgcc cccacatttt    60
attccgggga tccgtcgacc                                                80

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18
aaagaattaa ggtcaaccg                                                 19

<210> SEQ ID NO 19
<211> LENGTH: 25
<212> TYPE: DNA
<213> ORGANISM: Artificial Sequence
<220> FEATURE:
<223> OTHER INFORMATION: Synthetic

<400> SEQUENCE: 19
cgcccgcagg gggcgcttgt ccatt                                          25

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
ataacgccct tttgcaacag                                                20

<210> SEQ ID NO 21
<211> LENGTH: 25
<212> TYPE: DNA
<213> ORGANISM: Artificial Sequence
<220> FEATURE:
<223> OTHER INFORMATION: Synthetic

<400> SEQUENCE: 21
```

```
gttaaacaca aacccgacg ccaca                                          25
```

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22

```
gcttagcgag gtatgtcagt                                               20
```

<210> SEQ ID NO 23
<211> LENGTH: 25
<212> TYPE: DNA
<213> ORGANISM: Artificial Sequence
<220> FEATURE:
<223> OTHER INFORMATION: Synthetic

<400> SEQUENCE: 23

```
tgtcagatat gaaaagcgga aacat                                         25
```

<210> SEQ ID NO 24
<211> LENGTH: 60
<212> TYPE: DNA
<213> ORGANISM: Artificial Sequence
<220> FEATURE:
<223> OTHER INFORMATION: Synthetic

<400> SEQUENCE: 24

```
atgcttaccg taatcgcaga aatccgtact cgtcctggtc gtgtaggctg gagctgcttc   60
```

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25

```
ttaaatccct ggctgcagaa tacggatatt catctccagc attccgggga tccgtcgacc   60
```

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26

```
ccgacattta tcgctaatga                                               20
```

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27

```
gttgcaagag aaaggcgaca                                               20
```

ESCHERICHIA COLI METABOLIC ENGINEERING OXYGEN INDEPENDENT PLATFORM STRAINS AND METHODS OF USE THEREOF

This application claims priority to U.S. provisional Application Ser. No. 61/363,863, filed Jul. 13, 2010, herein incorporated by reference in its entirety for all purposes.

A Sequence Listing has been submitted in an ASCII text file named "17137.revised_ST25.txt," created on Feb. 19, 2014, consisting of 19 kilobytes, the entire content of which is herein incorporated by reference.

This invention was made with government support under grant GM062791, awarded by the US National Institutes of Health. The government has certain rights in the invention.

FIELD OF THE INVENTION

The invention relates to transgenic *Escherichia coli* cells that have substantially the same level of growth in oxic conditions as the level of growth in anoxic conditions of wild type *E. coli*, and that are capable of converting glucose to D-lactate and/or amino acid and/or 2,3-butanediol (2,3-BDO) under one or both of oxic conditions and anoxic conditions.

BRIEF DESCRIPTION OF THE DRAWINGS

FIG. 21: DNA sequence of the following *Eschericia coli* genes (A) cydA gene (SEQ ID NO:01), (B) cydB gene (SEQ ID NO:02), (C) cyoA gene (SEQ ID NO:03), (D) cyoB gene (SEQ ID NO:04), (E) cyoC gene (SEQ ID NO:05), (F) cyoD gene (SEQ ID NO:06), (G) cbdA gene (SEQ ID NO:07), (H) cbdB gene (SEQ ID NO:08), (I) ygiN gene (SEQ ID NO:09), (J) sodA gene (SEQ ID NO:10), and (K) sodB gene (SEQ ID NO:11).

SUMMARY OF THE INVENTION

Figure 1:
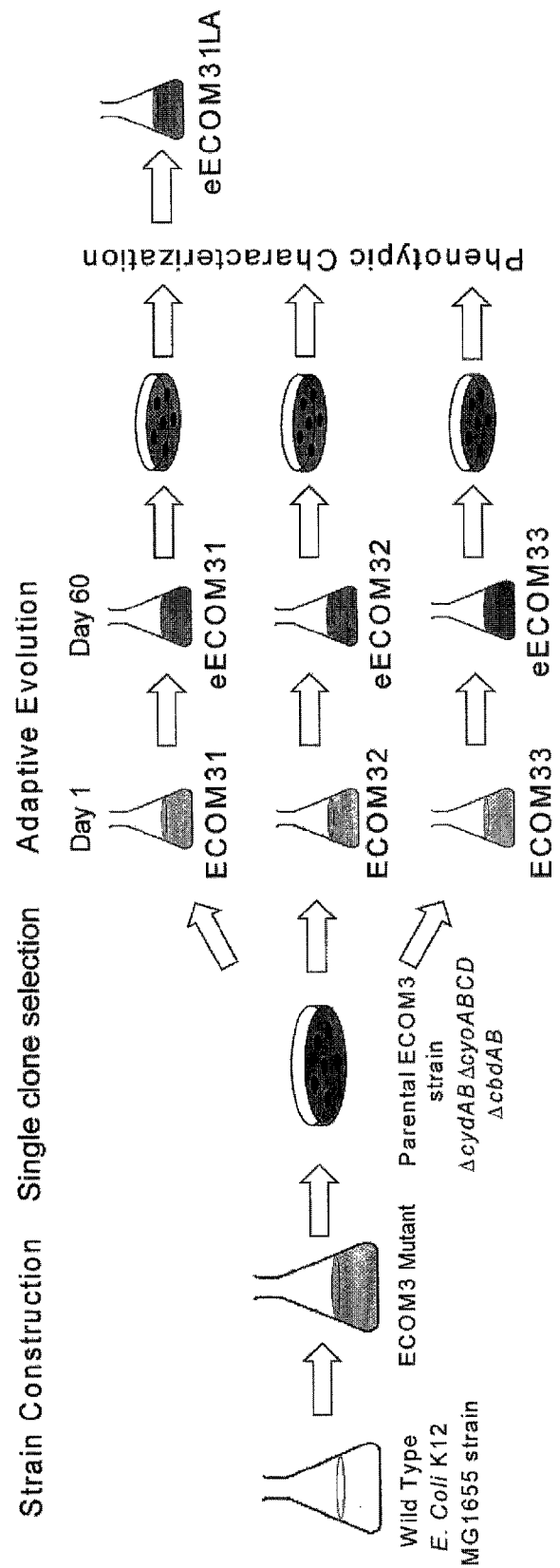
FIG. 1: The overall experimental design, and nomenclature. Wild type *E. coli* K12 MG1655 strain was converted to parental ECOM3 strain through a series of genetic manipulations. A single clone (colony) of ECOM3 was isolated from the solid media, and subjected to adaptive evolution (ECOM31, ECOM32, ECOM33) resulting in three end-point populations (eECOM31, eECOM32, eECOM33; 'e'-indicates the evolved strain). Following the phenotypic characterization the strain with the highest lactate yield was identified (eECOM31LA).

The invention provides a transgenic *Escherichia coli* cell comprising a deletion of at least one of cydA gene (SEQ ID NO:01), cydB gene (SEQ ID NO:02), cyoA gene (SEQ ID NO:03), cyoB gene (SEQ ID NO:04), cyoC gene (SEQ ID NO:05), cyoD gene (SEQ ID NO:06), cbdA gene (SEQ ID NO:07), cbdB gene (SEQ ID NO:08), and ygiN gene (SEQ ID NO:09), wherein the transgenic *Escherichia coli* cell a) has substantially the same level of growth in oxic conditions as the level of growth in anoxic conditions of *Escherichia coli* that comprises the cydA gene, the cydB gene, the cyoA gene, the cyoB gene, the cyoC gene, the cyoD gene, the cbdA gene, the cbdB gene, the and ygiN gene, and b) is capable of converting glucose to D-lactate under one or both of oxic conditions and anoxic conditions. In one embodiment, the transgenic cell has substantially the same level of growth in M9 minimal essential media that (a) comprises a carbon source consisting of glucose, and (b) lacks amino acids Ala, Arg, Asn, Asp, Cys, Glu, Gln, Gly, His, Ile, Leu, Lys, Met, Phe, Pro, Ser, Thr, Trp, Tyr, and Val, as *Escherichia coli* that comprises the cydA gene, the cydB gene, the cyoA gene, the cyoB gene, the cyoC gene, the cbdA gene, and the cbdB gene. In another embodiment, the transgenic cell has reduced oxygen uptake in oxic conditions compared to *Escherichia coli* that comprises the cydA gene, the cydB gene, the cyoA gene, the cyoB gene, the cyoC gene, the cyoD gene, the cbdA gene, and the cbdB gene. In a further embodiment, the transgenic cell produces increased levels of D-lactic acid, when cultured in the presence of glucose as substrate, under one or both of oxic conditions and anoxic conditions compared to D-lactic acid levels produced by *Escherichia coli* that comprises the cydA gene, the cydB gene, the cyoA gene, the cyoB gene, the cyoC gene, the cyoB gene, the cbdA gene, and the cbdB gene. In yet another embodiment, the D-lactic acid is produced in oxic conditions. In a further embodiment, the transgenic cell produces altered levels of acetate, when cultured in the presence of glucose as substrate, under one or both of oxic conditions and anoxic conditions compared to acetate levels produced by *Escherichia coli* that comprises cydA gene, the cydB gene, the cyoA gene, the cyoB gene, the cyoC gene, the cyoD gene, the cbdA gene, and the cbdB gene. In yet another embodiment, the transgenic cell has increased expression of at least one of the ygiN gene, sodA gene (SEQ ID NO:10), and sodB gene (SEQ ID NO:11) compared to *Escherichia coli* that comprises the cydA gene, the cydB gene, the cyoA gene, the cyoB gene, the cyoC gene, the cyoD gene, the cbdA gene, and the cbdB gene. In another embodiment, the transgenic *Escherichia coli* further comprises a deletion of at least one of the ygiN gene, sodA gene (SEQ ID NO: 10) and sodB gene (SEQ ID NO:11).

The invention also provides a cell derived from any one of the transgenic cells described herein Also provided by the invention is a method for producing an *Escherichia coli* cell that produces D-lactic acid under oxic conditions, comprising a) deleting at least one of cydA gene (SEQ ID NO:01), cydB gene (SEQ ID NO:02), cyoA gene (SEQ ID NO:03), cyoB gene (SEQ ID NO:04), cyoC gene (SEQ ID NO:05), cyoD gene (SEQ ID NO:06), cbdA gene (SEQ ID NO:07), cbdB gene (SEQ ID NO:08), and ygiN gene (SEQ ID NO:09) from the genome of an *Escherichia coli* cell to produce a transgenic *Escherichia coli* cell, and b) culturing the transgenic *Escherichia coli* cell to produce a cultured *Escherichia coli* cell, wherein the culturing is in M9 minimal essential media that i) comprises a carbon source consisting of glucose, and ii) lacks amino acids Ala, Arg, Asn, Asp, Cys, Glu, Gln, Gly, His. Ile, Leu, Lys, Met, Phe, Pro, Ser, Thr, Trp, Tyr, and Val. In one embodiment, the method further comprises purifying the cultured *Escherichia coli* cell.

The invention also provides a method for producing D-lactic acid comprising culturing any one or more of the transgenic *Escherichia coli* described herein in M9 minimal essential medium that contains glucose, wherein the culturing is under conditions for production of D-lactic acid. In one embodiment, the conditions are selected from the group consisting of oxic conditions and anoxic conditions. In preferred embodiment, the conditions are oxic conditions. In a particular embodiment, the method further comprises purifying the produced D-lactic acid. In a further embodiment of the invention's method, the *Escherichia coli* cell is selected from the group consisting of ECOM3, ECOM31, ECOM32, ECOM33, ECOM4, and ECOM4LA. In yet another embodiment, the *Escherichia coli* cell is derived from any one or more of the transgenic cells described herein. In a particular embodiment, the *Escherichia coli* cell is ECOM4LA.

The invention also provides a method for producing an amino acid comprising culturing any one or more of the transgenic *Escherichia coli* cells described herein in M9 minimal essential medium that contains glucose, wherein the culturing is under conditions for production of an amino acid.

The invention also provides a method for producing 2,3-butanediol (2,3-BDO) comprising culturing any one or more of the transgenic *Escherichia coli* cells described herein in M9 minimal essential medium that contains glucose, wherein the culturing is under conditions for production of 2,3-BDO.

The invention also provides transgenic *Escherichia coli* cells comprising a mutation in cydA, and/or cydB genes, cyoA, cyoB, cyoC, cyoD genes, and cbdA, cbdB (also known as appB, appC) genes, wherein the mutation reduces (preferably, but not necessarily, by 100%) the cytochrome oxydase activity of a protein encoded by cydA, cydB genes, cyoA, cyoB, cyoC, cyoD genes, and cbdA, cbdB genes. In a preferred embodiment, the mutation is a deletion of the cydA and cydB genes, cyoA, cyoB, cyoC, cyoD genes, and cbdA, cbdB genes. In another embodiment, the transgenic *Escherichia coli* cell, which comprises a deletion of cydA, cydB genes, cyoA, cyoB, cyoC, cyoD genes and cbdA, cbdB genes, a) has substantially the same level of growth in oxic conditions as the level of growth in anoxic conditions of *E. coli* that lacks said deletion of cydA, cydB genes, cyoA, cyoB, cyoC, cyoD genes, and cbdA, cbdB genes, and b) is capable of converting glucose to D-lactate under one or both of oxic conditions and anoxic conditions.

In another embodiment, the transgenic *Escherichia coli* cell, which comprises a deletion of cydA, cydB genes, cyoA, cyoB, cyoC, cyoD genes, and cbdA, cbdB genes, and ygiN gene a) has substantially the same level of growth in oxic conditions as the level of growth in anoxic conditions of *E. coli* that lacks said deletion of cydA, cydB genes, cyoA, cyoB, cyoC, cyoD genes, and cbdA, cbdB genes, and ygiN gene, and b) is capable of converting glucose to D-lactate under one or both of oxic conditions and anoxic conditions, and c) is presented with a significantly reduced oxygen uptake rate, which is nearly 50 times lower than the oxygen uptake rate of the *Escherichia coli* cell without deletions of cydA, cydB genes, cyoA, cyoB, cyoC, cyoD genes, and cbdA, cbdB genes, and ygiN gene.

DEFINITIONS

"Oxic" and "aerobic" are used interchangeably to refer to the presence of oxygen.

"Anoxic" and "anaerobic" are used interchangeably to refer to reduced levels of oxygen, including, but not limited to, complete absence of oxygen.

"M9 minimal essential media" is a medium for culturing cells (Fischer E, Sauer U. "Metabolic flux profiling of *Escherichia coli* mutants in central carbon metabolism using GC-MS." Eur J Biochem. 2003 March; 270(5):880-91. PMID: 12603321; Sambrook, J., and D. W. Russell. 2001. Molecular Cloning: A Laboratory Manual 3ed, vol. A2.2. Cold Spring Harbor Laboratory Press, New York), and is commercially available from AMRESCO (Ohio, USA). M9 minimum medium contains salts and trace elements as follows (with exemplary commercial sources for individual components).

| M9 salts (per liter): | |
|---|---|
| 0.8 g | $NH_4Cl$ (Sigma Aldrich) |
| 0.5 g | NaCl (Sigma Aldrich) |
| 7.52 g | $Na_2HPO_4$ (Sigma Aldrich) |
| 3.0 g | $KH_2PO_4$ (Sigma Aldrich) |
| 2 mL | $MgSO_4$ (1M) (Sigma Aldrich) |
| 1 mL | $CaCl_2$ (100 mM) (Sigma Aldrich) |
| 0.2-0.4% | Glucose (Sigma Aldrich) |
| Trace elements (per liter): | |
| 0.1667 g | $FeCl_3 \cdot 6H_2O$ (Sigma Aldrich) |
| 0.0018 g | $ZnSO_4 \cdot 7H_2O$ (Sigma Aldrich) |
| 0.0012 g | $CuCl_2 \cdot 2H_2O$ (Sigma Aldrich) |
| 0.0012 g | $MnSO_4 \cdot H_2O$ (Sigma Aldrich) |
| 0.0018 g | $CoCl_2 \cdot 6H_2O$ (Sigma Aldrich) |
| 0.2225 g | $Na_2EDTA \cdot 2H_2O$ (Sigma Aldrich) |
| 1 ml | Thiamine HCl (1 mg/ml) (Sigma Aldrich) |

The term "transgenic" when used in reference to a cell whose genome has been manipulated by any molecular biological technique, including, for example, the introduction of a transgene, homologous recombination, knockin of a gene, and/or knockout of a gene.

The term "derived" as used herein when in reference to a cell that is derived from a parent cell means that the derived cell is a progeny of and/or is descended from the parent cell. Derived cells include cells that have been subjected to chemical and/or biological manipulations including, but not limited to, genetic manipulation by nucleotide substitution, addition, insertion, and deletion, cell culture (such as under oxic and/or anoxic conditions), etc.

The terms "purified," "isolated," and grammatical equivalents thereof as used herein, refer to the reduction in the amount of at least one undesirable component (such as cell type, protein, and/or nucleic acid sequence) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in "enrichment," i.e., an increase in the amount of a desirable cell type, protein and/or nucleic acid sequence in the sample.

The terms "mutation" and "modification" refer to a deletion, insertion, or substitution. A "deletion" is defined as a change in a nucleic acid sequence or amino acid sequence in which one or more nucleotides or amino acids, respectively, is absent. An "insertion" or "addition" is that change in a nucleic acid sequence or amino acid sequence that has resulted in the addition of one or more nucleotides or amino acids, respectively. An insertion also refers to the addition of any synthetic chemical group, such as those for increasing solubility, dimerization, binding to receptors, binding to substrates, resistance to proteolysis, and/or biological activity of the amino acid sequence. A "substitution" in a nucleic acid sequence or an amino acid sequence results from the replacement of one or more nucleotides or amino acids, respectively, by a molecule that is a different molecule from the replaced one or more nucleotides or amino acids. For example, a nucleic acid may be replaced by a different nucleic acid as exemplified by replacement of a thymine by a cytosine, adenine, guanine, or uridine. Alternatively, a nucleic acid may be replaced by a modified nucleic acid as exemplified by replacement of a thymine by thymine glycol. Substitution of an amino acid may be conservative or non-conservative. A "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) may be conservatively substituted for glutamic acid (glutamate) as both are acidic, charged (hydrophilic) amino acids. Also, lysine, arginine, and histidine may be conservatively substituted one for the other since each is a basic, charged (hydrophilic) amino acid. "Non-conservative substitution" is a substitution other than a conservative substitution. Guidance in determining which and how many amino acid residues may be substituted, inserted or deleted without abolishing biological and/or immunological activity may be found using computer programs well known in the art, for example, DNAStar™ software.

The terms "change" and/or "alter" refers to a quantitative increase or decrease.

The terms "increase," "elevate," "raise," and grammatical equivalents (including "higher," "greater," etc.) when in reference to the level of any molecule (e.g., oxygen, lactic acid, acetate, nucleic acid sequence such as cydA gene, cyoB genes, cyoA gene, cyoB gene, cyoC gene, cyoD gene, cbdA gene, cbdB gene, ygiN gene, sodA gene, and sodB gene, amino acid sequence such as polypeptides encoded by the cydA gene, cyoB genes, cyoA gene, cyoB gene, cyoC gene, cyoD gene, cbdA gene, cbdB gene, ygiN gene, sodA gene, and sodB gene), cell, and/or phenomenon (e.g., conversion of glucose to lactate, conversion of glucose to acetate, conversion of glucose to 2,3-BDO, cell proliferation, cell growth, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, mean that the quantity of the molecule, cell and/or phenomenon in the first sample is higher than in the second sample (or in a treated patient) by any amount that is statistically significant using any art-accepted statistical method of analysis. In one embodiment, the quantity of molecule, cell, and/or phenomenon in the first sample is higher by any numerical percentage, such as at least 10% greater than, at least 25% greater than, at least 50% greater than, at least 75% greater than, and/or at least 90% greater than the quantity of the same molecule, cell and/or phenomenon in a second sample. In yet a further embodiment, the quantity of molecule, cell, and/or phenomenon in the first sample is higher by any numerical amount from 5 fold to 1000 fold, including from 5 fold to 500 fold, 10 fold to 400 fold, from 20 fold to 300 fold, from 30 fold to 200 fold, from 40 fold to 200 fold, from 50 fold to 200 fold.

The terms "decrease," "reduce," "inhibit," "diminish," "suppress," and grammatical equivalents (including "lower," "smaller," etc.) when in reference to the level of any molecule (e.g., oxygen, lactic acid, acetate, nucleic acid sequence such as cydA gene, cyoB genes, cyoA gene, cyoB gene, cyoC gene, cyoD gene, cbdA gene, cbdB gene, ygiN gene, sodA gene, and sodB gene, amino acid sequence such as polypeptides encoded by the cydA gene, cyoB genes, cyoA gene, cyoB gene, cyoC gene, cyoD gene, cbdA gene, cbdB gene, ygiN gene, sodA gene, and sodB gene), cell, and/or phenomenon (e.g., conversion of glucose to lactate, conversion of glucose to acetate, conversion of glucose to 2,3-BDO, cell proliferation, cell growth, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, mean that the quantity of molecule, cell, and/or phenomenon in the first sample is lower than in the second sample by any amount that is statistically significant using any art-accepted statistical method of analysis. In one embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in a second sample.

The term "substantially the same" when in reference to the level of any molecule (e.g., oxygen, lactic acid, acetate, nucleic acid sequence such as cydA gene, cyoB genes, cyoA gene, cyoB gene, cyoC gene, cyoD gene, cbdA gene, cbdB gene, ygiN gene, sodA gene, and sodB gene, amino acid sequence such as polypeptides encoded by the cydA gene, cyoB genes, cyoA gene, cyoB gene, cyoC gene, cyoD gene, cbdA gene, cbdB gene, ygiN gene, sodA gene, and sodB gene), cell, and/or phenomenon (e.g., conversion of glucose to lactate, conversion of glucose to acetate, conversion of glucose to 2,3-BDO, cell proliferation, cell growth, cell death, cell apoptosis, cell viability, cell survival, binding to a molecule, affinity of binding, expression of a nucleic acid sequence, transcription of a nucleic acid sequence, enzyme activity, etc.) in a first sample relative to a second sample, means that the difference in quantity of measurement or phenomenon in the first sample compared to the second sample is not statistically significant. In one embodiment, the difference in quantity of measurement or phenomenon between the first and second samples is less than 10%. Thus, in one embodiment, the quantity of molecule, cell and/or phenomenon in the first sample is from 90% to 100% (e.g., 90%, 91%, 92%, 93%, 94%, 95%, 96%, 97%, 98%, 99%, and 100%) of the quantity in the second sample.

The term "cydAB gene" refers to cydA gene (such as SEQ ID NO:01) and cydAB gene (such as SEQ ID NO:02).

The term "cyoABCD gene" refers to cyoA gene (such as SEQ ID NO:03), cyoB gene (such as SEQ ID NO:04), cyoC gene (such as SEQ ID NO:05), and cyoD gene (such as SEQ ID NO:06).

The term "cbdAB gene" refers to cbdA gene (such as SEQ ID NO:07) and cbdB gene (such as SEQ ID NO:08).

The term "ygiN gene" refers to ygiN gene (such as SEQ ID NO:09)

The term "sodAB gene" refers to sodA gene (such as SEQ ID NO:10) and sodB gene (such as SEQ ID NO:11).

BRIEF DESCRIPTION OF THE INVENTION

The invention provides transgenic *Escherichia coli* cells comprising a mutation in cydAB gene, and/or cyoABCD gene, and/or cbdAB gene, and/or ygiN gene, wherein the mutation reduces (preferably, but not necessarily, by 100%) the cytochrome oxidase activity of a protein encoded by cydAB gene, and/or cyoABCD gene, and/or cbdAB gene, and/or ygiN gene. In a preferred embodiment, the mutation is a deletion of the cydAB gene, cyoABCD gene, and cbdAB gene. In another embodiment, the mutation is a deletion of the cydAB gene, cyoABCD gene, cbdAB gene, and ygiN gene. In another embodiment, the transgenic *Escherichia coli* cell, which comprises a deletion of cydAB gene, and/or cyoABCD gene, and/or cbdAB gene, and/or ygiN gene a) has substantially the same level of growth in oxic conditions as the level of growth in anoxic conditions of *Escherichia coli* that lacks said deletion of cydAB gene, and/or cyoABCD gene, and/or cbdAB gene, and/or ygiN gene, and b) is capable of converting glucose to D-lactate and/or amino acid and/or 2,3-butanediol (2,3-BDO) under one or both of oxic conditions and anoxic conditions.

It has been reported that simultaneous deletion of cyd and cyo operons has resulted in a significant decrease, but not elimination, of oxygen uptake (4). However, no secretion analysis or other physiological characterization of this mutant strain has been reported (4,5).

Current state of lactic acid production: In the past, only lactic acid bacteria such as *L. lactis* were used to produce D-(−) and L-(+) lactic acid. However, recently a genetically modified *E. coli* was shown to produce lactic acid with yields ranging between 85% and 95% from glucose (6). Current production requires anaerobic cultivation (7) or dual phase aerobic—anaerobic cultivation (8).

Due to the inability to utilize molecular oxygen both strains can be used as metabolic engineering platforms. This invention enables the use of adaptive evolution as a means for optimizing the metabolic engineering design under oxic growth conditions. Metabolic engineering designs implemented into the platform strains can be optimized under oxic growth conditions eliminating the burden of maintaining a strict anoxic environment.

Furthermore, both strains can be used for overproduction of D-lactic acid from glucose via aerobic fermentation. D-Lactate yields are close to 80% and over 95% for ECOM3 and ECOM4 strains respectively.

Additionally both strais can be used for overproduction of L-lactic acid from glucose after additional genetic modification. L-lactate yields are close to 80% and over 95% for genetically modified ECOM3 and ECOM4 strain respectively. Genetic modification referred herein is comprised of an additional gene introduced in the transgenic *E. coli* cell harboring following deletions, the cydA, cydB genes, cyoA, cyoB, cyoC, cyoD genes, and cbdA, cbdB genes, ygiN gene, that is capable of producing a protein capable of converting pyruvate to L-lactic acid (i.e L-lactate dehydrogenase from the *L. lactis*).

Moreover both strais can be used for overproduction of L-alanine from glucose after additional genetic modification. L-alanine yields are close to 80% and over 95% for genetically modified ECOM3 and ECOM4 strain respectively. Genetic modification referred herein is comprised of an additional gene introduced in the transgenic *E. coli* cell harboring following deletions in cydA, cydB genes, cyoA, cyoB, cyoC, cyoD genes, and cbdA, cbdB genes, ygiN gene, that is capable of producing a protein capable of converting pyruvate to L-alanine (i.e NADH-dependant alanine dehydrogenase (dadA from *E. coli*).

Furthermore both strais can be used for overproduction of 2,3-butanediol (2,3-BDO) from glucose after additional genetic modification. Theretical 2,3-BDO yields are close to 65% for genetically modified ECOM3 and ECOM4 strain respectively. Genetic modification referred herein is comprised of an additional genes introduced in the transgenic *E. coli* cell harboring following deletions in cydA, cydB genes, cyoA, cyoB, cyoC, cyoD genes, and cbdA, cbdB genes, ygiN gene, that are capable of producing proteins capable of converting two molecules of pyruvate to 2,3-BDO.

In short, the inability to utilize molecular oxygen is one of the unique properties of the invention. This advantage can enable adaptive evolution of the metabolic engineering designs under oxic growth conditions. Usually metabolic engineering designs require an anoxic environment for optimization and implementation; however, sustainability of an anoxic environment during long term adaptive evolution is a challenging task. The use of the invention as a platform stain allows for the optimization of anaerobic designs under oxic conditions, which are significantly easier to maintain.

Additionally, the invention enables the overproduction of lactic acid at 80% and 97% efficiency for both strains respectively, under both aerobic and anaerobic growth conditions. These findings are highlighted in the manuscript ("Aerobic Fermentation of D-Glucose by an Evolved Cytochrome Oxidase Deficient *Escherichia coli* Strain") (1). Among other significant phenotypic changes, the reduced oxygen uptake, observed in ECOM3 and ECOM4 strains, provides novel and valuable industrial advantages such as reduced mixing and reduced aeration rate leading to a significant reduction in energy investment during the production of lactic acid.

Briefly, some of the novel properties of the invention include: Reduced oxygen dependency of both strains allows the invention to be used as a platform strain for optimization of the metabolic engineering designs, natural overproduction of lactic acid through coupling of production to growth. The removal of the electron transfer chain (cytochrome complexes) leads to the redirection of the central metabolism towards the lactate secretion when grown on glucose as the carbon source. The overproduction of lactate is triggered by the need of the recycling of the NADH to NAD. Glucolysis is known for production of two NADH as a result of oxidation of one molecule of glucose to pyruvate. Due to the lack of an electron transfer chain and the inability to accept electrons from NADH dehydrogenase, the recycling of the NADH to NAD is ensured by further oxidation of pyruvate to lactate.

Lactate yield of over 80% and close to 97% was demonstrated by the exemplary strains described herein.

The glucose uptake rates observed in the evolved ECOM3 and ECOM4 populations were significantly higher than previously reported in the scientific literature.

Genetic amenability of the evolved strains was demonstrated by homologous recombination using the lambda Red recombinase system (2, 3)

The complete removal of three cytochrome oxydases in *Escherichia coli* has not been shown before.

Some of the utilities are described as follows. One of the uses of the invention is an adaptive evolution platform strain. Metabolic engineering design (i.e. collection of heterogeneous genes and/or a number of gene deletions) is preferably implemented in the ECOM3 or ECOM4 strain. Once the design is implemented, the resulted strain is preferably subjected to aerobic adaptive evolution. Adaptation can be conducted through batch-to-batch daily passage to impose the growth selective pressure. Daily passage ensures the enrichment of the faster growing mutants within the original population. It has been shown that under the growth selective pressure the fitness of the population increases after the first 250 generations (9). The increase in growth rate will lead to an increase in production rate for growth-coupled designs. Once the increase in growth rate is observed, the strain design is preferably physiologically characterized to determine the design's production potential.

The invention provides, in one embodiment, a bacterial strain capable of fermenting glucose to D-lactate under oxic of anoxic growth conditions. The following conditions are preferred (1):
Batch Fermentation (Aerobic Flask Setup):
Media: M9 minimal media supplemented with 2 g/L glucose as a sole carbon source (can be supplemented with kanamysin antibiotic)
Volume: 250 ml in a 500 ml in an Erlenmyer flask
Aeration: open to the air (stirring speed ~1000 rpm)
Temperature: 37° C.
Fermentation time: 6-8 hours
Batch Fermentation (Anaerobic Flask Setup):
Media: M9 minimal media supplemented with 2 g/L glucose as a sole carbon source (can be supplemented with kanamysin antibiotic)
Volume: 200 ml in a 250 ml in a Erlenmeyer flasks
Aeration: anaerobic* (stirring speed ~200 rpm)
Temperature: 37° C.
Fermentation time: 6-8 hours

*Anaerobic cultivation was conducted in 250 ml Erlenmeyer flasks with 200 ml of medium, sealed with rubber stoppers containing necessary inlet tubing. Anoxic conditions were achieved by continuous flashing of cultures with 95% $N_2$ 5% $CO_2$ gas mixture at flow rate of 1 ml/min.

The invention's strains can be used as an evolutionary platform for optimization of the anaerobic metabolic engineering designs. The majority of the metabolic engineering designs require anaerobic conditions for optimization (10). Anaerobic evolution requires strict control of the growth environment and can be challenging. Utilization of the ECOM3 or ECOM4 strain as a platform strain eliminates that challenge.

The exemplary ECOM3 and/or ECOM4 strains can be used for commercial production of D-lactic acid, which is a economically valuable commodity chemical. Lactic acid is used as a monomer for producing polylactic acid (PLA) which later has application as biodegradable plastic. This kind of plastic is a good substitute for conventional plastic produced from petroleum oil due to low emission of carbon dioxide that can contribute to global warming.

The ECOM3 strain has been generated, evolved (60 days), and characterized. During the genetic characterization of the ECOM3 strain we identified an enzyme that may account for the remaining oxygen uptake. The ygiN (quinol monooxygenase) gene has been removed from the ECOM3 strain leading to the development of the different strain (ECOM4). ECOM4 strain has been developed using the same parental strain that was used to generate the ECOM3 strain described herein. Initial phenotypic characteristics showed that the ECOM4 strain has no oxygen uptake and higher lactate yield then the ECOM3 strain. The ECOM4 strain has been characterized and evolved as well.

Phenotypic data for the ECOM3 and ECOM4 strains is presented in the below Examples.

EXPERIMENTAL

Example 1

Fermentation of glucose to D-lactic acid under aerobic growth condition by an evolved *E. coli* mutant deficient in three terminal oxidases is reported in this work. Cytochrome oxidases (cydAB, cyoABCD, cbdAB) were removed from the *E. coli* K12 MG1655 genome resulting in the ECOM3 (*E. coli* Cytochrome Oxidase Mutant) strain. Removal of cytochrome oxidases reduced the oxygen uptake rate of the knock-out strain by nearly 85%. Moreover, the knock-out strain was initially incapable of growing on M9 minimal media. After subjecting the ECOM3 strain to adaptive evolution on glucose M9 medium for 60 days, the growth rate equivalent to anaerobic wild type *E. coli* was achieved. Our findings demonstrate that three independently adaptively evolved ECOM3 populations acquired different phenotypes: one produced lactate as a sole fermentation product while the other two strains exhibited a mixed acid fermentation under oxic growth conditions with lactate remaining as the major product. The homofermenting strain showed the D-lactate yield of 0.8 g/g from glucose. Gene expression and in silico model-based analysis was employed to identify perturbed pathways and explain phenotypic behavior. Significant upregulation of ygiN and sodAB explain the remaining oxygen uptake that was observed in evolved ECOM3 strains. *E. coli* strains exemplified herein showed the ability to produce lactate as a fermentation product from glucose as well as undergo mixed-acid fermentation during aerobic (oxic conditions) growth.

*Escherichia coli* is one of the most commonly used host organisms for metabolic engineering and overproduction of metabolites due to its fast growth rate, amenability to genetic manipulation, and its ability to produce wide variety of anaerobic fermentation products such as organic acids. *E. coli* has also been extensively characterized with respect to its metabolic physiology (22) enabling the utilization of rational model-based engineering strategies (14, 16, 20, 21). Rational model-based approach to engineering *E. coli* that aims to couple specific metabolite overproduction to growth combined with adaptive evolution have shown promise for strain optimization (16, 17). For engineered strains that couple desirable byproduct secretion to growth, adaptation to higher growth rates has been shown to lead to the increased production of the product (16).

The anaerobic growth of E. coli is characterized by the formation of a number of reduced byproducts as a result of mixed-acid fermentation, the majority of the metabolic engineering designs rely on anoxic growth conditions. Maintenance of a strict anoxic condition is a challenging task and complicates the procedure of experimental adaptation.

The goal of the experiments described herein was to develop an E. coli strain that could show similar phenotypic behavior under both oxic and anoxic growth conditions. The resulting strain could be used as a platform strain in evolutionary engineering where long term laboratory evolution in aerobic conditions is used to optimize desirable phenotypic traits (16).

It has been reported that simultaneous deletion of cyd and cyo genes has resulted in a significant decrease, but not elimination, of oxygen uptake (5). However, no secretion analysis or other physiological characterization of this mutant strain has been reported (5, 28). Based on these results, we hypothesized that removal of all of three cytochrome oxidases would result in anaerobic growth characteristics even under oxic conditions. Moreover, we hypothesized activation of anaerobic pathways responsible for mixed acid fermentation as a means of NADH recycling, leading to the production of fermentation products aerobically.

Wild type E. coli strain (MG1655) was subjected to genetic manipulation and all active cytochrome oxidases were removed from its genome. The resulting ECOM3 (E. coli Cytochrome Oxidase Mutant) strain was subjected to adaptive evolution and phenotypic characterization through out the course of evolution. The experimental setup for the adaptive evolution of ECOM3 and the nomenclature used in this work are presented in FIG. 1. The three evolved populations were extensively characterized and results are presented.

Example 2

Materials and Methods Used for Generation of Example 1 Data

Strains and Media:

E. coli K12 MG1655 (ATCC: 700926), obtained from the American Type Culture Collection (Manassas, Va.), was used as a parent strain for all gene deletions in this work. During the gene deletion process the strains were cultured on Luria-Bertani medium supplemented with 50 µg/ml kanamycin and 100 µg/ml ampicillin when necessary. Evolution and phenotype assessments of the mutant strain were carried out using M9 minimal media (26) with glucose (2 g/l) as the carbon source containing $Na_2HPO_4 \cdot 7H_2O$ (6.8 g), $KH_2PO_4$ (3 g), NaCl (0.5 g), $NH_4Cl$ (1 g), $MgSO_4$ (2 mM), and $CaCl_2$ (0.1 mM) and trace elements (15). During the early stage of adaptive evolution minimal media was additionally supplemented with EZ supplements (Technova) containing the mixture of L-amino acids at following concentrations (numbers indicate milimolarity): Ala (0.8), Arg (5.2), Asn (0.4), Asp (0.4), Cys (0.1), Glu (0.6), Gln (0.6), Gly (0.8), His (0.2), Ile (0.4), Leu (0.8), Lys (0.4), Met (0.2), Phe (0.4), Pro (0.4), Ser (10.0), Thr (0.4), Trp (0.1), Tyr (0.2), Val (0.6), adenine, guanine, cytosine, and uracil (0.2 each), and thiamine, calcium pantothenate, p-aminobenzoic acid, p-hydroxybenzoic acid, and 2,3-dihydroxybenzoic acid (0.01 each) (23).

Generation of Mutant Strains:

All strains and plasmids used in this work are listed in Table 2. The Escherichia coli K-12 MG1655 (ECOM3 or E. coli Cytochrome Oxidase Mutant: ΔcydAB-cyoABCD-cbdAB) strain lacking three known cytochrome oxidases was generated by homologous recombination using the lambda Red recombinase system (6, 9) with primers listed in Table 5. In short, the gene to be deleted was replaced by a kanamycin gene flanked by FRT sites and the insert was removed with a FLP recombinase. The cydAB operon was removed first, followed by the cyoABCD operon and then the cbdAB. For the cbdAB operon deletion the resistance cassette was not removed with a FLP recombinase. In order to verify the genotype of all evolved mutants, colonies were isolated from solid media and tested with PCR. Primers used for deletion verification are presented in Table 5. Wild type E. coli colonies were tested in parallel as a negative control.

Adaptive Evolution:

The mutant strain was adapted though continuous passage in M9 minimal medium supplemented with 2 g/l D-glucose and trace elements as reported earlier (15, 17). To initiate evolutions, an ECOM3 mutant was plated on the solid M9 minimal media containing 2 g/l glucose, trace elements, EZ supplements and kanamycin antibiotic and incubated overnight at 37° C. A single colony was selected from the ECOM3 plate, re-suspended in 10 µl of sterile water and inoculated into three 500 ml Erlenmeyer flasks containing 250 ml of M9 minimal media supplemented with 20 ml of 5× Supplement EZ (Teknova). Flasks were incubated at 37° C. using a stir bar for mixing and aeration (~1000 rpm). Every day, optical density measurements (OD at 600 nm) were taken and cells were passed into a fresh medium. The volume of the inoculum for each passage was adjusted to account for changes in growth rate, and ensure that cultures would not enter the stationary phase before next passage. The amount of EZ supplements added to the media was reduced exponentially within the first two weeks of evolution. The evolutions were propagated under oxic condition for 60 days [~700 generations] until a stable growth rate was reached. Cultures were screened every other day for contamination using PCR. The evolutions were also supplemented with 50 µg/ml kanamycin once a week in order to prevent contamination. Each evolved cell population was sampled to investigate the effects of adaptive evolution on cellular metabolism at day 1, day 30 [~268 doublings], and day 60 [~700 doublings] Samples were also frozen on day 1 and every 2 days throughout the evolution.

Phenotype Assessment:

To measure growth rate and byproduct secretion, each population was grown in batch culture at 37° C. under oxic and anoxic conditions. Aerobic cultivation was conducted in 500 ml Erlenmeyer flasks containing 250 ml of M9 minimal media with trace elements and 2 g/l glucose as a sole carbon source. Temperature was controlled at 37° C. by a circulating water bath, mixing and aeration was controlled with a stir bar at ~1000 rpm. Anaerobic cultivation was conducted in 250 ml Erlenmeyer flasks with 200 ml of medium, sealed with rubber stoppers containing necessary inlet tubing. Anoxic conditions were achieved by continuous flashing of cultures with 95% $N_2$ 5% $CO_2$ gas mixture at flow rate of 1 ml/min. The temperature was controlled by using a circulating water bath; the mixing was controlled with a stir speed of ~200 rpm. Samples were taken from the batch cultures regularly (every 30 min), filtered through a 0.2 µm filter and stored at −20° C. for byproduct secretion analysis. Glucose concentration in the media was assessed using an enzymatic assay kit (R-Biopharm), while D-lactate secretion was measured using RI (refractive index) detection by HPLC (Waters, Milford, Mass.)

with a Bio-Rad Aminex HPX87-H ion exclusion column (injection volume, 50 µl) and 5 mM $H_2SO_4$ as the mobile phase (0.6 ml/min, 65° C.). The identities of metabolites and organic acids in the fermentation broth were further verified with enzymatic kits (R-Biopharm). The oxygen uptake rate of each aerobic culture was determined by measuring the rate of dissolved oxygen depletion in an enclosed respirometer chamber using a polarographic dissolved oxygen probe (Cole-Parmer Instruments, Vernon Hills, Ill.).

Quantitative PCR:

RNA samples were taken from exponentially growing cells and added to two volumes of RNA protect (Qiagen, Valencia, Calif.). Total RNA was isolated using an RNeasy mini kit (Qiagen, Valencia, Calif.). Reverse transcription was performed on 10 µg of total RNA. The reverse transcription mixture (60 µL) contained 10 µg total RNA, 75 µg random primers, 1× 1st Strand Buffer, 10 mM DTT, 0.5 mM dNTP's, 30 U of Superase, and 1500 U of Superscript II. The mixture was incubated in a thermocycler (Bio-Rad, Hercules, Calif.) at 25° C. for 10 min, 37° C. for 1 hr and then 42° C. for 1 hr. The reaction was followed by an incubating at 70° C. for 10 mM to inactivate the superscript. The RNA was then degraded by adding 20 µL of 1 N NaOH and incubating at 65° C. for 30 mM. After the incubation, 20 µL of 1 N HCl was added to neutralize the solution. QIAquick PCR Purification Kits were used to clean up the cDNA synthesis product. Following the purification, the cDNA was quantified and then directly used in qPCR reactions. The 50 ml of qPCR reaction contained 25 µl of SYBR Green Tag master mix (Qiagen), 0.2 µM forward primer, 0.2 µM reverse primer, and cDNA as a template. Each qPCR reaction was run in triplicates in the Bio-Rad thermocycler (Bio-Rad, Hercules, Calif.) with the following settings: 95° C. for 15 min, 94° C. for 15 s, 52° C. for 30 s, 72° C. for 30 s; the denaturation, annealing and extension steps were repeated for 40 cycles. Gene expression of evolved ECOM3 strains was analyzed under oxic and anoxic growth conditions and compared to the wild type strain under similar growth conditions. In order to determine the binding affinity of each primer set, a standard curve was calculated for each primer and reaction efficiency obtained from it. Using the standard curve, the relative cDNA quantity was obtained for each gene by normalizing it to the quantity of acpP (acyl carrier protein) cDNA in the same sample. acpP was chosen as the internal control gene since it is constitutively expressed in wild type and mutants under both aerobic and anaerobic conditions (7).

Clonal Analysis:

Evolved ECOM3 populations (day 60) were cultured overnight on solid M9 media with 2 g/l glucose and 50 µg/ml kanamycin. Ten random individual colonies were selected from each plate and grown overnight in M9 minimal media with 2 g/l glucose. Cells were harvested at 5000 rpm in the centrifuge (Thermo CR31), washed three times with M9 minimal media without carbon source and loaded on a Bioscreen C machine (Growth Curves USA). Cultures were inoculated into 300 µl wells containing M9 minimal media with 2 g/l glucose and trace elements, the initial OD of each well was kept bellow the 0.05. Cells were grown for 8 hours at 37° C. with continuous shaking to ensure good mixing and aeration and optical density (OD at 600 nm) measurements were taken every 15 min. Once the cells reached stationary phase, the assay was stopped and the final D-lactate concentration (g/l) was assessed by HPLC. Strains with the highest production yield were identified and subjected to aerobic batch cultivation. Strains were grown in 500 ml Erlenmeyer flasks with 250 ml of M9 minimal media for 8 hours at 37° C. with continuous agitation as described above. Samples were taken every 30 min, filtered and analyzed using the HPLC (Waters, Milford, Mass.). Growth rate (1/h), oxygen uptake rate (mmol/gDW/h), sugar uptake rate (mmol/gDW/h), and product secretion rates (mmol/gDW/h) were measured as described above.

Computational Analysis:

The computational analyses were done using the iAF1260 genome-scale metabolic model of E. coli K-12 MG1655 (13). The simulations were performed using either the Simpheny software platform (Genomatica, San Diego, Calif.) and the Matlab COBRA Toolbox (2) using established methods for gene deletion (11) and robustness analysis (12). The metabolic reconstruction has been examined with flux balance analysis (FBA). FBA provides a solution space that contains all of the possible steady-state flux distributions satisfying given constrains (10, 27). Phase plane analysis (4, 12) was used to calculate the range of characteristic phenotypes that a network can display as a function of variations in the activity of two reactions, such as LDH (lactate dehydrogenase) and the biomass function (growth) (see Supplementary materials). The model was constrained by experimental data by setting lower/upper bounds of uptake/secretion fluxes to the experimentally measured values. In order to allow for experimental uncertainty the bounds were set to within one experimental standard deviation of the experimentally measured mean value.

Example 3

Results of Examples 1 and 2

Strain Construction and Growth Adaptation

In an effort to develop an E. coli strain that would exhibit the similar phenotypic behavior under both oxic and anoxic culture conditions, we constructed a triple mutant of wild-type E. coli K-12 MG1655 strain (ECOM3 or E. coli Cytochrome Oxidase Mutant) that had the genes coding for the cytochrome oxidase bd (cydAB, b0733-b0734), cytochrome oxidase bo (cyoABCD, b0432-b0429) and putative cytochrome oxidase (cbdAB, b0979-b0978) completely removed from the genome. The cbd locus is annotated as a putative cytochrome oxidase and studies indicate that its gene products do not form a fully functional terminal oxidase (5, 29). Deletions of terminal cytochrome oxidases, encoded by the cydAB (cytochrome bd complex), cyoABCD (cytochrome bo complex), and cbdAB (also known as appBC) operons, have been previously reported in E. coli (8, 19, 24, 25, 29).

Initial Phenotypic Characterization and Adaptive Evolution

Figure 2:
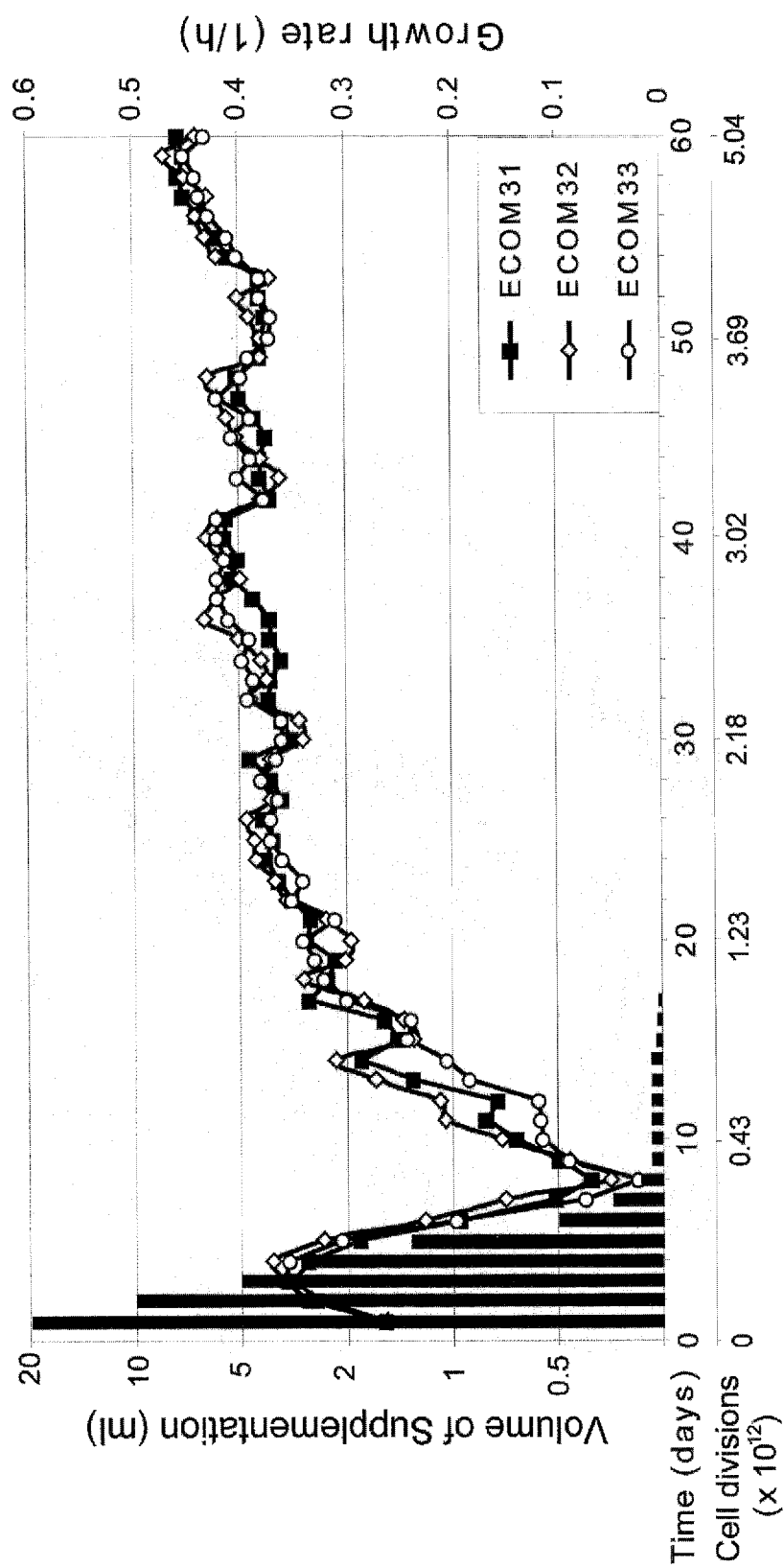
FIG. 2. Evolutionary trajectories of ECOM3 populations. Growth rate measurements for three evolved ECOM3 strains and cell divisions are shown as a function of time of evolution. Final average growth rate was 0.42+/−0.02 1/h. Anaerobic growth rate of wild-type *E. coli* is 0.45+/−0.02 1/h. The EZ amino acid supplement amount (in ml) is shown with black bars. The total number of cell divisions for the entire period of adaptation is presented on a secondary abscissa.
Figure 7:
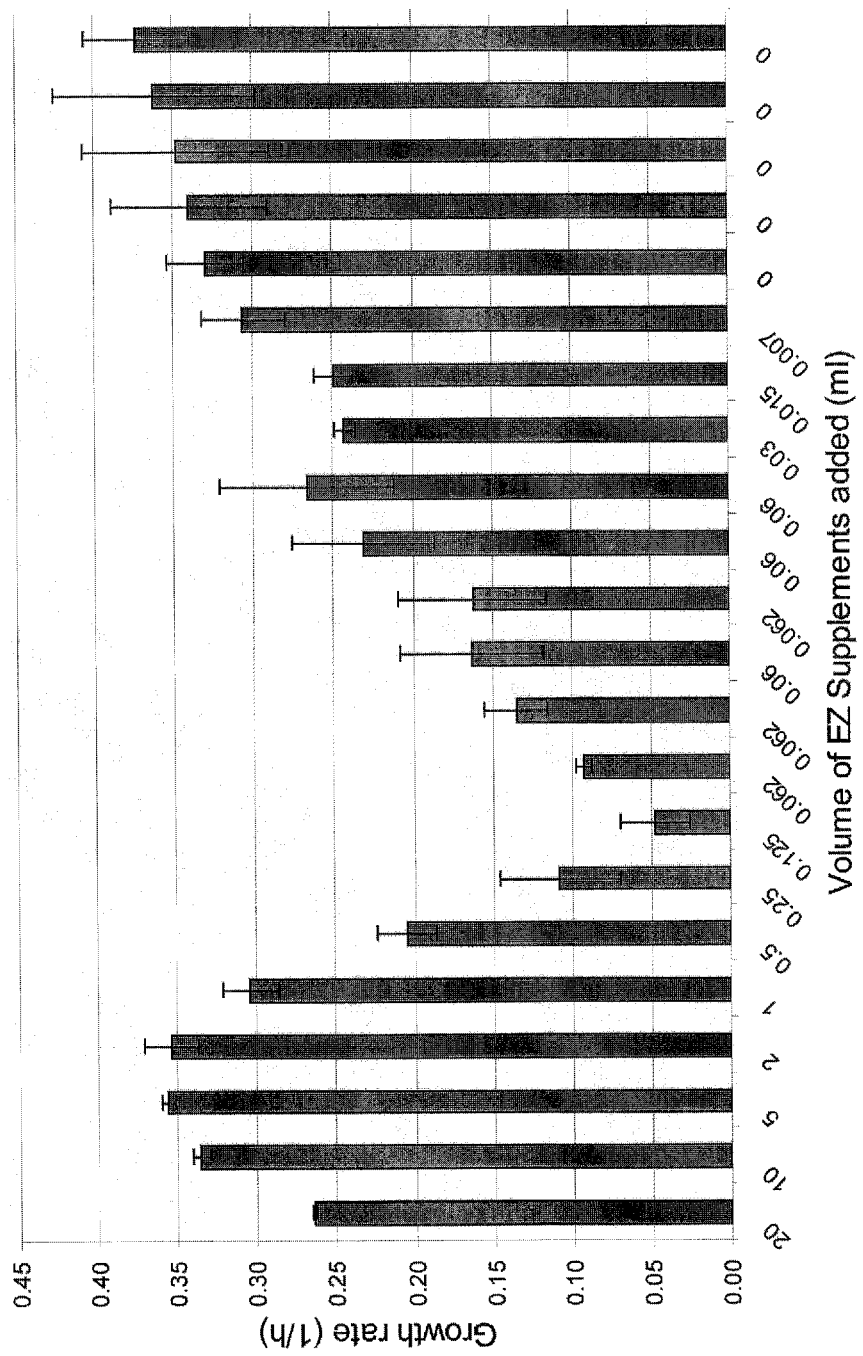
FIG. 7: Growth rate measurements for three evolved ECOM3 populations as a function of EZ Supplements addition (ml). Drop in growth rate was observed as supplementation was decreases during the first two weeks of evolution. No such response was observed after day 15 of evolution (EZ supplements amount is 30 μl).

The resulting ECOM3 strain was initially incapable of growing on M9 minimal medium supplemented with 2 g/l glucose and also demonstrated slow growth on LB media (0.034+/−0.002 1/h). Significant growth (0.25+/−0.02 1/h) was only observed on Rich Defined Media (Technova) and on M9 minimal media supplemented with a full mixture of amino acids (Supplement EZ, Technova). Three parallel adaptive evolutions (denoted by ECOM31, ECOM32, ECOM33) were conducted to adapt the initial ECOM3 strain to growth on M9 minimal media with glucose as the sole carbon source (FIG. 1). Initially, a rapid decrease in growth rate was observed upon reduction of the amino acid supplements (FIG. 2), but the growth rate increased once the supplement volume was reduced to 60 µl. The cells were then allowed to adapt to the new environment with the amount of supplement remaining unchanged for an additional six days. At day 14 of adaptive evolution, amino acid supplements were further reduced to 30 µl resulting in a significant change in growth rate. Further reduction in amino acid supplements had no effect on cell growth rate, and starting on day 17, amino acid supplements were no longer added to the media (FIG. 7). A rapid increase in growth rate followed complete removal of supplements and the growth rate reached a maximum of 0.44+/−0.01 l/h on day 56 of evolution. The evolutions were continued for an additional four days with no further observed growth rate increases (FIG. 2). Number of cell divisions that occurred during the term of evolution was estimated based on the amount of cells passed each day and the doubling time. The total number of cell divisions assuming a small death rate was $5.00 \times 10^{12}$ +/− $0.5 \times 10^{12}$ (average is reported) (FIG. 2).

The three independently evolved end-point populations (eECOM31, eECOM32, eECOM33) showed similar growth rate gains and acquired the ability to grow on glucose minimal medium without amino acid supplementation. Evolutions were stopped once the observed growth rates for the three end-point populations (0.42+/−0.02 l/h—average reported) became equivalent to the growth rate of wild type *E. coli* cultivated under anoxic conditions (0.45+/−0.02 l/h) indicating a similarity of the evolved ECOM3 populations to the anaerobic phenotype of the wild type strain. In order to further probe the metabolic phenotypes of the populations during and after evolutions, growth rates, oxygen uptake rates, sugar uptake rates, and product secretion rates were measured for each of the three on day 1, day 30, and day 60.

Phenotypic Characterization of the Evolved Populations

Phenotypic characterization of the evolved populations revealed that the three evolutionary endpoints had slightly different metabolic phenotypes (Table 3). As a common feature, a two-fold increase in substrate uptake rate was observed for all three populations from 9.98+/−2.0 mmol/gDW/h to 20.80+/−0.7 mmol/gDW/h on average within the first 30 days of evolution. Similarly, the D-lactate secretion rate increased more than two-fold by day 30 of adaptive evolution (from 17.00+/−2.9 mmol/gDW/h to 35.44+/−5.5 mmol/gDW/h on average), but the endpoint populations showed higher variance in lactate secretion than glucose uptake.

Acetate, one of the major fermentation products of wild type *E. coli*, was not a major growth byproduct of the ECOM3 parental strain prior to evolution. However, the three evolutionary endpoint populations had significantly different acetate secretion rates. Acetate secretion was strongly reduced in the eECOM31; while only a moderate reduction was seen in the eECOM32. In contrast, the acetate secretion rate of eECOM33 increased more than two-fold by day 60 (Table 3).

Figure 3:
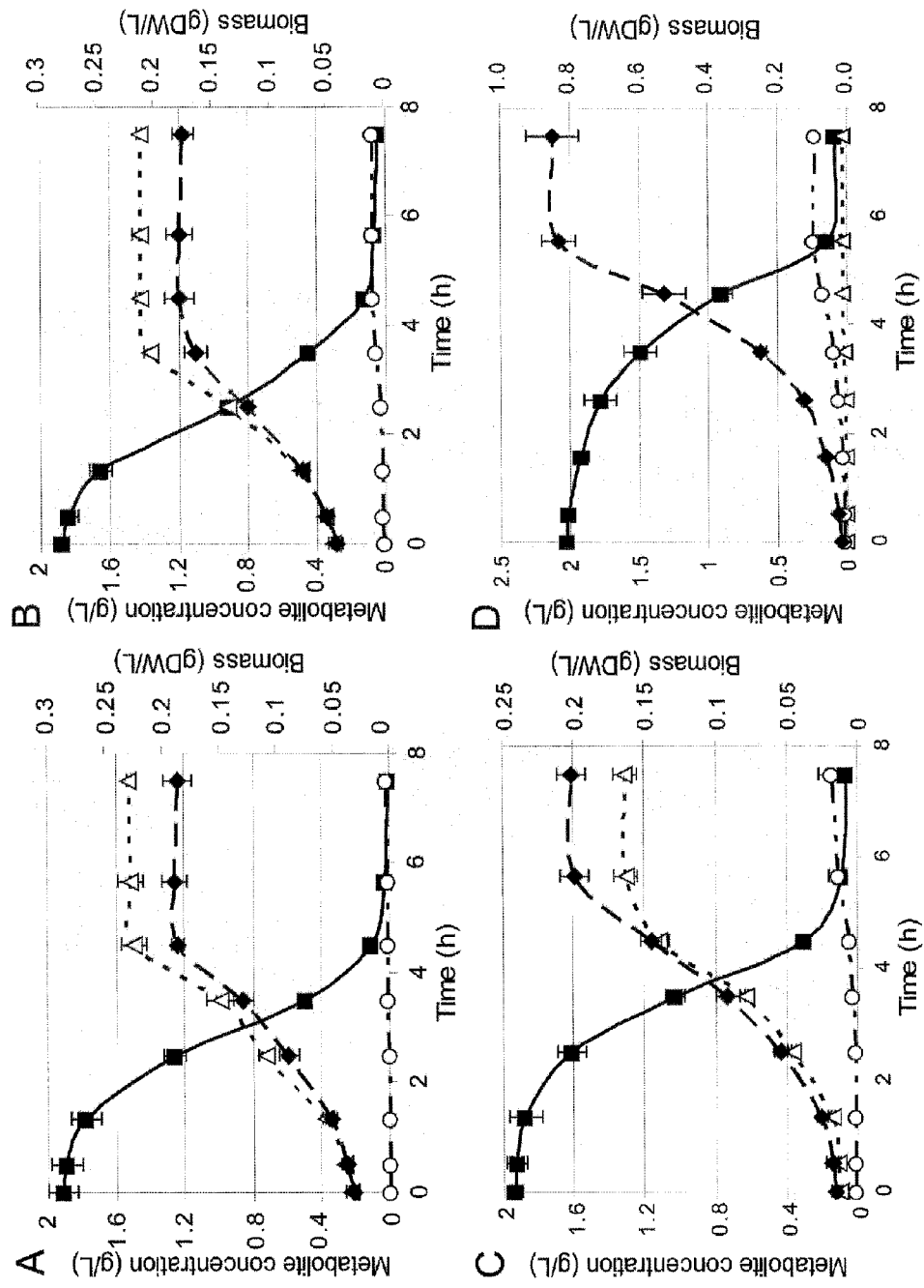
FIG. 3. Aerobic growth and secretion profiles of three end-point populations. A) eECOM31, B) eECOM32, C) eECOM33, and D) Wild Type strains. Data taken on day 60 of evolutions, all measurements were done in triplicate. Solid black line (■) indicates the concentration of glucose remaining in the culture; dashed black line (Δ) indicates the amount of D-lactate produced; dashed black line (O)—concentration of acetate; dashed black line (♦)—cell density (gDW/L).
Figure 4:
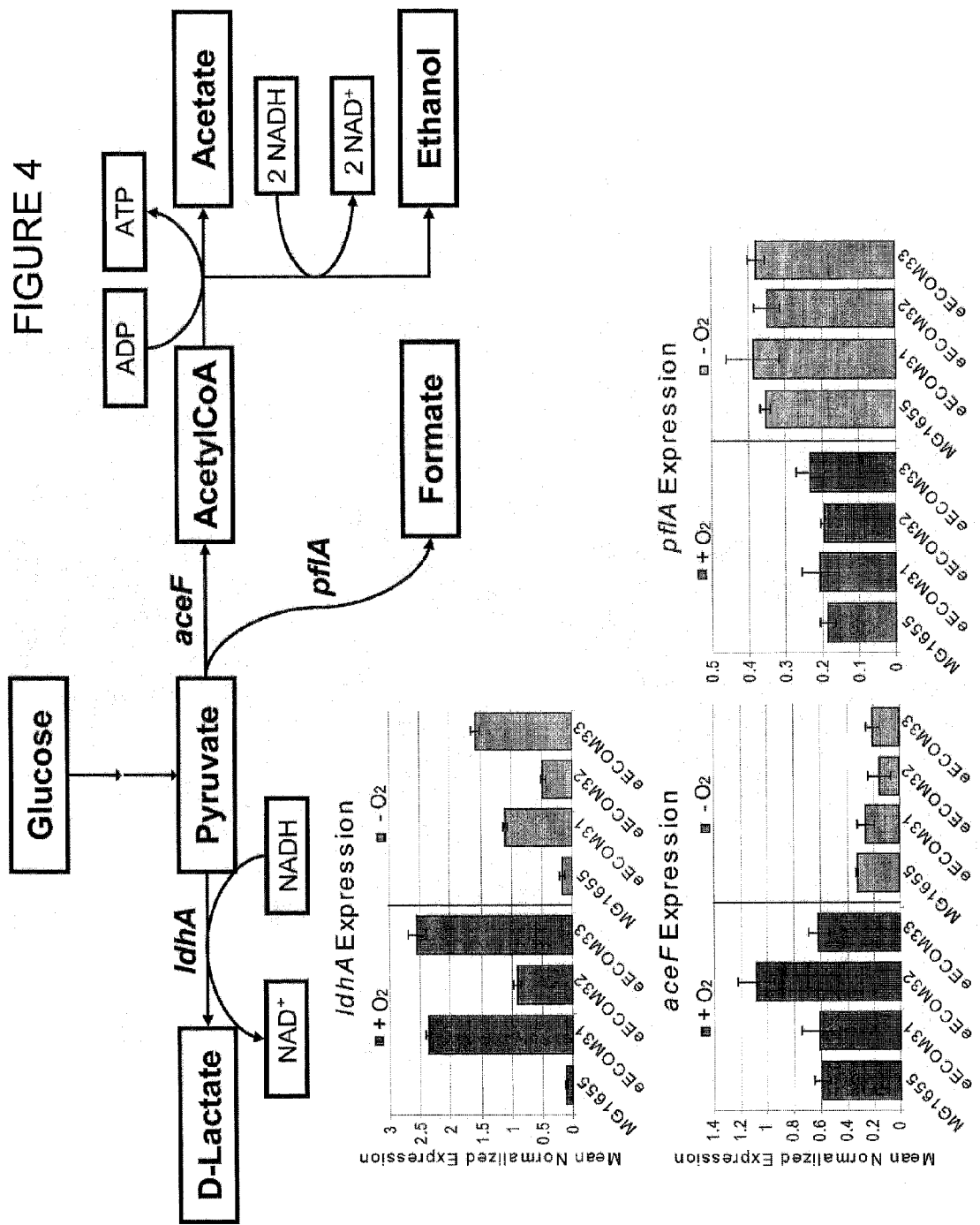
FIG. 4: Mechanism of D-lactate production and associated gene expression analysis. Pathways of conversion of pyruvate to common organic acids are presented with corresponding enzyme names. Gene expression of ldhA, aceF, and pflA genes was measured and presented by the bar diagrams. Gene expression was measured under oxic (dark grey bars) and anoxic (light grey bar) conditions. ldhA showed a significant upregulation while no upregulation was observed for aceF and pflA genes.
Figure 5:
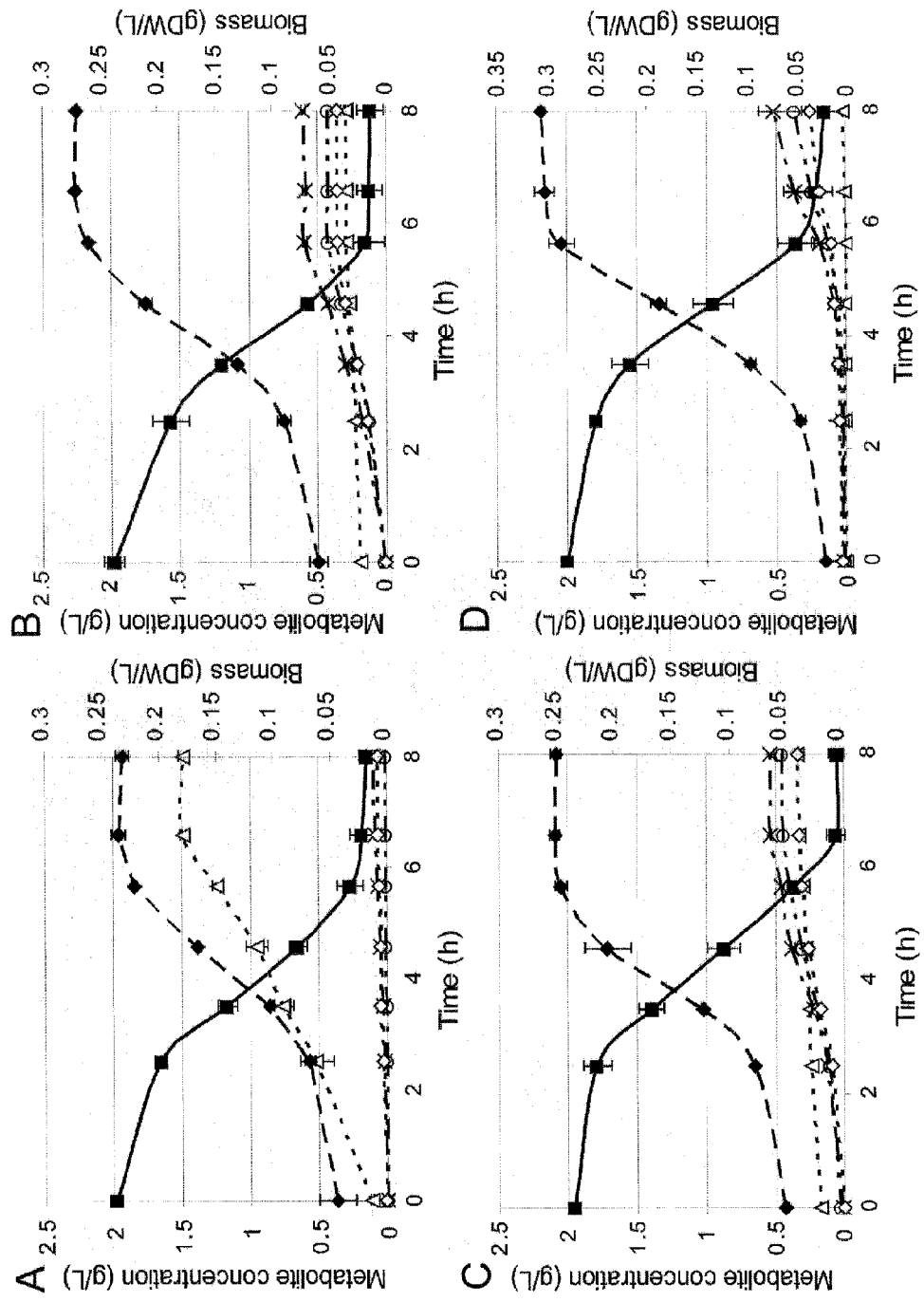
FIG. 5: Anaerobic growth and secretion profile of three endpoint populations. A—eECOM31, B—eECOM32, C—eECOM33, D—Wild Type strain. Solid black line (■) indicates the decrease in concentration of glucose remaining in the culture; dashed black line (Δ) indicates the amount of D-lactate produced; dashed black line (O)—acetate concentration; dashed black line (X)—formate concentration; dashed black line (O)—ethanol concentration and dashed black line (♦)—cell density (gDW/L).

Detailed secretion analysis of the ECOM3 end-point populations under oxic conditions (FIG. 3) indicated that the strains acquired the ability to secrete D-lactate as a dominant fermentation product at yields of 0.76, 0.73 and 0.65 g lactate/g glucose for eECOM31, eECOM32, and eECOM33, respectively. Compared to the wild type strain, the lactate secretion rates have increased by 94.5, 92.3 and 77.2 fold, while the substrate uptake rates have increased by 2.3, 2.2, and 2.3 fold, respectively, for the three evolved ECOM3 populations. These results are consistent with gene expression analysis using RT-PCR that showed that the ldhA gene, encoding the lactate dehydrogenase protein, was up-regulated by 21, 8, and 23 fold, respectively, in the three evolved strains compared with the wild type strain (FIG. 5). The increase in glucose uptake and lactate secretion, without the production of any other major fermentation products, results in a significantly elevated flux through the glycolytic pathway. Consistent with the physiological characteristics of the end point strains, we did not observe a significant increase in the expression of pyruvate dehydrogenase gene (aceF) or pyruvate foliate lyase (pflA) except in the case of the eECOM32 population (FIG. 4).

Clonal Analysis

Figure 8:
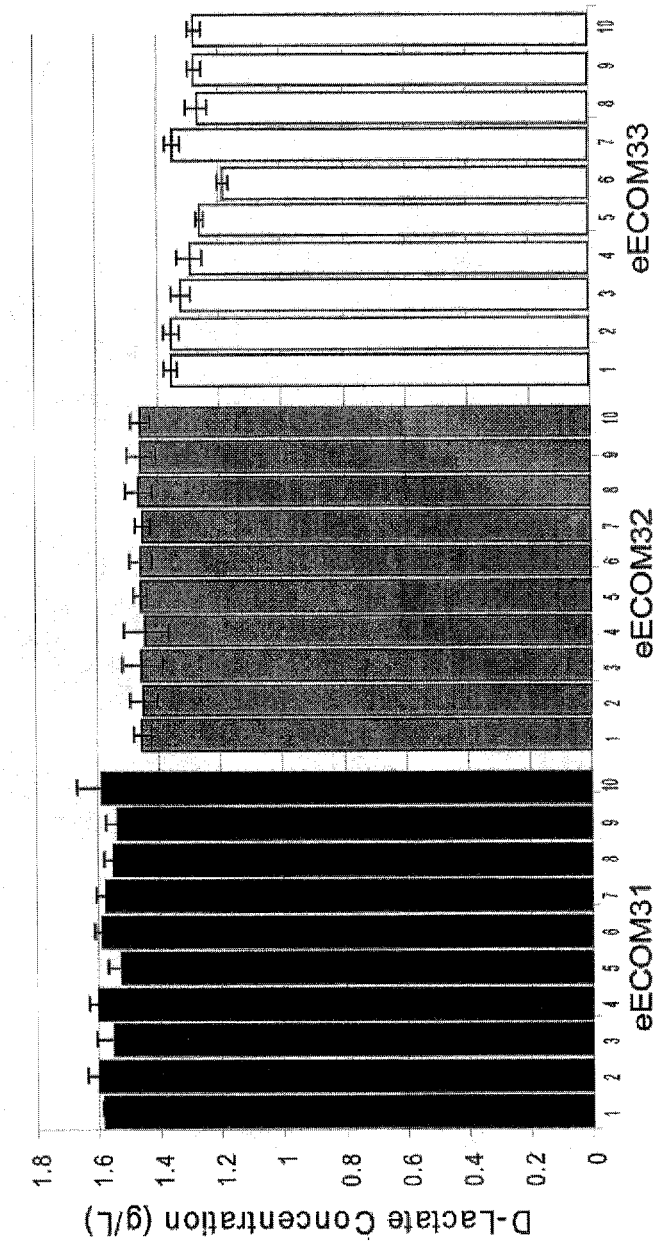
FIG. 8: D-lactate concentration from clonal analysis. Concentration of D-lactate produced by 30 clones isolated from three end point strains after 8 hours of growth. eECOM31—black bar; e ECOM32—grey bar, eECOM33—white bar.

In order to characterize and study heterogeneity in the evolved populations, we used clonal analysis. Evolved populations were plated on solid media at day 60 of evolution and ten random colonies from each population were selected for the analysis. We observed a higher level of heterogeneity within the eECOM33 population. The clone with the highest lactate yield (eECOM31LA) was identified within the eECOM31 population based on the highest final lactate concentration (FIG. 8). Phenotypic assessment of eECOM31LA showed compatible growth rates to eECOM31 population under oxic conditions, with slightly higher glucose uptake and lactate secretion rates (GUR: 21.61+/−0.16 mmol/gDW/h; LactSR: 42.32+/−2.52 mmol/gDW/h). The final lactate concentration for eECOM31LA strain was 1.58+/−0.1 g/l, which is equivalent to 80% conversion of glucose to lactate (0.8 g lactate/g glucose). The growth rate of the eECOM31LA (0.39+/−0.01 l/h) was slightly lower than that of the eECOM31 population. Moreover, we observed that eECOM31LA mutant had significantly lower oxygen uptake rate (2.44 mmol $O_2$/gDW/h) then eECOM31 population, demonstrating a wide range of oxygen requirements established during adaptive evolution.

Oxygen Dependency of ECOM Strains

In order to determine whether the presence or absence of oxygen affects the phenotype of ECOM3 strain we subjected three evolved populations to anaerobic growth on M9-glucose minimal media. We observed a slight decrease in growth rate, 12%, 5%, and 7% for three populations respectively as well as radically different secretion profiles compared to the aerobic phenotype (Table 4). Secretion analysis demonstrated that eECOM31 population preserved its aerobic phenotype and produced D-lactate as the sole byproduct at a concentration similar to the one observed under oxic growth conditions. In contrast, the eECOM32 and eECOM33 lost their ability to secrete D-lactate as a sole byproduct and presented with a phenotype similar to the wild-type *E. coli* under anoxic growth conditions with formate, acetate, and ethanol as byproducts (FIG. 5). Gene expression analysis of the ldhA, pflA, and aceF genes under anoxic growth conditions failed to reveal a clear mechanistic basis for the observed physiological differences between the three strains.

We originally hypothesized that deletion of cytochrome oxidases would completely eliminate oxygen consumption by the ECOM3 strain. However, while oxygen consumption was significantly reduced in the evolved strains, some residual oxygen uptake remained Prior to evolution (day 0), the oxygen uptake rate of the ECOM3 strain was 6.89+/−1.61 mmol $O_2$/gDW/h, which is almost three times lower than the oxygen uptake rate of the wild type strains. The oxygen consumption was further reduced to 3.84+/−1.7 mmol $O_2$/gDW/h (average reported for all evolved populations) by the end of the adaptive evolution (Table 3). Evolved populations showed significantly different oxygen uptake rates: 5.62+/−0.34, 3.69+/−0.66, and 2.21+/−0.38 mmol $O_2$/gDW/h for the eECOM31, eECOM32, and eECOM33, respectively. Gene expression analysis together with in silico phenotypic modeling (see Discussion) revealed that oxygen uptake levels were consistent with observed levels of expression of ygiN gene (annotated as quinol monooxygenase (1); however since the proposed biochemical reaction (1) does not involve incorporation of oxygen into an electron donor the term monooxygenase should not be used). The eECOM31 population showed the highest OUR consistent with the highest ygiN expression. In order to determine YgiN is involved into oxygen uptake we conducted an additional gene deletion and removed ygiN from the original unevolved ECOM3 strain. The removal of ygiN almost completely eliminated oxygen uptake (see Discussion).

Generation, Adaptation, and Phenotypic Characterization of the ECOM4 Strain.

Data herein shows that a respiratory deficient *E. coli* strain was generated to be used as a platform strain for metabolic and evolutionary engineering. The *E. coli* Cytochrome Oxydase Mutant (ECOM3) strain described before (Portnoy et al., *Appl. Environ. Microbiol.* 74, 7561-9, 2008) was further mutated by removal of the ygiN gene, followed by adaptation to glucose minimal medium, producing a strain (ECOM4) that utilized no oxygen even when grown in air. This strain grew similarly in oxic and anoxic conditions and exhibited almost-stoichiometric conversion of glucose into D-lactate.

To examine the metabolism of ECOM4 in more detail, this strain and its MG1655 wild-type parent were grown in minimal medium with [U-13C], [1-13C] or [6-13C] glucose. Cell pellets were digested in 6N hydrochloric acid and the 13C labeling of amino acids was determined by GC-MS. Labeling patterns were used to infer input of converging metabolic pathways to amino acids and related central metabolites. The complete tricarboxylic acid cycle did not operate in ECOM4. Oxaloacetate (aspartate) was derived wholly from anaplerotic conversion of phospho-enol pyruvate. Flux through the pentose phosphate pathway relative to glycolysis was much reduced in ECOM4, but relative inputs to the pentose phosphate pool from the oxidative or non-oxidative branches of the pentose phosphate pathway were similar to wild-type. Otherwise, the ECOM4 strain was metabolically similar to WT: there was still some reverse flux of aspartate/oxaloacetate back through the TCA cycle to symmetrical intermediates and there was no enhancement of the Entner-Doudoroff pathway or pyruvate-formate lyase activity. These results, based on analysis of local flux, were compared to a global constraint-based metabolic flux analysis. This procedure also indicated decreased TCA and pentose phosphate pathway flux and increased glycolytic activity in the ECOM4 cell line.

Figure 11:
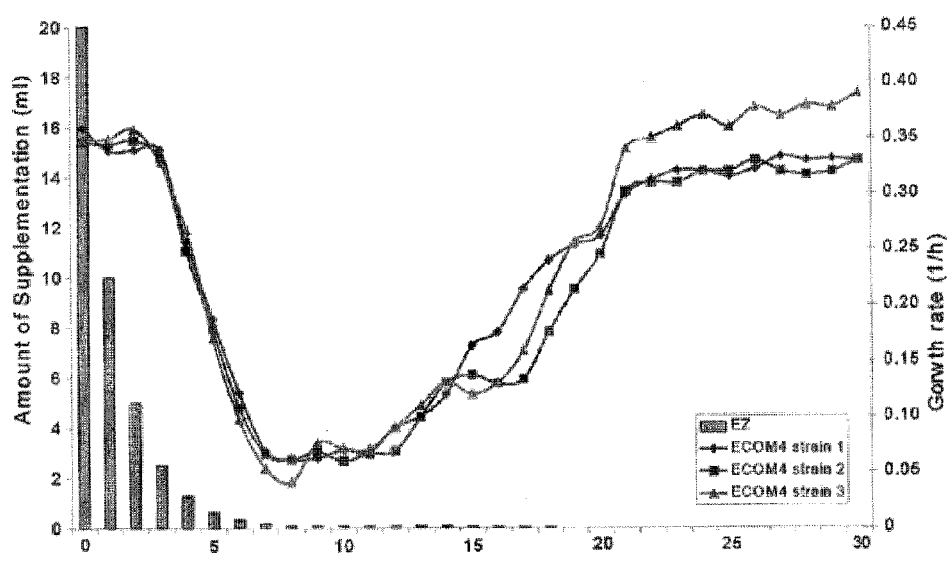
FIG. 11: Adaptive evolution of ECOM4 strain. Growth rate measurements for three evolved ECOM4 strains and cell divisions are shown as a function of time of evolution. The EZ amino acid supplement amount (in ml) is shown with green bars.

The ECOM4 strain (cydABcyoABCDcbdABygiN) was generated using the parental ECOM3 strain (cydABcyoAB-CDcbdAB) described here (1). In silico analysis of the remaining oxygen uptake in ECOM3 unexpectedly revealed that YgiN protein might be involved in oxidation of ubiquinol molecule to the ubiquinone form, through coupling of this oxidation reaction with reduction of the molecular oxygen. In order to test this prediction we deleted the ygiN from the ECOM3 background strain and observed nearly complete elimination of oxygen uptake. The resulted strain was characterized (Table 1 (column 1)) and adaptively evolved in the similar fashion as the ECOM3 strain (1), the growth rate trajectories are presented in FIG. 11. In short, a single colony was selected from the plate with ECOM4 culture, re-suspended in 10 μl of sterile water and inoculated into three 500 ml Erlenmeyer flasks containing 250 ml of M9 minimal media supplemented with 20 ml of 5× Supplement EZ (Teknova). Flasks were incubated at 37° C. using a stir bar for mixing and aeration (~1000 rpm). Every day, optical density measurements (OD at 600 nm) were taken and cells were passed into a fresh medium. The volume of the inoculum for each passage was adjusted to account for changes in growth rate, and ensure that cultures would not enter the stationary phase before next passage. The amount of EZ supplements added to the media was reduced exponentially within the first two weeks of evolution. The evolutions were propagated under oxic condition for 30 days [~350 generations] until a stable growth rate was reached. Strain was characterized during the evolution; data is presented in Table 1.

Upon completion of adaptation strains were characterized and one strain with the highest lactate secretion rate was selected (The rest of the data is for this strain only).

Oxic/Anoxic Growth of the ECOM4 Strain.

Figure 12:
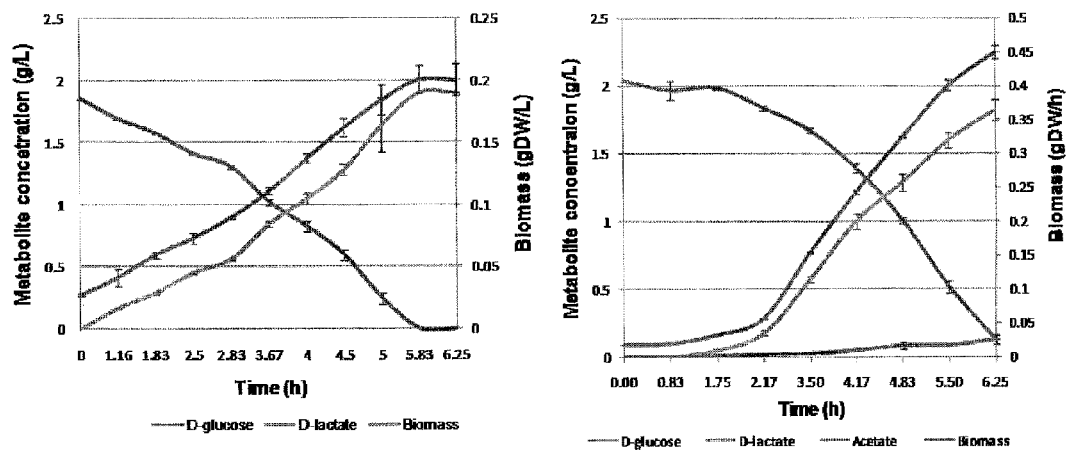
FIG. 12: Oxic and anoxic growth profiles of the ECOM4 strain. Left plot illustrates aerobic growth, with nearly all glucose being converted into lactate. Right plot illustrates anaerobic growth with slight presence of acetate as a byproduct.

The ECOM4 strain was subjected to oxic and anoxic growth. The growth profiles are very similar and presented in FIG. 12. A few slight differences to note between oxic and anoxic growth patterns for the ECOM4 strain: the growth rate is higher when cultured anaerobically, also cells tend to grow to a higher optical density anaerobically; lactate yield is nearly 98% aerobically, while a slight presence of acetate was noted during anoxic growth.

Lactate Yield Associated with the ECOM4 Strain.

As mentioned earlier the ECOM4 strain is bale to convert glucose to lactate with nearly 100% efficiency, when grown on rich media or minimal media supplemented with yeast extract. Similar lactate production potential was observed when the ECOM4 cell line was grown on LB media supplemented with 4 g/l glucose. At the end of adaptive evolution the lactate yield has dropped to 85% because, in order to sustain the cell growth more carbon is directed towards the biomass formation and less towards the lactate. When evolved ECOM4 cell line was grown on minimal media supplemented with 4 g/L glucose and yeast extract the lactate yield was above 95%.

TABLE 1

Phenotypic data resulted from characterization of ECOM4 strain during 30 day adaptive evolution.

| | day 0 | day 1 | day 10 | day 20 | day 30 |
|---|---|---|---|---|---|
| GR (1/h) | 0.38 +/− 0.02 | 0.36 +/− 0.01 | 0.06 +/− 0.01 | 0.25 +/− 0.03 | 0.33 +/− .03 |
| SUR (mmol/gDW/h) | 19.79 +/− 0.6 | 18.73 +/− 0.5 | 11.42 +/− 0.9 | 24.7 +/− 0.8 | 26.51 +/− 0.5 |
| LactSR (mmol/gDW/h) | 37.61 +/− 0.9 | 36.28 +/− 0.9 | 22.21 +/− 2.1 | 41.71 +/− 1.2 | 43.78 +/− 1.0 |
| Lact/Gluc (%) | 0.90 | 0.94 | 0.92 | 0.89 | 0.85 |
| AcSR (mmol/gDW/h) | 0.00 | 0.00 | 0.00 | 0.00 | 0.00 |
| OUR (mmol/gDW/h) | 0.31 +/− 0.15 | 0.27 +/− 0.1 | 0.15 +/− 0.02 | 0.24 +/− 0.1 | 0.25 +/− 0.12 |
| EZ supplements (ml) | + | + | +/− | − | − |

SUR: substrate uptake rate;
LactSR: lactate secretion rate;
AcSR: acetate secretion rate;
OUR: oxygen uptake rate.

Example 4

Discussion of Results of Example 3

To our knowledge, we describe here the first *E. coli* strain that is able to homoferment glucose to lactic acid under aerobic growth conditions. This strain (ECOM3) was engineered by removing all active cytochrome oxidases. Genes were removed using homologous recombination techniques and the resulted strain was evolved to achieve growth on M9 minimal media with trace elements and 2 g/l glucose. The observed growth rate after 60 days of evolution was equivalent to the growth rate of wild type *E. coli* under anoxic conditions. Adaptive evolution produced three end-point populations that exhibited similar behavior aerobically and had radically different phenotypic characteristics anaerobically. Lactic acid was identified as a major product of aerobic fermentation for all there end-point populations. The best representative of eECOM31 population exhibited the highest lactate secretion and glucose uptake rate. The yield of lactate from glucose was close to 80%. We used gene expression analysis to investigate genetic perturbations that underlined secretion of lactic acid, and remaining oxygen uptake rate. We also utilized a genome-scale metabolic model of *E. coli* (iAF1260) to understand the mechanism of oxygen utilization in the ECOM3 phenotype.

In Silico Analysis Using a Genome-Scale Model

Figure 6:
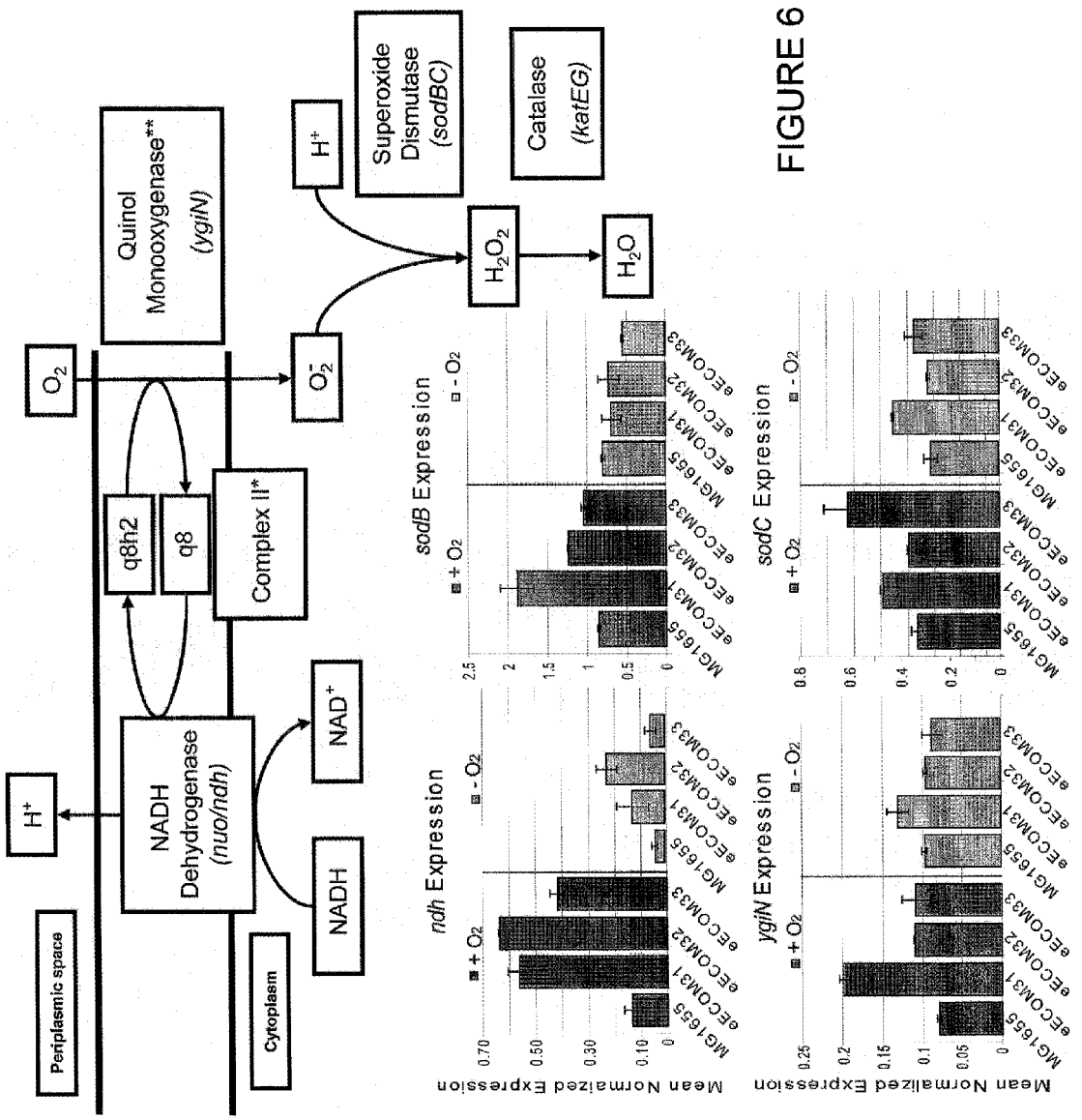
FIG. 6: Proposed mechanism of oxygen utilization by ECOM3 strains and corresponding gene expression. Possible mechanism of oxygen utilization by ECOM3 strains is presented. This mechanism was elucidated based on gene expression analysis (bar diagrams) and scientific evidence (1, 3, 18). Gene expression was measured under oxic (dark grey bars) and anoxic (light grey bar) conditions. Expression for the catalase is not shown. *Complex II was not included in this figure due to lack of evidence of its involvement.

In order to identify potential metabolic fates of oxygen in ECOM3 strain, we employed a genome-scale metabolic model of *E. coli* (iAF1260) (13). The in vivo genotype of the ECOM3 strain was implemented computationally though the removal of reactions catalyzed by the deleted genes. The in silico model was further constrained using experimental data to set the glucose and oxygen uptake rates and acetate secretion rates (with experimental error accounted for by allowing a range of uptake/secretion rates). Analysis of the computationally predicted flux distributions utilizing these constraints provided insights into the observed residual oxygen utilization. The model predicted that the mechanism that could account for residual oxygen uptake at the observed level would be through the activity of the ygiN. The simulation of the ECOM3 phenotype with computational model and scientific evidence showed flux coupling between the NADH dehydrogenase (nuo/ndh operons) and the reaction catalyzed by the ygiN gene forming a ubiquinone cycle. It has been shown that ubiquinone is the electron acceptor for the NADH dehydrogenase (ndh/nuo) (18) and a preferred electron carrier for *E. coli* during aerobic growth (3). Furthermore, Adams and Jia (1) indicate that ygiN can potentially react with ubiquinol molecule and oxidize it to the ubiquinone form, through coupling of this oxidation reaction with reduction of the molecular oxygen. Based on these findings we proposed the mechanism for oxygen utilization (FIG. 6).

The removal of the ygiN gene in silico, predicted elimination of the oxygen uptake. In order to determine if ygiN accounts for the oxygen uptake we removed it from the parental ECOM3 strain and observed nearly complete elimination of oxygen uptake: 0.03+/−0.04 mmol $O_2$/gDW/h. This experimental evidence demonstrates that observed oxygen uptake can be attributed to the activity of YgiN. Consistent with the role of this pathway in residual oxygen utilization, we found that levels of aerobic expression of all the genes in this pathway were increased in the ECOM3 populations compared to the wild type strain (FIG. 6). In particular, the expression of ygiN gene was increased nearly three times in the eECOM31. Additional computational analysis of the observed phenotype is presented in supplementary materials.

In summary, we have engineered an *E. coli* strain (ECOM3) capable of homofermenting glucose to lactate in both aerobic and anaerobic conditions by deleting all cytochrome oxidase genes and adapting the strain to grow on minimal media without amino acid supplementation. Clonal analysis allowed identifying the best lactic acid producer from the eECOM31 population with lactate yields close to 80% from glucose. Interestingly, cell populations derived from the adaptive evolution showed significant residual oxygen uptake. We identified the mechanisms accounting for and the observed residual oxygen uptake using a combination of genome-scale metabolic model of *Escherichia coli* and gene expression analysis of specific pathways. The resulting ECOM3 populations have been shown to be amenable to genetic manipulation (results not shown) and thus can be used as a platform strain for further metabolic engineering that redirect lactate flux into other desirable byproducts.

TABLE 2

Strains and plasmids used.

| Strains and Plasmids: | Relevant Characteristics | Source or Reference |
|---|---|---|
| Strains | | |
| MG1655 | *Escherichia coli* (Wild Type) | ATCC (Cat: 47076) |
| ECOM3 | MG1655, Δ(cydAB-appBC-cyoABCD)::FRT-kan-FRT | This study |
| ECOM3ygiN | MG1655, Δ(cydAB-appBC-cyoABCD-ygiN)::FRT-kan-FRT | This study |
| eECOM31 | evolved ECOM3 strain 1 (60 days) | This study |
| eECOM32 | evolved ECOM3 strain 2 (60 days) | This study |
| eECOM33 | evolved ECOM3 strain 3 (60 days) | This study |
| eECOM31LA | Best Lactate producer isolated from eECOM31 culture | This study |
| Plasmids | | |
| pKD46 | bla γβ exo (Red recombinase), temp. conditional pSC101 operon | 9 |
| pKD13 | Template plasmid with FRT-kan-FRT (kanamycin cassett) | 9 |
| pCP20 | FLP+, λ cI857+, λ pr RepTS, ApR, CmR | 6 |

TABLE 3

Phenotypic characteristics of ECOM3 populations during adaptive evolution.

| | MG1655 | ECOM3 | ECOM31 day 1 | ECOM31 day 30 | ECOM31 day 60 | ECOM32 day 1 |
|---|---|---|---|---|---|---|
| SUR mmol/gDWh | 9.02 +/− 0.23 | 11.88 +/− 2.01 | 7.67 +/− 0.60 | 20.88 +/− 0.89 | 19.89 +/− 0.94 | 11.07 +/− 0.78 |
| OUR mmol/gDWh | 14.92 +/− 0.21 | 6.9 +/− 1.52 | 7.90 +/− 1.00 | 3.81 +/− 0.45 | 5.61 +/− 0.30 | 7.75 +/− 0.42 |

TABLE 3-continued

Phenotypic characteristics of ECOM3 populations during adaptive evolution.

| | | | | | | |
|---|---|---|---|---|---|---|
| LactSR mmol/gDWh | 0.40 +/- 0.01 | 17.60 +/- 0.65 | 16.63 +/- 0.70 | 35.09 +/- 0.36 | 36.36 +/- 0.25 | 15.94 +/- 0.98 |
| AcSR mmol/gDWh | 3.4 +/- 0.02 | 3.84 +/- 0.45 | 3.75 +/- 0.49 | 0.33 +/- 0.05 | 0.50 +/- 0.02 | 4.32 +/- 0.58 |

| | ECOM32 | | ECOM33 | | |
|---|---|---|---|---|---|
| | day 30 | day 60 | day 1 | day 30 | day 60 |
| SUR mmol/gDWh | 20.53 +/- 1.01 | 21.15 +/- 1.50 | 11.23 +/- 1.20 | 16.90 +/- 2.16 | 21.28 +/- 0.97 |
| OUR mmol/gDWh | 5.26 +/- 0.24 | 3.69 +/- 0.60 | 5.04 +/- 0.50 | 4.29 +/- 0.21 | 2.22 +/- 0.38 |
| LactSR mmol/gDWh | 35.15 +/- 2.64 | 35.63 +/- 1.56 | 17.24 +/- 0.98 | 25.84 +/- 2.19 | 29.98 +/- 2.81 |
| AcSR mmol/gDWh | 2.73 +/- 0.47 | 2.31 +/- 0.31 | 3.43 +/- 0.68 | 3.48 +/- 0.22 | 8.17 +/- 0.91 |

TABLE 4

Phenotypic comparison of ECOM3 populations between the oxic and anoxic growth environment.

| Strain | Aerobic GR (1/h) | Anaerobic GR (1/h) | Aerobic Lactate Titer (g/L) | Anaerobic Lactate Titer (g/L) |
|---|---|---|---|---|
| Unevolved wild-type | 0.71 +/- 0.01 | 0.45 +/- 0.02 | 0 | 0.04 +/- 0.01 |
| eECOM31 | 0.42 +/- 0.01 | 0.37 +/- 0.01 | 1.51 +/- 0.01 | 1.47 +/- 0.01 |
| eECOM32 | 0.40 +/- 0.02 | 0.38 +/- 0.02 | 1.45 +/- 0.04 | 0.29 +/- 0.02 |
| eECOM33 | 0.44 +/- 0.02 | 0.42 +/- 0.01 | 1.30 +/- 0.06 | 0.31 +/- 0.03 |

Supplementary Materials to Examples 1-4 Discussed Above

Phase Plane and Gene Deletion Analysis Using Metabolic Model.

When the experimentally derived uptake/secretion rate constraints were imposed on the model, it predicted no lactate fermentation when a particular flux distribution was determined by maximizing biomass production using flux balance analysis (FBA, FIG. 9A). We used the model and experimental data obtained for ECOM3 strains to map the observed phenotypes to the predicted space of allowed lactate secretion rates as a function of growth rate (FIG. 9B). Phenotypes of the three end point strains lie close to the corner point of this space (growth rate 0.42 l/h; average lactate production 33.9 mmol/gDW/h) that correspond to trade-off between growth and lactate production. The inability of biomass maximization to predict observed phenotypes was interesting as in previous studies metabolic phenotypes of evolved strains could be accurately predicted using FBA (2, 3). We assumed that the reason for the inability of FBA to correctly predict the lactate secretion phenotype was that there are additional constraints or metabolic bottlenecks that limit the ability of the evolved ECOM3 strains to grow optimally (FIG. 9B).

Figure 9:
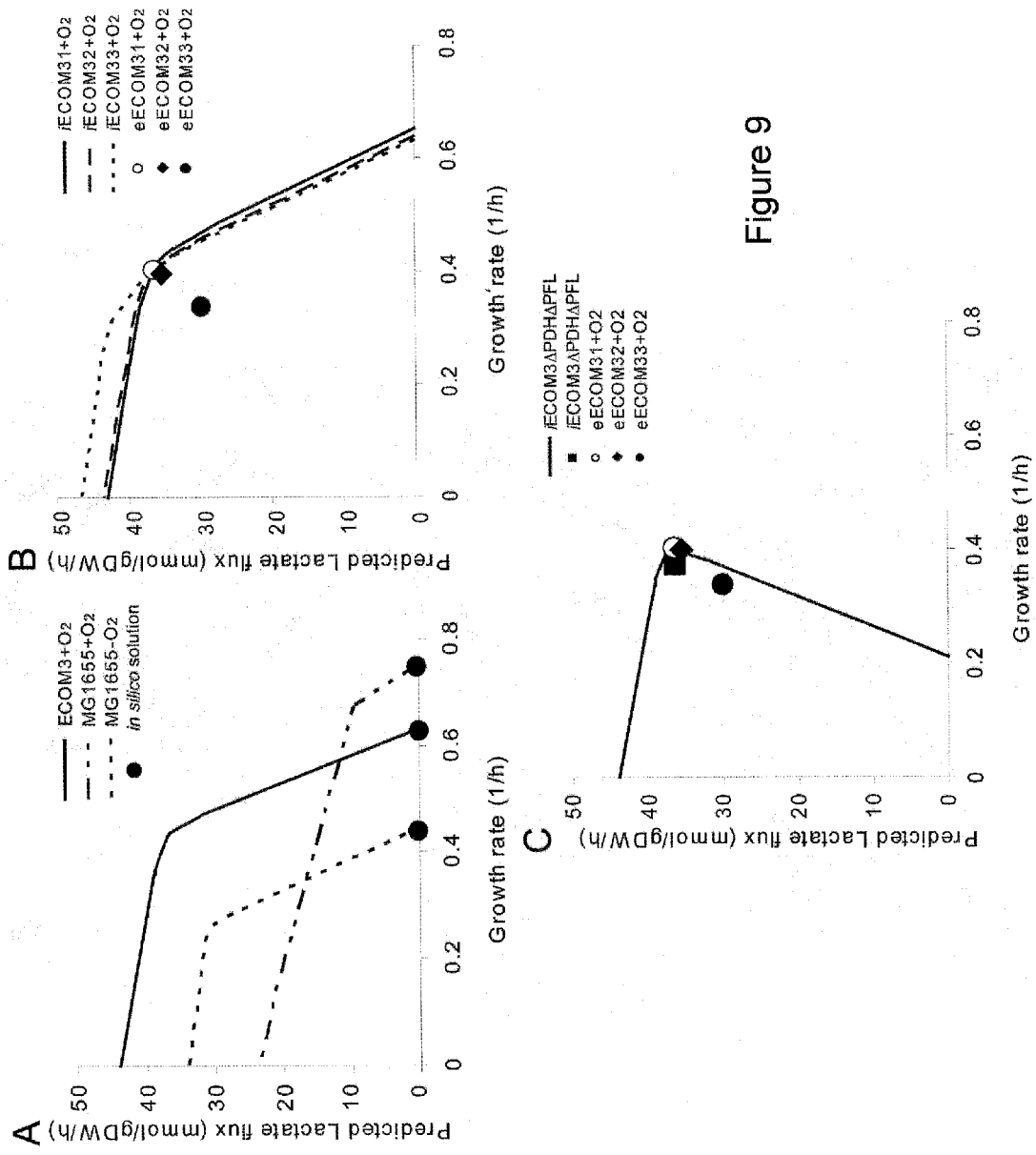
FIG. 9: Comparison of experimental and computationally predicted growth rates and lactate secretion rates for the evolved ECOM3 populations. A. Two-dimensional computational solution envelopes (lines) containing all possible flux distributions for the given constrains and computationally predicted flux values (circles) are shown for aerobic and anaerobic wild type (iMG1655) strain and for aerobic iECOM3 (using average values for the three evolved strains as constraints). The model predicts that the experimental flux values need to reside inside the solution envelope and that the optimal flux value to maximize biomass formation would reside at the maximum allowed growth rate point of the flux space (circles). B. Computational solution envelopes (lines) are shown for each of three end-point populations (solid line—ECOM31, dashed line—ECOM32, dotted line—ECOM33) using experimental data as constrains. eECOM31 (○), eECOM32 (♦), eECOM33 (●) solutions are based on experimental results and are lying within the solution envelope; C. The modified solution envelope after the removal of PHD (pyruvate dehydrogenase) and PFL (pyruvate formate lyase) reactions is shown (line). The optimal computational solution (iECOM3ΔPDHΔPFL) as well as experimental data points (eECOM31, eECOM32, and eECOM33) are shown. Note: 'i'—indicates an in silico solution.
Figure 10:
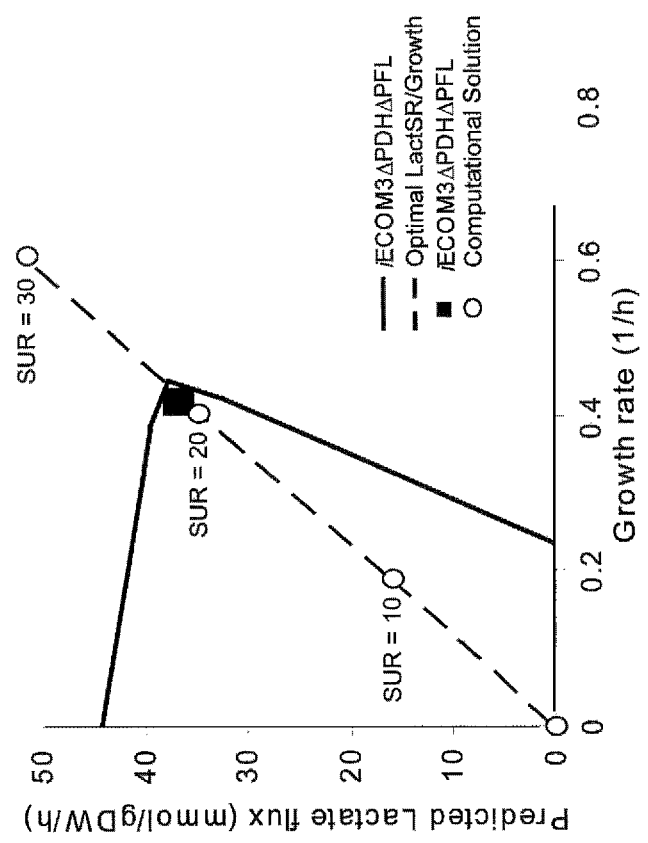
FIG. 10: Correlations between predicted lactate flux and growth rate with respect to different substrate uptake rates (SUR) are presented. With variable SUR the model predict different lactate/growth ratio but values are located on the same line as the original prediction.

In order to identify candidate bottleneck reactions, we used the computational model to determine what additional gene deletions could explain observed secretion of lactate as an optimal phenotype. By systematically enumerating all single and double reaction deletions of central metabolic and amino acid biosynthetic reactions in the iAF1260 model, we identified a number of double reaction deletions in the acetate and ethanol secretion pathways that predicted phenotypes (i.e. growth and lactate secretion) that were almost identical to the observed ECOM3 phenotype (FIG. 9C and Table 6). For instance, the removal of the pyruvate dehydrogenase (PDH) and pyruvate formate lyase (PFL) reactions from the model resulted in a predicted flux solution space where lactate secretion is coupled to biomass formation (growth). This prediction was generated by constraining the oxygen uptake and glucose uptake rate to the experimentally measured values (with experimental error included as lower/upper bounds). Predicted value for the lactate secretion at maximum growth rate matched the experimental measurements closely (FIG. 9C). In order to check that this prediction was not a result of the applied constrains we varied the value of glucose uptake within the range of 10-30 mmol/gDW/h, and obtained similar values for lactate secretion to growth ratio (FIG. 10).

Experimentally, we observed a significant increase in expression of ldhA gene but no downregulation of the pflA and aceF genes (corresponding to the PFL and PDH reactions) compared to the wild type strain. It is known that pyruvate formate lyase is inactivated aerobically by post-transcriptional mechanisms (1, 4, 5) and thus the PFL reaction is inactive in ECOM3 strain. Since the glycolytic flux in the ECOM3 strains was significantly increased, the lack of upregulation of aceF gene and inactivation PFL would effectively result in decreased flux through PDH and PFL reactions relative to the glycolytic flux. This in turn would result in a bottleneck effect in the acetate and ethanol secretion pathway, thus forcing secretion of lactate in accordance with the model predictions.

TABLE 5

Sequences of the primers used for gene deletion of cydAB; cyoABCD, and cbdAB operons as well as sequences of primers used to confirm the deletions.

| Deletion Primers | Forward Primer (5'-->3') | Reverse Primer (5'-->3') |
|---|---|---|
| cydAB | TGTGCCACTGACGCTCGGTATGGCGTTCCT GCTGGCCATTATGGAAACGGTCTACGTCCT GTGTAGGCTGGAGCTGCTTC | TACAGAGAGTGGGTGTTACGTTCAATATCT TCTTTGGTGATACGACCGAACATTTTCCAG ATTCCGGGGATCCGTCGACC |
| cyoABCD | ATGAGACTCAGGAAATACAATAAAAGTTT GGGATGGTTGTCATTATTTGCAGGCACTGT AGTGTAGGCTGGAGCTGCTTC | TTAGTGCATCATCATGTTGTAGTTGAGGTT CCACATAATCCAGATGGAGCCTACAACCAG ATTCCGGGGATCCGTCGACC |
| cbdAB | ATGTGGGATGTCATTGATTTATCGCGCTGG CAGTTTGCTCTGACCGCGCTGTATCACTTT GTGTAGGCTGGAGCTGCTTC | TTAGTACAACTCGTTTTCGTTACGGCGGAG AGITTCTGTTGTCATGCGCCCCCACATTTT ATTCCGGGGATCCGTCGACC |
| Confirmation primers | Forward Primer (5'-->3') | Reverse Primer (5'-->3') |
| cydAB | AAAGAATTAAGGTCAACCG | CGCCCGCAGGGGGCGCTTGTCCATT |
| cyoABCD | ATAACGCCCTTTTGCAACAG | GTTAAACACACAACCCGACGCCACA |
| cbdAB | GCTTAGCGAGGTATGTCAGT | TGTCAGATATGAAAAGCGGAAACAT |

TABLE 6

List of the double reaction deletions of central metabolism in the iAF1260 that produce optimal phenotypes similar to the ECOM3.

| Strain | Reactions Abreviation* | Reaction Name | Min D-lactate production (mmol/gDW/h) | Max D-lactate production (mmol/gDW/h) | Max growth rate (l/h) |
|---|---|---|---|---|---|
| WT | ALCD2x FHL | Alcohol dehydrogenase/Formate-hydrogen lyase | 10.33 | 10.33 | 0.22 |
| | ACALD PFL | Acetaldehyde dehydrogenase/Pyruvate formate lyase | 13.22 | 13.22 | 0.20 |
| | ALCD2x PFL | Alcohol dehydrogenase/Pyruvate formate lyase | 13.22 | 13.22 | 0.20 |
| | PHD PFL | Pyruvate dehydrogenase/Pyruvate formate lyase | 13.88 | 13.88 | 0.18 |
| iECOM31 | ALCD2x FHL | Alcohol dehydrogenase/Formate-hydrogen lyase | 29.28 | 29.28 | 0.39 |
| | ACALD PFL | Acetaldehyde dehydrogenase/Pyruvate formate lyase | 32.64 | 32.64 | 0.38 |
| | ALCD2x PHL | Alcohol dehydrogenase/Pyruvate formate lyase | 32.64 | 32.64 | 0.38 |
| | PHD PFL | Pyruvate dehydrogenase/Pyruvate formate lyase | 33.98 | 33.98 | 0.35 |
| iECOM32 | ALCD2x FHL | Alcohol dehydrogenase/Formate-hydrogen lyase | 31.39 | 31.39 | 0.43 |
| | ACALD PFL | Acetaldehyde dehydrogenase/Pyruvate formate lyase | 34.82 | 34.82 | 0.41 |
| | ALCD2x PHL | Alcohol dehydrogenase/Pyruvate formate lyase | 34.82 | 34.82 | 0.41 |
| | PHD PFL | Pyruvate dehydrogenase/Pyruvate formate lyase | 36.15 | 36.15 | 0.38 |
| iECOM33 | ALCD2x FHL | Alcohol dehydrogenase/Formate-hydrogen lyase | 32.19 | 32.19 | 0.43 |
| | ACALD PFL | Acetaldehyde dehydrogenase/Pyruvate formate lyase | 35.63 | 35.63 | 0.42 |
| | ALCD2x PHL | Alcohol dehydrogenase/Pyruvate formate lyase | 35.63 | 35.63 | 0.42 |
| | PHD PFL | Pyruvate dehydrogenase/Pyruvate formate lyase | 36.96 | 36.96 | 0.39 |

Minimal and Maximum D-lactate secretion flux (mmol/gDW/h) and Maximum growth rate (l/h) are shown for WT (wild type) and ECOM3 strains.
Experimentally measured fluxes were used as constrains for the model.
*Reaction Abbreviations are taken from the *E. coli* computational model iAF1260.

Example 5

Description of Preferred Embodiments

The constitutive activation of the anoxic redox control transcriptional regulator (ArcA) in *Escherichia coli* during aerobic growth, with the consequent production of a strain that exhibits anaerobic physiology even in the presence of air is reported in this work. Removal of three terminal cytochrome oxidases (ΔcydAB, ΔcyoABCD, ΔcbdAB) and quinol monooxygenase (ΔygiN) from the *E. coli* K12 MG1655 genome resulted in the activation of ArcA aerobically. These mutations, which are contemplated in certain preferred embodiments, resulted in reduction of oxygen uptake rate by nearly 98% and production of D-lactate as a sole by-product under oxic and anoxic conditions. The knock-out strain exhibited nearly identical physiological behavior under both conditions, suggesting that the mutations resulted in significant metabolic and regulatory perturbations. In order to fully understand the physiology of this mutant and to identify underlying metabolic and regulatory reasons that prevent transition from aerobic to anaerobic phenotype we utilized whole-genome transcriptome analysis, $^{13}$C tracing experiments and physiological characterization. Our analysis showed that the deletions resulted in the activation of anaerobic respiration under oxic conditions and a consequential shift in the content of the quinone pool from the ubiquinones to menaquinones. Increase in menaquinone concentration resulted in activation of ArcA. The activation of ArcB/ArcA regulatory system led to a major shift in the metabolic flux distribution through the central metabolism of the mutant strain. Flux analysis indicated: the mutant strain had undetectable fluxes around the TCA cycle, and elevated flux through the glycolysis and anaplerotic input to oxaloacetate. Flux and transcriptomics data were highly correlated and showed similar patterns.

Example 6

Introduction

*Escherichia coli* has been studied extensively with respect to its physiology, genetics, and metabolism. One of the unique features of its metabolism is the ability to support robust growth under both oxic and anoxic conditions (32). During aerobic growth, when oxygen is used as a terminal electron acceptor, *E. coli* divides rapidly and produces carbon dioxide and acetate as major growth by-products (32) representing an efficient form of energy metabolism. In the absence of oxygen, *E. coli* and other microorganisms rely on anaerobic respiration and fermentation in order to oxidize substrates, recycle electron carriers, and generate energy (32). This metabolic versatility of *E. coli* allows it to survive and thrive over a wide range of conditions.

Since the ability to produce a number of reduced by-products such as organic acids and ethanol is of importance in the field of metabolic engineering, the majority of the metabolic engineering designs rely on anaerobic conditions (14, 27, 28). It has also been shown that *E. coli* strains developed for overproduction of commodity chemicals can be further improved using adaptive evolution strategies (14). Adaptive evolution is often performed through a series of dilutions allowing cells to remain within the exponential phase; the environmental condition is hereby kept similar from passage to passage as environmental perturbations might result in an incorrect evolutionary trajectory (14). Implementation of adaptive evolution for strains requiring strict anoxic growth conditions is a challenging task; therefore the development of a platform strain that would be insensitive to oxygen and would exhibit similar physiological behavior under oxic and anoxic conditions would be beneficial and would significantly simplify the process of adaptation of anaerobic strain designs.

It has been shown before that the simultaneous deletion of three terminal cytochrome oxidases (cydAB, cyoABCD and cbdAB) and quinol monooxygenase (ygiN) results in nearly complete abolition of oxygen uptake rate (33). The strain harboring these four mutations was named ECOM4 (*Escherichia coli* Cytochrome Oxidase Mutant 4). The ECOM4 strain was unable to undergo aerobic-anaerobic shift and exhibited similar phenotype under both conditions, making it suitable for use as a platform strain for the implementation and adaptation of strain designs. Comprehensive understanding of the metabolism and physiology of the platform strain is important as it provides insights for further engineering. Therefore, it is imperative to understand how the deletions reprogram the metabolic network of *E. coli*. To this end, we performed whole-genome transcriptome and fluxome analysis coupled with physiological characterization under both growth conditions.

Example 7

Materials and Methods Used in Examples 8-9

Strains and Media:

The strain described in this work was generated from the cytochrome oxidase mutant strain (ECOM3) presented before (33). The quinol monooxygenase (ygiN) (1) was removed from the unevolved ECOM3; the resulting strain harbored the following mutations: cydAB, cyoABCD, cbdAB, ygiN, and was named ECOM4 (*Escherichia Coli* Oxidase Mutant 4). The deletion of the ygiN gene was conducted using homologous recombination of a PCR-amplified linear fragment using lambda Red recombinase system (10). In short, the gene to be deleted was replaced by a kanamycin gene flanked by FRT sites and the insert was removed with a FLP recombinase. In order to verify the genotype of the mutant, single colonies were isolated from the solid media and tested with PCR. Primers used for the deletion and verification are presented in Table 10. Wild type (WT) *E. coli* colonies were tested in parallel as a negative control. Bacterial strains were cultured at 37° C. in M9 minimal liquid medium containing 4 gram/L glucose, except as noted.

Adaptive Evolution:

Mutant strains were adaptively evolved using the technique described earlier (14, 18). In short, a colony off a fresh agar plate was inoculated in 250 ml M9 medium containing EZ supplements (Teknova), grown overnight, and passed into a new flask containing fresh medium. The volume of inoculum was adjusted on a daily basis in order to maintain exponential phase growth. The amount of EZ supplements added to the medium was reduced exponentially during the first two weeks of evolution. Cells were propagated aerobically for 30 days (>500 generations) following the protocol reported by Fong et al. 2005 (14). Evolving cultures were also supplemented with 50 µg/ml kanamycin once a week and screened daily with PCR to prevent contamination. Samples were frozen every 2 days throughout the evolution.

Phenotype Assessment:

To assess phenotypic characteristics of evolved and isolated strains, growth rates and byproduct secretion profiles were measured. Each strain was grown in batch culture under oxic, and anoxic conditions. Aerobic cultivation was conducted in 500 ml Erlenmeyer flasks containing 250 ml M9 medium. Temperature was controlled by a circulating water bath, mixing and aeration was controlled with a stir bar at ~1000 rpm. Anaerobic cultivation was conducted in 250 ml Erlenmeyer flasks with 200 ml medium, sealed with rubber stoppers containing necessary inlet tubing. Anoxic conditions were achieved by continuously flushing of cultures with a 95% $N_2$/5% $CO_2$ gas mixture at a flow rate of 1 ml/min. The temperature was controlled by using a circulating water bath; mixing was controlled with a stir speed of ~200 rpm. Samples were taken from batch cultures periodically (every 30 min), filtered through a 0.2 µm filter and stored at −20° C. for by-product analysis. Glucose concentration in the media was assessed using an enzymatic assay kit (R-Biopharm), while D-lactate secretion was measured using RI (refractive index) detection by HPLC (Waters) with a Bio-Rad Aminex HPX87—H ion exclusion column (injection volume, 10 µl) and 5 mM $H_2SO_4$ as the mobile phase (0.5 ml/min, 45° C.). The identities of metabolites and organic acids in the fermentation broth were further verified with enzymatic kits (R-Biopharm). The oxygen uptake rate of each aerobic culture was determined by measuring the rate of dissolved oxygen depletion in an enclosed respirometer chamber using a polarographic dissolved oxygen probe (YSI).

Clonal Analysis:

ECOM4 populations evolved for 30 days were cultured overnight on solid M9 media with 4 gram/1 glucose and 50 µg/ml kanamycin. Ten random individual colonies were selected from each plate and grown overnight in M9 liquid medium. Cells were harvested by centrifugation, washed three times with medium without a carbon source and loaded on a Bioscreen C machine (Growth Curves USA). Cultures were inoculated into 300 µl wells containing medium; the initial OD of each well was less than 0.05. Cells were grown for 8 hours with continuous shaking to ensure good mixing and aeration and optical density (OD at 600 nm) measurements were taken every 15 min. Once the cells reached stationary phase, the assay was stopped and D-lactate concentration was assessed by HPLC. Strains with the highest production yield were identified and subjected to aerobic batch cultivation. Strains were grown in 500 ml Erlenmeyer flasks with 250 ml medium for 8 hours with continuous agitation as described before. Samples were taken every 30 min, filtered and analyzed using HPLC (Waters). Growth rate (1/hr), oxygen uptake rate (mmol/g-dwt/hr), sugar uptake rate (mmol/g-dwt/hr), and product secretion rates (mmol/g-dwt/hr) were measured as described before.

Transcriptome Analysis:

Cultures were grown to mid-log growth phase aerobically, and anaerobically (OD A600~0.6 for MG1655 and OD A600~0.25 for mutant). The cultures (3 mL of MG1655 and 7 ml of mutant) were then added to 2 volumes of RNAprotect Bacteria Reagent (Qiagen) and total RNA was isolated by using RNeasy columns (Qiagen) with DNaseI treatment. Total RNA yields were measured by using a spectrophotometer (A260) and quality was checked by visualization on agarose gels and by measuring the sample A260/A280 ratio (>1.8). cDNA preparation was performed as described in Cho et al. (7). Affymetrix GeneChip $E.\ coli$ Genome 2.0 arrays were used for genome-scale transcriptional analyses. cDNA synthesis, fragmentation, end-terminus biotin labeling, and array hybridization were performed as recommended by Affymetrix standard protocols. Differentially expressed genes were selected by using fold-change threshold and student t-test with false discovery rate (FDR) correction as implemented in ArrayStar 3 software (DNAStar). Genes with at least two-fold expression level change and FDR-adjusted P-value of less than 0.05 were considered significant and were used for strain analysis. Transcriptome data was mapped to iAF1260 metabolic reconstruction of $E.\ coli$ (12), by using the Simpheny software platform (Genomatica). Microarray data sets have been deposited in the Gene Expression Omnibus (GEO) database (3, 11), and were assigned the following record number: GSE21839.

The probability of regulon and GO term enrichment among differentially expressed genes was computed using the hypergeometric distribution. Regulons were obtained from RegulonDB v6.0 (15) and GO terms from Ecocyc v12.0 (25, 26). Correction for multiple hypotheses was done as reported by Storey, et al. (39) (FDR=0.01). Consistency of differential expression with ArcA and FNR activity in their respective regulons was determined by comparing differential expression (up or down) with increased ArcA or FNR activity (activator or repressor) as reported by RegulonDB.

Quantitative PCR Analysis:

RNA purification and cDNA synthesis were conducted following the same protocol as described for the gene expression analysis. The 50 µl qPCR reaction contained 25 µl of SYBR Green Taq master mix (Qiagen), 0.2 µM forward primer, 0.2 µM reverse primer, and cDNA as a template. Each qPCR reaction was run in triplicates in a Bio-Rad thermocycler (Bio-Rad, Hercules) with the following settings: 95° C. for 15 min, 94° C. for 15 s, 52° C. for 30 s, 72° C. for 30 s; the denaturation, annealing and extension steps were repeated for 40 cycles. Targeted gene expression of the mutant strain was analyzed under oxic and anoxic growth and compared to WT.

Using a standard curve for each primer set, the relative cDNA quantity was obtained for each gene by normalizing it to the quantity of acpP (acyl carrier protein) cDNA in the same sample. acpP was chosen as the internal control gene since it is constitutively expressed in WT and mutant under both aerobic and anaerobic conditions (9).

$^{13}$C Tracing Studies:

Culture labeling: Prior to labeling, single colonies were selected from stock plates and inoculated directly into 250 ml M9 medium in 500 Erlenmeyer flasks aerated by stirring at 1000 rpm. Cells were grown overnight, harvested, washed twice with water and used to inoculate 50 ml flasks containing 25 ml medium with 2 g/L $^{13}$C-labeled D-glucose, with initial $OD_{600}$ 0.005-0.01. Glucose was supplied as either 100% 1-$^{13}$C-labeled, 100% 6-$^{13}$C-labeled, or a mixture of 20% uniformly (U-$^{13}$C—) labeled with 80% natural glucose (which is randomly 1% $^{13}$C). Cells were grown to mid-log phase, corresponding to OD600 of 0.6 (WT) or 0.25 (mutant). 3 ml (WT) or 10 ml (mutant) of each culture was harvested by centrifugation at 4° C. Media were aspirated and analyzed with HPLC to determine the remaining glucose concentration. Cell pellets were placed at −80° C. prior to further analysis.

Derivatization and GC-MS Analysis:

Cells were resuspended in 0.1 ml 6 M HCl, transferred to glass vials and protein was digested into amino acids under a nitrogen atmosphere for 18 hr at 105° C. in an Eldex H/D Work Station. Digested samples were dried to remove residual HCl, resuspended with 75 µl each tetrahydrofuran and N-tert-butyldimethylsilyl-N-methyltrifluoroacetamide (Aldrich), and incubated for 1 hr at 80° C. to derivatize amino acids. Samples were filtered through 0.2 µm PVDF filters, and injected into a Shimadzu QP2010 Plus GC-MS (0.5 µl with 1:50 split ratio). GC injection temperature was 250° C. and the GC oven temperature was initially 130° C. for 4 min, rising to 230° C. at 4° C./min and to 280° C. at 20° C./min with a final hold at this temperature for 2 min. GC flow rate with helium carrier gas was 50 cm/s. The GC column used was a 15 m×0.25 mm×0.25 µm SHRXI-5 ms (Shimadzu). GC-MS interface temperature was 300° C. and (electron impact) ion source temperature was 200° C., with 70 eV ionization voltage. The mass spectrometer was set to scan m/z range 50-600.

Processing of GC-MS Data:

Mass data were retrieved from the GC-MS for fragments of 14 derivatized amino acids: cysteine and tryptophan were degraded during amino acid hydrolysis; asparagine and glutamine were converted respectively to aspartate and glutamate; arginine was not stable to the derivatization procedure. For each fragment, these data comprised mass intensities for the base isotopomer (without any heavy isotopes, M+0), and isotopomers with increasing unit mass (up to M+6) relative to M+0. These mass distributions were normalized by dividing by the sum of M+0 to M+6, and corrected for naturally-occurring heavy isotopes of the elements H, N, O, Si, S, and (in moieties from the derivatizing reagent) C, using matrix-based probabilistic methods as described (31, 42) implemented in Microsoft Excel. Data were also corrected for carry-over of unlabeled inoculum (31).

Corrected mass distributions for amino acid fragments from U-$^{13}$C-glucose-labeled cells were used to infer the trafficking and reassortment through metabolism of linked chains of carbons derived from glucose, while mass distribution data from 1- or 6-$^{13}$C-glucose-labeled cells were used to track the fate of individual carbon atoms. The analysis is summarized here and is described in more detail in Supplementary Methods.

Amino acid labeling data originating from U-$^{13}$C-glucose was used to estimate two aspects of pentose phosphate pathway (PPP) flux. The mass distribution data for alanine (as a marker for pyruvate) were used to calculate the fraction of alanine originating from the PPP versus glycolysis. Flux from glucose via glucose-6-phosphate to pentose-5-phosphates (P5P; ribose-5-phosphate, xyulose-5-phosphate and ribulose-5-phosphate—all assumed to be in equilibrium) in the oxidative PPP and back to glycolytic intermediates in non-oxidative PPP ultimately yields 5 pyruvate molecules per 3 input glucose. Of these 5 pyruvate molecules, 3 are composed of 3-carbon units linked as they were in glucose (same as pyruvate produced via glycolysis); 2 are re-assorted such that C1 has a different origin from the rest of the molecule (41). The fraction of pyruvate split across the C1-C2 bond was calculated from the mass distributions of alanine fragments.

Secondly, histidine labeling from U-$^{13}$C-glucose was used to calculate relative input to P5P from oxidative or non-oxidative PPP. The carbon backbone of histidine is equivalent to P5P plus one carbon from the tetrahydrofolate-linked one-carbon (1-C) pool. Input to P5P from oxidative PPP removes the C1 carbon from glucose but otherwise the carbon backbone remains intact (giving an M+5 P5P fraction). In contrast, inputs from non-oxidative PPP necessarily yield re-assorted P5P, with the split between different source molecules being largely across the C2-C3 bond (yielding M+2 or M+3 P5P).

Data from 1-$^{13}$C-glucose labeling experiments were used to provide another measure of flux through PPP versus glycolysis. As noted above, glucose routed through the oxidative branch of the PPP loses carbon from position 1 as $CO_2$. Therefore, by measuring the degree of loss of $^{13}$C-label in alanine (pyruvate) in 1-$^{13}$C-glucose-labeled cells, relative flux through glycolysis versus PPP was calculated.

Mass data for U-$^{13}$C-glucose labeling of aspartate, which was assumed to be in equilibrium with oxaloacetate (OAA), were used to assess the relative inputs to OAA from the TCA cycle versus the anaplerotic reactions phosphoenolpyruvate carboxylase (PEPC) and malic enzyme. In broad terms, input from anaplerosis was apparent as +3 mass units labeling of aspartate, indicative of incorporation of linked [$^{13}$C] 3-carbon units arising from PEP or pyruvate, while input from the TCA cycle appeared as +2 mass units labeling indicative of input of 2-carbon units originating as acetyl-CoA. Data from various fragments of aspartate were used to calculate the backflux in the TCA cycle from oxaloacetate to symmetrical metabolites (i.e., fumarate), and the $^{13}$C labeling of cellular $CO_2$/bicarbonate. The $^{13}$C labeling pattern of anaplerotic input to oxaloacetate was then modeled as the product of $CO_2$ labeling and $^{13}$C labeling of alanine C1-3 (as a surrogate for pyruvate or PEP), while the input to oxaloacetate from α-ketoglutarate in the TCA cycle was assumed to correspond to the labeling of glutamate (C2-C5 fragment). The relative contributions of these inputs to oxaloacetate were then calculated using least-squares fit in MATLAB. These results were checked with alternate amino acid fragments providing the inputs (See Supplementary Methods).

1- or 6-$^{13}$C-glucose data were used to calculate relative flux from glucose to pyruvate through the Entner-Doudoroff (ED) pathway versus glycolysis or the PPP. The ED, in contrast to the latter pathways, converts 1-$^{13}$C-glucose to 1-$^{13}$C-pyruvate, and not 3-$^{13}$C-pyruvate. Flux through the ED was therefore estimated by comparing labeling of C1-3 and C2-3 fragments of alanine (13).

Positionally-labeled glucose data were also used to determine $^{13}$C-labeling of the 1-C pool, utilizing methionine and aspartate labeling data, as methionine is produced from aspartate plus a 1-C unit. Furthermore, the relative contributions of serine or glycine to the 1-C pool were determined, based on the labeling of the 3-position of serine and 2-position of glycine.

Quinone Extraction:

The ubiquinone-8 (UQ) and menaquinone (MQ) extraction was conducted according to the protocol outlined previously (4, 5, 36). In short, 2 ml of WT culture and 4 ml of ECOM4LA culture were quenched with 6 ml of ice cold methanol Next, 6 ml of petroleum ether were added rapidly and mixture was vortexed for 1 min Following centrifugation of the mixture (900×g, for 2 min), the top phase was transferred into a new tube. Another 3 ml of petroleum ether were added and the vortexing and centrifugation steps were repeated. The upper phases were combined and allowed to evaporate to dryness. Dried extracted quinones were resuspended in 100 μl of ethanol and analyzed using HPLC (Waters) system fitted with Pursuit XRs (Varian) C18 reverse phase column with methanol as a mobile phase and flow rate of 1.0 ml/min at ambient temperature. Detection of quinones was conducted using a dual-wavelength UV detector (Waters) with 290 nm for UQ and 248 nm for MQ (4, 36). Ubiquinone-10 and menaquinone-4 were used as standards. The total amount of each species was calculated using the relevant peak area, plotted against the molar absorption coefficient as described by Shestopalov et al. (36). Analytical grade methanol, petroleum ether, and ethanol were acquired from Sigma Aldrich.

Example 8

Results of Experiments from Example 7

Strain Engineering and Adaptive Evolution

The ECOM4 strain was constructed from the unevolved ECOM3 strain previously described by us (33). The ECOM4 strain was initially incapable of growing on M9 minimal medium and required amino acid supplementation for the robust growth. ECOM4 was adapted in culture to grow in unsupplemented M9 minimal media with glucose as the sole carbon source. Evolutionary trajectories for three populations are presented in FIG. 13A. After 30 days of adaptation, the average growth rate of the three evolved populations (ECOM41, ECOM42, and ECOM43) in minimal medium was nearly identical (within 5%) to the growth rate in supplemented medium prior to evolution (FIG. 13B). Lactate yield decreased slightly during growth adaptation. The evolved oxygen uptake rate (OUR) was nearly identical to the unevolved strain, at a level of 0.25+/−0.12 mmol/g-dwt/hr, and nearly 60 times lower than the OUR of WT *E. coli*. Detailed phenotypic data such as growth rate, glucose and oxygen uptake rates, and by-product secretion rates measured during evolution are presented in Table 11. In order to characterize and study heterogeneity in the evolved populations, we used clonal analysis (FIG. 7). A single clone (ECOM4LA) was selected from one of the three evolved populations (ECOM41) based on the highest lactate yield. The following experiments were performed in triplicates using the ECOM4LA clone.

Phenotypic Characterization Revealed Substantial Similarity Between Aerobic and Anaerobic ECOM4

The ECOM4LA strain was predicted to have a similar growth rate irrespective of the oxygen supply. Growth rates were comparable for aerobic and anaerobic conditions, being 0.32+/−0.02 1/hr and 0.27+/−0.06 1/hr, respectively. Similarly, the conversion of glucose to D-lactate was only slightly affected by oxygen supply, with yields of 98% and 92% for aerobic and anaerobic growth conditions (Table 7). Lactate was produced with 70% yield during the exponential phase and with nearly 100% yield during the stationary phase (FIG. 8); illustrating that 30% of carbon was directed towards biomass formation. Succinic acid was present in a low amount during the exponential growth phase and was metabolized in stationary phase. The highest measured concentration of succinate during the exponential phase was on the order of 30.0+/−15.0 mg/L; however, this measurement was highly variable due to re-uptake of succinate. Based on these results we hypothesized that the ECOM4LA strain might be using the anaerobic respiratory chain in order to remove the excess electrons during aerobic growth (see Discussion), while the majority of the electrons are removed by means of D-lactate production. Gene expression analysis was used to determine metabolic changes, and to decipher possible regulatory alterations that underlie the inability of ECOM4LA to undergo the normal aerobic-anaerobic shift.

Gene Expression Analysis Reveals a Shift to Anaerobic Metabolism in ECOM4LA Under Oxic Conditions Genome wide transcriptomic profiles were determined for the WT and ECOM4LA strains under aerobic and anaerobic conditions. Expressed genes were selected based on criteria described earlier (see Methods and Materials). The gene expression comparison between aerobic and anaerobic growth in WT *E. coli* revealed that 564 genes (13% of the genome—based on 4468 total genes in the *E. coli* genome (25, 26)) had significant changes in expression (FIG. 9). Comparison of mRNA transcript levels between ECOM4LA and WT under oxic growth conditions revealed that 538 genes were significantly affected, accounting for nearly 13% of the genome, similar to the previous comparison. Interestingly, we observed that only ~6% of the genome (250 genes) was affected by an aerobic-anaerobic shift in ECOM4LA cell line (FIG. 9). This observation suggested that the inability to utilize oxygen has a significant effect on global gene expression and regulation, which contributes significantly to the inability of ECOM4LA strain to undergo an aerobic-anaerobic shift.

Gene Ontology (GO) term enrichment was employed to identify biological processes that are enriched within differentially expressed genes between various experimental conditions. Interestingly, the WT aerobic-anaerobic shift and the aerobic WT/ECOM4LA comparison shared several enriched metabolic GO biological processes such as "aerobic respiration," "anaerobic respiration," "tricarboxylic acid cycle," "oxidation reduction," and "glycolysis" (Table 12). Moreover, in the comparison between WT and ECOM4LA under oxic conditions, most of the significantly enriched GO terms in the down-regulated genes were similar to the enriched terms in the WT aerobic-anaerobic shift (Table 13), and these were dominated by metabolic processes.

Since metabolic terms dominated in the differentially expressed genes, we mapped the transcriptomic data onto the *E. coli* metabolic network reconstruction (12). Central metabolism was analyzed in detail (i.e., glycolysis, TCA cycle, pentose phosphate pathway (PPP), and fermentative pathways). We considered the gene expression pattern acquired from aerobic and anaerobic growth in WT *E. coli* as a benchmark to which we compared gene expression in the ECOM4LA strain under similar conditions. We observed that during the aerobic-anaerobic shift, WT downregulated the TCA cycle and upregulated expression of certain enzymes involved in glycolysis and fermentative pathways such as formate, acetate, and succinate production (FIG. 14A). When examining differences between gene expression of the ECOM4LA strain and WT *E. coli* grown in an oxic environment, we noticed that the majority of genes involved in glycolysis were significantly upregulated, while genes involved in TCA cycle were downregulated in ECOM4LA (Table 8, FIG. 14B).

Similar expression patterns were observed between WT (anaerobic) and ECOM4LA (aerobic) compared to WT (aerobic) (FIG. 14A/B). These results suggest that the ECOM4LA strain relies on glycolysis under oxic growth conditions for energy generation through substrate level phosphorylation. This result might be attributed to deletions in respiratory chain genes and an inability to build a sufficient proton gradient to produce energy by ATP-synthase. Also upregulation of the anaplerotic reaction (from phosphoenolpyruvate to oxaloacetate) was observed in the ECOM4LA strain. We also noticed that the lactate dehydrogenase (ldhA) gene was upregulated over 3 fold similarly to what was observed earlier for the parent strain (33). Comparable, but less profound expression changes were observed in anaerobic ECOM4LA compared to aerobic WT (FIG. 14C). We observed significant downregulation of the TCA cycle and upregulation of some glycolytic enzymes, suggesting that similar regulatory mechanisms are active in this strain under both environmental conditions.

The most interesting result was observed when we mapped the gene expression of ECOM4LA strain during an aerobic-anaerobic shift. This comparison indicated no changes to central metabolism in ECOM4LA under oxic and anoxic conditions (FIG. 14D). The only gene that had almost a 2-fold increase in expression was fumarate reductase (frdABCD). Other significantly expressed genes mapped sparsely, without any definite pattern, onto the entire metabolic map in the iAF1260 metabolic model. The lack of more significant changes in gene expression between aerobic and anaerobic profiles for the ECOM4LA strain illustrates that functionalities of the central metabolism of respiratory deficient ECOM4LA strain has been reduced to perform similar functions under both studied growth conditions.

Gene Expression Suggests ArcA is Active in Aerobic ECOM4LA, while FNR is not

Figure 15:
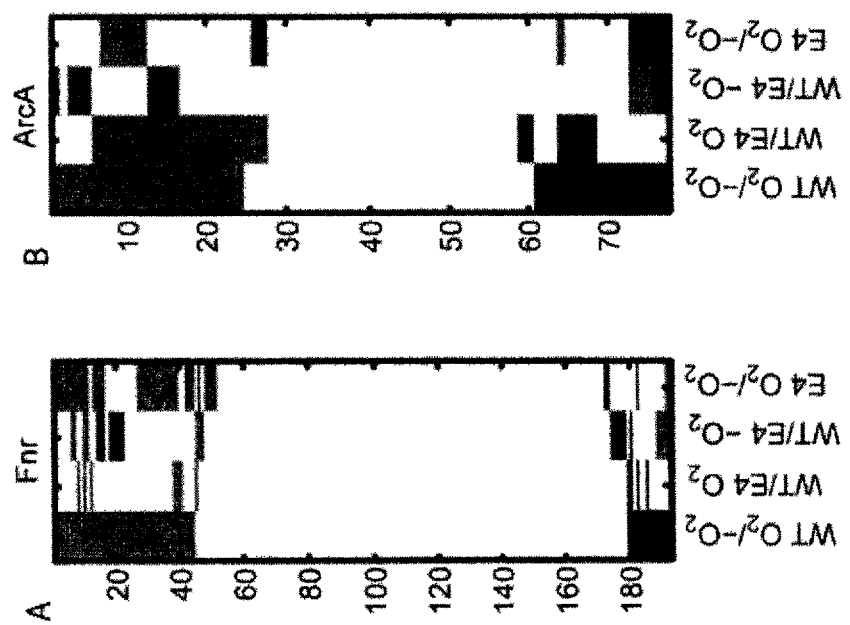
FIG. 15: Global gene expression suggests that ArcA is active in ECOM4LA in aerobic conditions. Gene expression changes for all genes that are known to be regulated by the anerobic regulators (a) FNR or (b) ArcA according to RegulonDB were compared to the reported function of the regulators (activator or repressor). If a gene was differentially expressed in the direction of known regulatory activity, then the expression change is said to be consistent (blue). If the gene expression change is in the opposite direction of regulator activity, it is shown in red. Since RegulonDB regulatory logic is partially inferred from microarray data for these transcription factors, some normal ArcA and FNR activity may be in the direction opposite from RegulonDB assignments. A: The FNR regulon showed greater differential expression and greater consistency (blue) for the WT aerobic-anaerobic shift, and the ECOM4LA aerobic-anaerobic shift. B: The ArcA regulon shows greater differential expression and greater consistency for the WT aerobic/anaerobic shift and in the comparison between aerobic WT and ECOM4LA; thereby suggesting that ArcA is active in ECOM4LA, even under aerobic growth.

Since differential expression of central metabolic genes is similar in ECOM4LA in comparison to anaerobically grown WT *E. coli*, we asked if this anaerobic behavior in ECOM4LA extended beyond its metabolism. *E. coli* has two different regulators that control expression of genes involved in the aerobic-anaerobic shift, consisting of the ArcB/ArcA two-component system and FNR. FNR is a transcriptional regulator whose activity is regulated directly by oxygen (22); The FNR regulon (from RegulonDB v 6.0) did not have more differentially expressed genes in the microarray data than expected by chance ($p=0.11$, hypergeometric test). Moreover, in the comparison between aerobic WT and ECOM4LA, less than 4% of the FNR regulon (excluding ArcA/FNR co-regulated genes) is differentially expressed in the direction consistent with FNR activity (FIG. 15A). In like manner, the comparison between WT and ECOM4LA under anoxic conditions also shows little difference. However, for both strains, the shift from aerobic to anaerobic conditions clearly causes gene expression changes in the FNR regulon consistent with known FNR activity of activation or repression (FIG. 15A), suggesting that FNR activity changes in the aerobic-anaerobic shift, but not between these two strains.

Conversely, the analysis of the ArcA regulon revealed significant differences between ECOM4LA and WT, but little ArcA-associated change in the ECOM4LA aerobic-anaerobic shift. When WT and ECOM4LA are compared, the ArcA regulon is enriched among the differentially expressed genes ($p=4.5 \times 10^{-12}$, hypergeometric test), which is the second most significantly enriched regulon for this condition (Table 13).

Moreover, in the WT aerobic-anaerobic shift, 71% of the differentially expressed ArcA regulon genes that are consistent with reported ArcA function (as an activator/repressor), also show the same consistency when comparing WT and ECOM4LA under aerobic conditions (FIG. 15B). Furthermore, differentially expressed genes between WT and ECOM4LA under aerobic conditions were consistent with known functions of ArcA (p=0.03, Fischer's exact test). Conversely, few genes in the ArcA regulon are significantly differentially expressed between anaerobic WT and ECOM4LA or between aerobic and anaerobic ECOM4LA, suggesting that ArcA activity is similar in these three scenarios. Together, these results show that gene expression changes are consistent with ArcA being active in ECOM4LA under aerobic conditions.

Quinone Pool is Dominated by Menaquinones in ECOM4LA Under Oxic Condition

The activation of ArcA under aerobic conditions may be due to the fact that ArcA is a part of a two-component regulatory system that responds to the redox state of the quinone pool (4). Since the aerobic respiratory chain cannot be utilized in ECOM4LA, the ubiquinone pool is diminished and complemented by menaquinones that are involved in the anaerobic respiration mechanism (from NADH to fumarate). Relative amounts of ubiquinone and menaquinone species present in actively growing ECOM4LA and WT under oxic and anoxic conditions were measured (FIG. 10). Consistent with previous reports, the quinone pool of the WT is dominated by ubiquinones during aerobic growth (800+/−60 nmol/g-dwt) and by menaquinones during anaerobic growth (650+/−80 nmol/g-dwt) (5). For the ECOM4LA strain we observed that the ubiquinone content varied between 150.0 and 200.0 nmol/g-dwt for anaerobic and aerobic conditions respectively, while menaquinones were present at a much higher concentration for both conditions (500.0+/−150.0 nmol/g-dwt for anaerobic and 450.0+/−100.0 nmol/g-dwt in aerobic conditions) (FIG. 10). Since ECOM4LA cannot utilize molecular oxygen, the quinone pool in the mutant strain has a completely different content with respect to WT. The ECOM4LA quinone pool is dominated primarily by menaquinones under both conditions. It has been shown that presence of ubiquinones inhibits activation of the ArcB/ArcA system, while abundance of menaquinones alleviates this inhibition leading to activation of ArcA (4).

These results suggest that the anaerobic phenotype of aerobically growing ECOM4LA is due to the activation of the ArcA regulon by a disruption in the cellular redox balance. Under oxic conditions, phosphorylated ArcA activates numerous operons involved in fermentative metabolism (6, 29) and represses operons involved in respiratory metabolism (17).

Targeted Gene Expression Measurements

In order to validate observed levels of gene expression, we used qPCR. Genes selected for qPCR analysis under oxic condition, in ECOM4LA as compared to WT, included: NADH: menaquinone oxidoreductase (yieF, wrbA), fumarate reductase (frdABCD), and succinate dehydrogenase (sdhABCD). qPCR analysis confirmed that yieF was upregulated nearly 10 fold, wrbA was upregulated over 40 fold and the frdABCD operon was upregulated over 50 fold in the aerobic ECOM4LA strain. We observed a significant downregulation (over 25 fold down) of sdh operon in aerobic ECOM4LA, which is similar to WT under anoxic conditions (over 30 fold down) (Table 15). These findings, together with observed downregulation of the TCA cycle, imply that the regulation in aerobic ECOM4LA cell line is similar to anaerobic WT E. coli.

Carbon Labeling Experiments

Gene expression analysis indicated major differences in the metabolism of ECOM4LA versus its WT E. coli parent when grown aerobically. To confirm this, metabolism was assayed directly by $^{13}C$ labeling of both strains under aerobic conditions. $^{13}C$ labeling was used to infer relative flux through different sections of central metabolism, particularly the pentose phosphate pathway (PPP), glycolysis, and the TCA cycle (Table 9).

Pentose Phosphate Pathway and Glycolysis

PPP versus glycolytic flux was calculated in two ways. First, it was estimated from labeling patterns of alanine produced from U-13C-glucose. Using the calculation of Szyperski (11) for the reassortment of intermediates in the non-oxidative branch of the PPP (leading to a reassortment of C1-C2 in pyruvate and therefore alanine), in WT a maximum 13% of pyruvate was formed from PPP. In ECOM4LA, the calculated percentage was −2% (or effectively zero; Table 9).

Similar values were found for flux through the PPP versus glycolysis using 1-$^{13}C$-glucose-generated data. Here, alanine labeling patterns were analyzed for loss of $^{13}C$ label consequent upon the loss of the labeled 1-carbon of glucose as $CO_2$ during transit through the oxidative branch of the PPP. This analysis yielded a value for PPP flux of 15% in WT and 2% in ECOM4LA, relative to glycolysis (Table 9, FIG. 16B). If it is assumed that all glucose taken up was channeled to glycolysis or the PPP, then the relative PPP flux can be converted to an absolute flux by multiplying these percentages by the measured glucose uptake rates (Table 7). This calculation gives values for PPP flux of 1.4 and 0.5 mmol/g-dwt/hr for WT and ECOM4LA, respectively.

A different perspective on the PPP was provided by analyzing histidine labeling from U-13C-glucose cultures. From histidine labeling patterns, it was possible to calculate relative inputs to the P5P pool (including ribose-5-phophate needed for RNA and DNA synthesis) from oxidative or non-oxidative PPP. In WT and ECOM4LA, respectively 19% and 13% of input to P5P was from oxidative PPP, with the balance from non-oxidative PPP (Table 9). The slightly stronger preference for non-oxidative PPP in ECOM4LA versus WT corresponds to generally enhanced expression of non-oxidative PPP genes in ECOM4LA versus WT, while expression of most of the non-oxidative PPP genes shows no difference (FIG. 14A/B).

Functioning of TCA Cycle

Amino acid labeling data from U-$^{13}C$-glucose-grown E. coli were used to determine the relative input of anaplerosis (via PEPC or malic enzyme) versus the TCA cycle to OAA (aspartate) (FIG. 16C, Table 9). WT E. coli were found to have a split input to OAA, ~40% from TCA cycle and 60% from anaplerotic reactions. This result is similar to that found before for WT E. coli strains growing in glucose minimal medium in aerated flasks (13, 41). In contrast, in the ECOM4LA strain, OAA was (within limits of error) exclusively synthesized by anaplerosis. This indicated that the TCA cycle was non-functional somewhere between oxoglutarate (glutamate) and OAA. The labeling patterns of aspartate fragments in ECOM4LA did indicate some recycling of oxaloacetate through the symmetrical TCA intermediate fumarate (and possibly also succinate) (Table 9), which would indicate a break in the cycle closer to oxoglutarate. These measurements corresponded to the gene expression results, which showed that in the ECOM4LA relative to WT, expression of almost all of the TCA cycle enzymes was lower; while expression of the anaplerotic enzyme phosphoenolpyruvate carboxykinase was greater (FIG. 14B).

Other Pathways

The ED pathway was evaluated as an alternate route to pyruvate from glucose. Although expression of genes encoding the ED pathway are usually weak in *E. coli* grown on glucose (30), it was previously shown that *E. coli* mutants which were disabled in components of the TCA cycle (Sdh/Mdh or FumA) produced ~20% of their pyruvate via the ED pathway (13). Calculating the ED flux (versus glycolysis plus PPP) (13), we found that it was insignificant (Table 9) and certainly was not relatively more important in the TCA-nonfunctional ECOM4LA mutant. This corresponded to a lack of enhancement in gene expression for enzymes in the ED pathway (FIG. 14B).

Using $1\text{-}^{13}C\text{-}$ or $6\text{-}^{13}C$-glucose data, the degree of labeling of the 1-C pool was calculated from aspartate and methionine labeling (the latter being equivalent in its origins to aspartate plus a 1-C unit). For both *E. coli* strains cultured with $6\text{-}^{13}C$-glucose, 1-C pool labeling was slightly below 50% (Table 9), but was less with $1\text{-}^{13}C$-glucose, reduced (relative to $6\text{-}^{13}C$-glucose labeling) by 20% for WT and 3% for ECOM4LA. These reduced labeling levels reflected loss of label from glucose routed through the oxidative PPP before conversion to serine and thence into the 1-C pool, and corresponded roughly to the relative flux through this pathway calculated from $1\text{-}^{13}C$-glucose-labeled alanine data (Table 9). From fragment data for serine and glycine, the percent $^{13}C$ labeling at serine-3 or glycine-2 was calculated, and from this (assuming that these were the only two sources for the 1-C pool) the contribution of each to the 1-C pool. In all cases, serine-3 was the predominant precursor (Table 9).

Endogenous Sources of $CO_2$

Data from $U\text{-}^{13}C$-glucose labeling experiments indicated that most of the $CO_2$/bicarbonate used in anaplerotic reactions was derived from glucose and not from atmospheric $CO_2$ (Table 9). In ECOM4LA, 70% of $CO_2$ was from glucose versus 90% in WT. $CO_2$ labeling in both strains with $1\text{-}^{13}C$ was similar (Table 9), accounting for ~10% endogenous $CO_2$ in both cases. The lesser PPP flux in ECOM4LA (albeit relative to glycolysis) suggested that in this strain the 1-carbon of glucose might be converted to $CO_2$ via additional pathways. As the 1-position of glucose is equivalent to the 6-position after conversion by glycolysis to 3-carbon metabolites, labeling was also performed with $6\text{-}^{13}C$ glucose. This yielded no $CO_2$ labeling in either WT or ECOM4LA, demonstrating that in both strains oxidative PPP was the only route to convert the 1-carbon of glucose into $CO_2$.

Example 9

Discussion of Experiments of Example 8

The aim of this work was to gain insights into the physiology of the ECOM4 strain and understand what metabolic and regulatory changes led to the inability to switch metabolism between aerobic and anaerobic growth. Three active cytochrome oxidases and quinol monooxygenase were completely removed in order to produce a phenotype almost incapable of oxygen utilization. The oxygen uptake rate of the resultant mutant was reduced by nearly 60 times compared to un-mutated *E. coli*. As a consequence of these deletions, the mutant strain was unable to undergo an aerobic-anaerobic shift and presented fermentative behavior under oxic and anoxic conditions. In order to understand metabolic changes that underlie the unique physiology of the mutant strain, we conducted whole genome transcriptomics analysis coupled with $^{13}C$ tracing experiments and physiological characterization during aerobic and anaerobic growth.

The transition between oxic and anoxic environments has been studied extensively in *E. coli* (9, 17, 37). In particular, the "shift" between aerobic and anaerobic modes of metabolism is regulated by two distinct systems of transcription factors: FNR and ArcB/ArcA (2, 8, 24, 34, 35, 38). It has been reported that FNR is able to sense oxygen directly (40), while the ArcB/ArcA system responds to the content of the quinone pool (4, 5, 16), and switches on the expression of fermentation genes and represses aerobic pathways when *E. coli* encounters low oxygen growth conditions (19, 20).

Here we hypothesized that oxygen uptake-mediated regulation (ArcB/ArcA) will be significantly perturbed as a result of the inability to utilize oxygen, while oxygen sensing regulation (FNR) would exhibit similar behavior as in the wild type. Consistent with our hypothesis we observed activation of ArcA regulator under oxic conditions, and consequently activation of fermentative metabolism during aerobic growth, while the regulatory action of the FNR regulator remained similar to wild type.

Aerobic ECOM4LA Shows Anaerobic Gene Expression

The deletion of the respiratory chain components had a greater effect on metabolism in an oxic environment. Comparable gene expression patterns between the aerobic ECOM4LA and anaerobic WT not only indicate similar regulation but also suggest similar metabolic functions. In particular, high flux (based on uptake and secretion rates) and increased expression of glycolytic enzymes suggest that glycolysis is a main energy producing pathway in ECOM4LA during aerobic and anaerobic growth, similar to that seen in WT anaerobic growth. It is possible that ECOM4LA is unable to build a sufficient proton gradient due to mutations in cytochrome oxidases, thus requiring the production of ATP molecules by substrate-level phosphorylation under oxic growth conditions. The similarity of growth rates between aerobically grown ECOM4LA and anaerobically grown WT *E. coli* (Table 7) suggests that energy requirements are similar in both strains under given conditions, unlike that of aerobically and anaerobically grown WT *E. coli*.

Aerobic ECOMLA4 Uses Anaerobic Respiration

Figure 17:
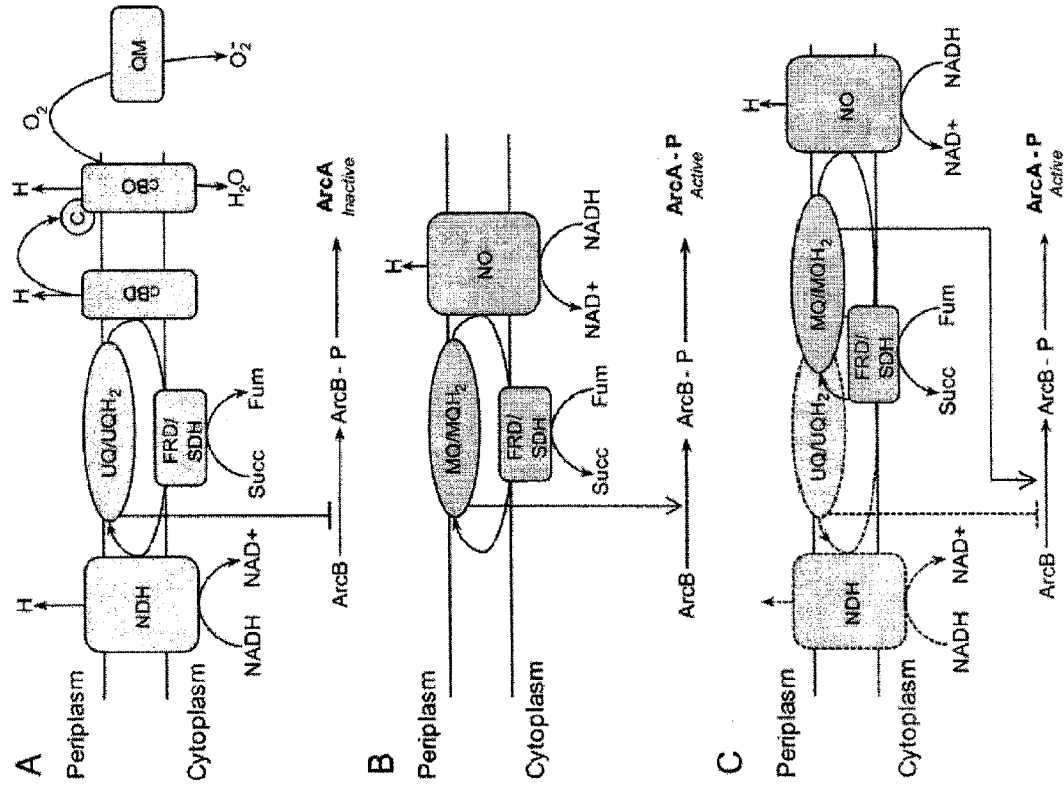
FIG. 17: Respiratory chain rearrangements in ECOM4LA strain compared to MG1655 and the effect of the content of the quinone pool on ArcA activity. A—A classical view on aerobic respiratory chain (red) in wild type *E. coli* (23, 25, 26). Electrons are transferred from NADH to oxygen via ubiquinone pool. An alternative oxygen utilization system through quinone monooxygenase (YgiN) is presented. High content of ubiquinones (UQs) represses the activity of ArcA regulator. B—A classical view of anaerobic respiratory chain (blue) in wild type *E. coli*. Electrons are transferred from NADH to succinate via menaquinone pool. High content of menaquinones (MQs) activates AcrA activity. C— A rearrangement in respiratory chain resulted from gene deletions. Lack of significant activity of aerobic respiration (dashed line) and increase in activity of anaerobic respiration (solid line) resulted in re-formulation of the quinone pool. Shift from UQs to MQs resulted in activation of ArcA regulator under oxic and anoxic conditions.

It is well known that *E. coli* has a highly versatile respiratory chain that allows it to adapt to conditions that vary with respect to oxygen availability and the redox state (FIG. 17A, B) (5). It is possible that mutations introduced in the ECOM4LA strain, together with adaptive evolution, resulted in the rearrangement of the respiratory chain and a shift in the content of the quinone pool (FIG. 17C). During anaerobic growth, *E. coli* uses different respiratory pathways as compared to during aerobic growth (32). In the respiratory chain formed by NADH menaquinone oxidoreductase (yieF and wrbA) and fumarate reductase (frdABCD) electrons are transferred from NADH to fumarate by a menaquinone pool (43), resulting in the formation of succinate (FIG. 17C) (21). Based on our gene expression results and physiological observations we conclude that anaerobic respiration consisting of yieF/wrbA and frdABCD is active and used is to remove excess electrons during exponential growth of the ECOM4LA strain.

Anaerobic Regulator ArcA is Active in ECOM4LA During Oxic Growth

*E. coli* has two distinct regulators that control expression of the many genes involved in the aerobic-anaerobic shift: the ArcB/ArcA two-component system and FNR. In the expression data, we saw that ArcA activation in ECOM4LA is likely responsible for the anaerobic phenotype under aerobic conditions. However, there was a small number of ArcA targets (19 out of 143; see Table 14) that were further changed in the anaerobic ECOM4LA, consistent with known ArcA activity.

Thus, it seems that ArcA still increases its level of activity slightly in the ECOM4LA aerobic-anaerobic shift. To further validate activation of ArcA in ECOM4LA during aerobic growth we looked at genes previously identified as direct targets of ArcA regulation. We observed significant down-regulation of succinate dehydrogenase (shdABCD) and fad operon under oxic conditions, which is known to be repressed by ArcA. These operons were also repressed significantly under anoxic conditions, indicating activity of ArcA during anaerobic growth consistent with WT E. coli. Our results suggest that the action mode of one of the global transcription regulators (ArcA) has been altered as a result of major metabolic adjustment, which affected the gene expression in a non-intuitive way. In particular, the inability to utilize oxygen has led to a decrease in ubiquinone content and an increase in menaquinone content (FIG. 10) leading to the activation of the ArcB/ArcA regulatory system (4). Thus, the change in a composition of the quinone pool (FIG. 17C) leads to activation of ArcA and subsequent activation of fermentative metabolism during aerobic and anaerobic growth of the ECOM4LA cell line.

$^{13}$C Analysis Complements Gene Expression Data

Figure 16:
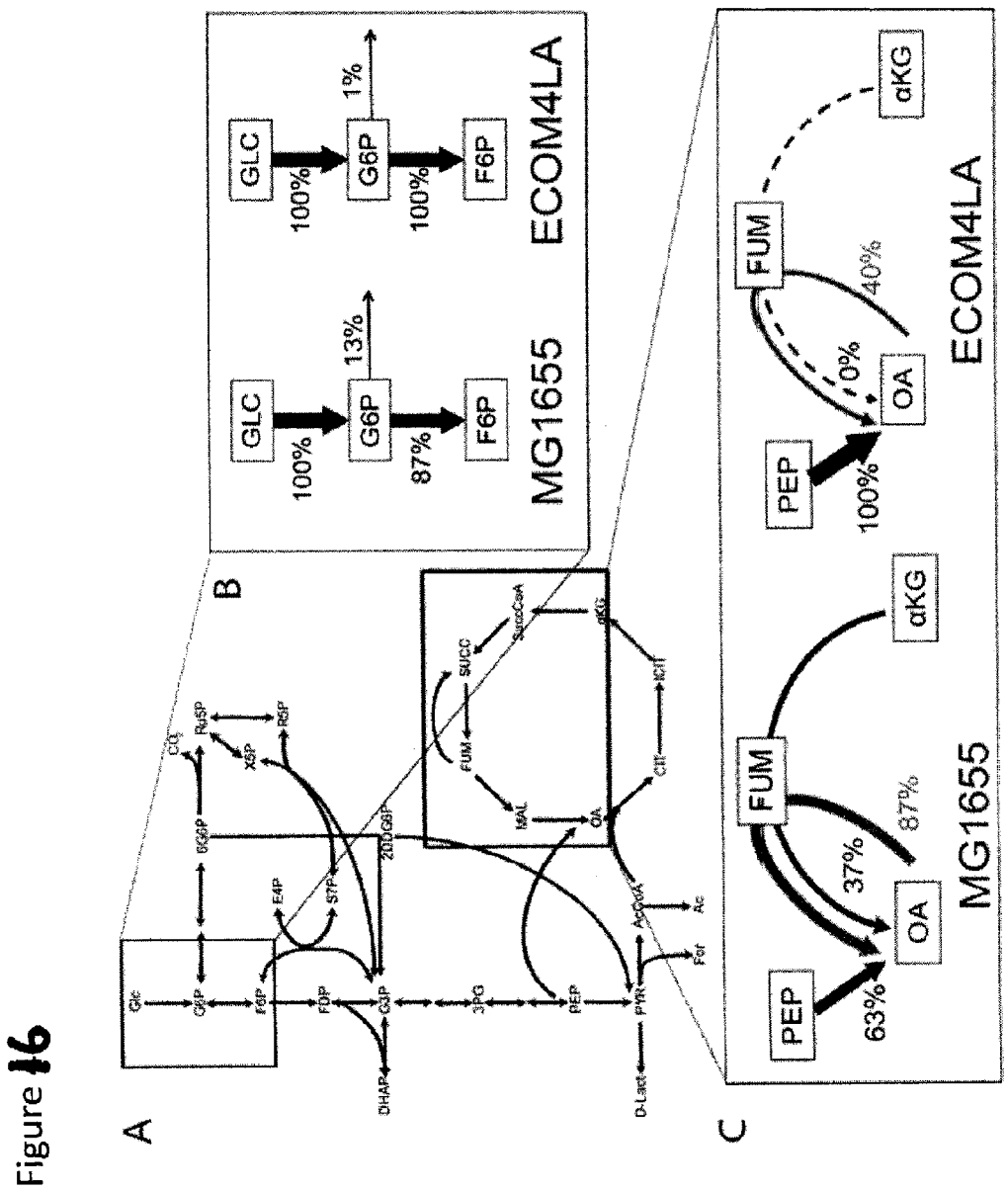
FIG. 16: Metabolic flux distribution through branching areas of the central metabolism of MG1655 and ECOM4LA cell lines. A—Overall metabolic map of central metabolism with branching areas of metabolism boxed. Corresponding gene expression is presented in FIG. 2. B—Relative input to glycolysis (F6P) from glucose-6-phosphate (G6P) vs. pentose phosphate pathway in each strain (based on U-$^{13}$C-glucose labeling data); C—Relative input to oxaloacetate (OA) from α-ketoglutarate (αKG) in the TCA cycle or from PEP via PEP carboxylase. Also shown in red is the fraction of OA formed from PEP that recycled through fumarate (FUM) in each strain.

Metabolic flux calculations based on $^{13}$C glucose labeling data were highly consistent with the gene expression data. Most notably, glycolysis was upregulated in ECOM4LA compared with the PPP, and flux through the TCA cycle was not detectable (FIG. 16). Flux analysis indicated reduced PPP flux between glucose and pyruvate not just relative to glycolysis, but also with conversion to absolute flux using glucose uptake rates. This contrasted with gene expression data (FIG. 14B) which showed greater expression of genes for the non-oxidative PPP in ECOM4LA. However, the reversibility of the reactions catalyzed by the enzymes in the non-oxidative PPP should be noted. Data for input into the P5P pool via the two branches of the PPP showed a greater contribution of the non-oxidative PPP in ECOM4LA (Table 9), which might account for the increased expression of the genes for this branch of the pathway here. Producing P5P via a non-reducing route might help ECOM4LA maintain its redox balance in the absence of the ability to utilize oxygen.

Similar Physiological Behavior Under Oxic and Anoxic Conditions

Even though we observed a nearly 15% difference in growth rate of ECOM4LA between oxic and anoxic conditions, the overall physiological behavior was similar (Table 7). Lower lactate yield observed during anaerobic growth can be attributed to a higher cell density. ECOM4LA strain grew to a 20% higher cell density anaerobically than aerobically (data not shown). Oxygen uptake rate measured after gene deletions was nearly 60 times lower than in wild type. We were unable to identify the metabolic function accounting for the remaining oxygen uptake; however, since no major physiological differences were observed under oxic and anoxic conditions, we can conclude that oxygen does not have a significant metabolic function in the ECOM4LA strain.

TABLE 7

Phenotypic characteristics of ECOM4LA strain under oxic and anoxic conditions.

|  | ECOM4LA + $O_2$ | ECOM4LA − $O_2$ | MG1655 + $O_2$ | MG1655 − $O_2$ |
| --- | --- | --- | --- | --- |
| Growth Rate (1/hr) | 0.32 +/− 0.005 | 0.27 +/− 0.006 | 0.71 +/− 0.01 | 0.45 +/− 0.02 |
| Glucose Uptake Rate (mmol/g-dwt/hr) | 26.4 +/− 0.09 | 24.9 +/− 0.72 | 9.02 +/− 0.23 | 17.3 +/− 0.17 |
| Lactate Secretion Rate (mmol/g-dwt/hr) | 48.6 +/− 0.76 | 41.58 +/− 1.58 | 0 | 0.95 +/− .008 |
| Acetate Secretion Rate (mmol/g-dwt/hr) | 0 | 0 | 3.37 +/− 0.9 | 10.3 +/− 0.60 |
| Oxygen Uptake Rate (mmol/g-dwt/hr) | 0.21 +/− 0.16 | 0 | 16.49 +/− 0.67 | 0 |
| Lactate/Glucose (gram/gram) | 0.98 +/− 0.07 | 0.92 +/− 0.04 | NA | NA |

TABLE 8

Comparison between gene expression levels in ECOM4LA and MG1655 cells grown aerobicaly and anaerobically.

| | | | Fold Change (adj. P-value)† | | | |
| --- | --- | --- | --- | --- | --- | --- |
| Gene Name | Locus Number | Product | E4/WT +O2 | E4/WT −O2 | WT −O2/+O2 | E4 +O2/−O2 |
| pgi | b4025 | Phosphoglucose Isomerase | 3.87 (0.017) | NC | NC | NC |
| pfkAB* | b3916 | 6-Phosphofructo Kinase | 2.04 (0.003) | NC | 2.29 (0) | NC |
| fbaA | b2925 | Fructose Bisphosphate Aldolase | 3.00 (0.01) | NC | NC | NC |
| fbaB | b2097 | Fructose Bisphosphate Aldolase | 8.77 (0) | 3.30 (0) | 3.23 (0) | NC |
| tpiA | b3919 | Triose Phosphate Isomerase | 3.33 (0.005) | NC | NC | NC |
| gapA | b1779 | Glyceraldehyde 3-Phosphate | 4.53 (0.02) | NC | 2.53 (0.05) | NC |
| pgk | b2926 | Phosphoglycerate Kinase | 2.10 (0.02) | NC | NC | NC |
| eno | b2779 | Enolase | 3.31 (0.008) | NC | NC | NC |
| ldhA | b1380 | D-Lactate Dehydrogenase | 3.36 (0.005) | NC | NC | NC |
| yieF | b3713 | NADH: Menaquinone Oxydoreductase | 2.47 (0.014) | 2.09 (0.001) | NC | 1.60 (0.023) |
| wrbA | b1004 | NADH: Menaquinone Oxydoreductase | 9.10 (0.002) | 3.22 (0.001) | 5.07 (0.003) | NC |
| frdABCD* | b4151-b4154 | Fumarate Reductase | 3.60 (0.02) | NC | 4.03 (0.002) | 1.90 (0.02) |
| sdhABCD* | b0721-b0724 | Succinase Dehydrogenase | −25.35 (0) | NC | −33.50 (0) | NC |
| nuoA - N* | b2288-b2276 | NADH: Ubiquinone Oxydoreductase | −2.10 (0.005) | NC | −2.30 (0.001) | NC |

†Benjamini-Hochberg false discovery rate-adjuster P value. Fold changes <2 fold were considered as no change (NC);
*average expression value is presented for large operons. E4—ECOM4LA strain, WT—wild type MG1655.

TABLE 9

Physiological parameters inferred from 13C labeling data

| | Data used: glucose substrates labeled amino acids | | WT | ECOM4 |
|---|---|---|---|---|
| Input to oxaloacetate: anaplerosis versus TCA cycle[1] | U-13C-glucose ASP, ALA, GLU | Anaplerosis TCA cycle | 62.4 ± 0.5% 37.6 ± 0.5% | 99.5 ± 1.4% 0.5 ± 1.4% |
| Recycling of oxaloacetate to/from fumarate/succinate[2] | U-13C-glucose ASP | | 86.7 ± 4.9% | 39.2 ± 0.6% |
| $CO_2$ labeling[3] | U-, 1- or 6-13C-glucose ASP | U-13C-glucose 1-13C-glucose 6-13C-glucose | 19.1 ± 0.2% 11.2 ± 1.8% 1.7 ± 2.4% | 14.5 ± 1.3% 9.3 ± 0.4% −0.2 ± 0.5% |
| PPP to pyruvate/alanine[4] | U-13C-glucose ALA | | 13.2 ± 1.7% | −2.8 ± 1.3% |
| Oxidative PPP[5] | 1-13C-glucose ALA | | 15.1 ± 1.2% | 1.7 ± 0.5% |
| Oxidative/Non-oxidative PPP into ribose | U-13C-glucose HIS | Oxidative PPP Non-oxidative PPP | 19.2 ± 1.6% 80.8 ± 1.6% | 13.2 ± 0.6% 86.8 ± 0.6% |
| 1-C pool labeling | 1- or 6-13C-glucose MET, ASP | 1-13C-glucose 6-13C-glucose | 37.3 ± 0.5% 46.8 ± 0.2% | 46.8 ± 0.4% 48.2 ± 0.1% |
| Origins of 1-C pool | 1- or 6-13C-glucose SER, GLY, MET, ASP | From serine (1-13C glucose) From serine (6-13C glucose) From glycine (1-13C glucose) From glycine (6-13C glucose) | 93.6 ± 2.4% 91.9 ± 0.1% 6.4 ± 2.4% 8.1 ± 0.1% | 97.5 ± 1.9% 98.8 ± 0.4% 2.5 ± 1.9% 1.2 ± 0.4% |
| Entner-Doudoroff[6] | 1- or 6-13C-glucose ALA | 1-13C-glucose 6-13C-glucose | 1.4 ± 1.0% 1.0 ± 0.2% | 0.1 ± 0.7% 0.3 ± 1.0% |

Data are mean ± SD from determinations on amino acids prepared from 3 separate cultures (mean ± range from 2 separate cultures for 6-$^{13}$C-glucose labeling).
[1] Anaplerosis via phospho-enol pyruvate carboxylase or malic enzyme.
[2] This is a measure of re-orientation of oxaloacetate after cycling through symmetrical intermediates (succinate and fumarate) and does not include oxaloacetate derived from TCA cycle as this portion of the oxaloacetate pool is by default randomly oriented as it is derived from succinate and fumarate.
[3] For U-$^{13}$C-glucose, maximum possible is 21% (from 20% U-$^{13}$C-glucose and 1% natural label). For 1- or 6-$^{13}$C, potential maximum 100% from 100% labeled glucose as sole carbon source.
[4] Relative to glycolysis.
[5] Measured by loss of label into alanine (pyruvate). Relative to glycolysis.
[6] Flux through Entner-Doudoroff pathway relative to other routes from glucose to pyruvate/alanine.

TABLE 10

DNA primers used for the deletion of ygiN

| Deletion Primers | Forward Primer (5'-->3') | Reverse Primer (5'-->3') |
|---|---|---|
| ygiN | SEQ ID NO: 24 ATGCTTACCGTAATCGCAGAA ATCCGTACTCGTCCTGGTCGT GTAGGCTGGAGCTGCTTC | SEQ ID NO: 25 TTAAATCCCTGGCTGCAGAATACGGA TATTCATCTCCAGCATTCCGGGGATC CGTCGACC |

| Conformation primers | Forward Primer (5'-->3') | Reverse Primer (5'-->3') |
|---|---|---|
| ygiN | SEQ ID NO: 26 CCGACATTTATCGCTAATGA | SEQ ID NO: 27 GTTGCAAGAGAAAGGCGACA |

TABLE 11

Physiological characteristics during 30 day adaptive evolution of ECOM4 strains

| | ECOM4 + $O_2$ day 0 | ECOM4 − $O_2$ day 0 | ECOM41 day 1 | ECOM42 | ECOM43 | ECOM41 day 10 | ECOM42 |
|---|---|---|---|---|---|---|---|
| GR | 0.38 +/− 0.02 | 0.44 +/− 0.01 | 0.36 +/− 0.01 | 0.36 +/− 0.02 | 0.35 +/− 0.08 | 0.06 +/− 0.01 | 0.07 +/− 0.01 |
| SUR | 19.79 +/− 0.6 | 16.49 +/− 1.53 | 18.73 +/− 0.51 | 18.5 +/− 0.35 | 19.5 +/− 0.24 | 11.42 +/− 0.04 | 9.61 +/− 0.12 |
| LactSR | 37.61 +/− 0.9 | 1.75 +/− 0.61 | 36.28 +/− 0.90 | 35.52 +/− 1.24 | 37.35 +/− 0.98 | 22.21 +/− 0.46 | 18.11 +/− 0.58 |
| Lact/Gluc | 0.80 | 0.06 | 0.96 | 0.95 | 0.98 | 0.92 | 0.93 |
| AcSR | 0.00 | 21.12 +/− 0.41 | 0.00 | 0.00 | 0.00 | 0.00 | 0.00 |
| OUR | 0.31 +/− 0.15 | NA | 0.27 +/− 0.1 | 0.35 +/− 0.14 | 0.36 +/− 0.09 | 0.15 +/− 0.02 | 0.17 +/− 0.08 |
| EZ | + | + | + | + | + | +/− | +/− |

| | ECOM43 day 10 | ECOM41 | ECOM42 day 20 | ECOM43 | ECOM41 | ECOM42 day 30 | ECOM43 |
|---|---|---|---|---|---|---|---|
| GR | 0.08 +/− 0.02 | 0.25 +/− 0.05 | 0.21 +/− 0.03 | 0.26 +/− 0.01 | 0.33 +/− 0.05 | 0.32 +/− 0.03 | 0.38 +/− 0.01 |
| SUR | 10.35 +/− 0.09 | 24.7 +/− 0.15 | 18.34 +/− 0.21 | 14.61 +/− 2.64 | 26.51 +/− 0.50 | 20.71 +/− 0.21 | 17.26 +/− 0.09 |

TABLE 11-continued

Physiological characteristics during 30 day adaptive evolution of ECOM4 strains

| LactSR | 20.74 +/− 0.32 | 41.71 +/− .10 | 25.71 +/− 1.24 | 7.47 +/− 3.61 | 43.78 +/− 0.12 | 26.58 +/− .47 | 9.58 +/− 2.40 |
|---|---|---|---|---|---|---|---|
| Lact/Glue | 0.90 | 0.89 | 0.73 | 0.31 | 0.85 | 0.65 | 0.48 |
| AcSR | 0.00 | 0.00 | 0.00 | 10.82 | 0.00 | 0.00 | 12.54 |
| OUR | 0.12 +/− 0.05 | 0.24 +/− 0.1 | 0.22 +/− 0.08 | 0.28 +/− 0.12 | 0.25 +/− 0.12 | 0.30 +/− 0.1 | 0.38 +/− 0.15 |
| EZ | +/− | − | − | − | − | − | − |

TABLE 12

Enrichment of Gene Ontology biological process terms in the differentially expressed genes

| GO # | Description | # in GO class | # Diff Exp in Data | Enrichment pValue |
|---|---|---|---|---|
| Table 12 - Part 1: Gene Ontology (GO) terms enriched in genes that are differentially expressed in aerobic ECOM4 when compared to aerobic wild-type (WT) | | | | |
| GO0055114YesEnrich | oxidation reduction | 324 | 81 | 7.99567E−09 |
| GO0009060YesEnrich | aerobic respiration | 21 | 14 | 3.13303E−08 |
| GO0006099YesEnrich | tricarboxylic acid cycle | 22 | 14 | 7.54378E−08 |
| GO0000105YesEnrich | histidine biosynthetic process | 11 | 8 | 1.30671E−05 |
| GO0000103YesEnrich | sulfate assimilation | 6 | 5 | 0.000249306 |
| GO0001101YesEnrich | response to acid | 4 | 4 | 0.000345037 |
| GO0006835YesEnrich | dicarboxylic acid transport | 4 | 4 | 0.000345037 |
| GO0019402YesEnrich | galactitol metabolic process | 4 | 4 | 0.000345037 |
| GO0009061YesEnrich | anaerobic respiration | 35 | 13 | 0.000414797 |
| GO0006096YesEnrich | glycolysis | 23 | 10 | 0.000448062 |
| GO0006810YesEnrich | transport | 665 | 118 | 0.000677485 |
| Table 12 - Part 2: Gene Ontology (GO) terms enriched in genes that are differentially expressed in anaerobic wild-type (WT) when compared to aerobic wild-type (WT) | | | | |
| GO0009061YesEnrich | anaerobic respiration | 35 | 24 | 1.98397E−13 |
| GO0001539YesEnrich | ciliary or flagellar motility | 28 | 28 | 1.07914E−12 |
| GO0055114YesEnrich | oxidation reduction | 324 | 101 | 2.48179E−12 |
| GO0022900YesEnrich | electron transport chain | 92 | 40 | 4.44966E−12 |
| GO0006099YesEnrich | tricarboxylic acid cycle | 22 | 17 | 3.06164E−11 |
| GO0006935YesEnrich | chemotaxis | 20 | 16 | 4.17291E−11 |
| GO0009060YesEnrich | aerobic respiration | 21 | 16 | 1.63127E−10 |
| GO0009296YesEnrich | flagellum biogenesis | 11 | 10 | 2.3897E−08 |
| GO0006826YesEnrich | iron ion transport | 36 | 19 | 3.28246E−08 |
| GO0006810YesEnrich | transport | 665 | 136 | 1.92963E−07 |
| GO0006113YesEnrich | fermentation | 5 | 5 | 5.07727E−05 |
| GO0009082YesEnrich | branched chain family amino acid biosynthetic process | 16 | 9 | 8.28667E−05 |
| GO0009098YesEnrich | leucine biosynthetic process | 6 | 5 | 0.000269664 |
| GO0006537YesEnrich | glutamate biosynthetic process | 6 | 5 | 0.000269664 |
| GO0042128YesEnrich | nitrate assimilation | 18 | 9 | 0.000271483 |
| GO0006811YesEnrich | ion transport | 94 | 26 | 0.000294123 |
| GO0019464YesEnrich | glycine decarboxylation via glycine cleavage system | 4 | 4 | 0.000367989 |
| GO0043064YesEnrich | flagellum organization and biogenesis | 4 | 4 | 0.000367989 |
| GO0019402YesEnrich | galactitol metabolic process | 4 | 4 | 0.000367989 |
| GO0042938YesEnrich | dipeptide transport | 4 | 4 | 0.000367989 |
| GO0022904YesEnrich | respiratory electron transport chain | 9 | 6 | 0.000403686 |
| GO0006096YesEnrich | glycolysis | 23 | 10 | 0.000511536 |
| GO0042773YesEnrich | ATP synthesis coupled electron transport | 10 | 6 | 0.000891174 |
| GO0015031YesEnrich | protein transport | 46 | 15 | 0.000907326 |

TABLE 13

Enrichment of Gene Ontology (GO) biological process terms in the down regulated genes in aerobic ECOM4 or anaerobic wild-type (WT) strain

| GO # | Description | # in GO class | # Diff Exp in Data | Enrichment pValue |
|---|---|---|---|---|
| Table 13 - Part 1: Gene Ontology (GO) terms enriched in genes that are down regulated in aerobic ECOM4 when compared to aerobic wild-type (WT) | | | | |
| GO0009060YesEnrich | aerobic respiration | 21 | 13 | 3.94E−12 |
| GO0006810YesEnrich | transport | 665 | 73 | 6.25E−12 |
| GO0006099YesEnrich | tricarboxylic acid cycle | 22 | 13 | 6.29E−12 |
| GO0006865YesEnrich | amino acid transport | 66 | 15 | 4.63E−07 |
| GO0006811YesEnrich | ion transport | 94 | 18 | 5E−07 |
| GO0055114YesEnrich | oxidation reduction | 324 | 35 | 5.94E−06 |
| GO0006826YesEnrich | iron ion transport | 36 | 10 | 5.94E−06 |
| GO0022900YesEnrich | electron transport chain | 92 | 16 | 8.3E−06 |
| GO0009061YesEnrich | anaerobic respiration | 35 | 9 | 3.5E−05 |
| GO0042773YesEnrich | ATP synthesis coupled electron transport | 10 | 5 | 5.89E−05 |
| GO0022904YesEnrich | respiratory electron transport chain | 9 | 4 | 0.00061 |
| GO0015891YesEnrich | siderophore transport | 5 | 3 | 0.001119 |
| GO0006829YesEnrich | zinc ion transport | 5 | 3 | 0.001119 |
| GO0009597YesEnrich | detection of virus | 12 | 4 | 0.002128 |
| GO0046718YesEnrich | entry of virus into host cell | 12 | 4 | 0.002128 |
| Table 13 - Part 2: Gene Ontology (GO) terms enriched in genes that are down regulated in anaerobic wild-type (WT) when compared to aerobic wild-type (WT) | | | | |
| GO0006826YesEnrich | iron ion transport | 36 | 17 | 2E−12 |
| GO0009060YesEnrich | aerobic respiration | 21 | 16 | 4.86E−12 |
| GO0006099YesEnrich | tricarboxylic acid cycle | 22 | 16 | 6.33E−12 |
| GO0055114YesEnrich | oxidation reduction | 324 | 47 | 2.98E−10 |
| GO0006810YesEnrich | transport | 665 | 74 | 3.67E−10 |
| GO0006811YesEnrich | ion transport | 94 | 23 | 7.18E−10 |
| GO0009061YesEnrich | anaerobic respiration | 35 | 13 | 1.78E−08 |
| GO0022900YesEnrich | electron transport chain | 92 | 17 | 8.89E−06 |
| GO0019464YesEnrich | glycine decarboxylation via glycine cleavage system | 4 | 4 | 9.44E−06 |
| GO0022904YesEnrich | respiratory electron transport chain | 9 | 5 | 5.41E−05 |
| GO0042773YesEnrich | ATP synthesis coupled electron transport | 10 | 5 | 0.000103 |
| GO0019285YesEnrich | glycine betaine biosynthetic process from choline | 3 | 3 | 0.000171 |
| GO0006094YesEnrich | gluconeogenesis | 8 | 4 | 0.000552 |
| GO0006865YesEnrich | amino acid transport | 66 | 11 | 0.000896 |
| GO0015891YesEnrich | siderophore transport | 5 | 3 | 0.001575 |
| GO0015684YesEnrich | ferrous iron transport | 5 | 3 | 0.001575 |
| GO0006565YesEnrich | L-serine catabolic process | 5 | 3 | 0.001575 |
| GO0006829YesEnrich | zinc ion transport | 5 | 3 | 0.001575 |
| GO0045333YesEnrich | cellular respiration | 5 | 3 | 0.001575 |
| GO0009263YesEnrich | deoxyribonucleotide biosynthetic process | 6 | 3 | 0.00302 |
| GO0009186YesEnrich | deoxyribonucleoside diphosphate metabolic process | 2 | 2 | 0.003098 |
| GO0009597YesEnrich | detection of virus | 12 | 4 | 0.00327 |
| GO0046718YesEnrich | entry of virus into host cell | 12 | 4 | 0.00327 |

TABLE 14

Enrichment of regulons within the differentially expressed genes.

| Abbreviation | # in Regulon data | # Diff Exp Data | Enrichment pValue |
|---|---|---|---|
| Table 14 - Part 1: Wild-type aerobic and anaerobic | | | |
| rpoD | 1148 | 258 | 0 |
| narL | 95 | 48 | 0 |
| arcA | 143 | 77 | 0 |
| ihfB | 200 | 69 | 8.63531E−13 |
| ihfA | 200 | 69 | 8.63531E−13 |
| fnr | 250 | 95 | 1.00919E−12 |
| fur | 77 | 42 | 3.22908E−12 |
| gadE | 31 | 21 | 3.45424E−12 |
| fliA | 49 | 34 | 3.6523E−12 |
| flhC | 76 | 47 | 4.0935E−12 |
| flhD | 76 | 47 | 4.0935E−12 |
| rpoS | 132 | 49 | 7.57749E−12 |
| gadX | 21 | 15 | 2.79983E−09 |
| appY | 9 | 9 | 1.81182E−08 |
| fhlA | 29 | 16 | 1.82971E−07 |
| lrp | 57 | 22 | 2.73888E−06 |
| gadW | 8 | 7 | 6.77181E−06 |
| nrdR | 8 | 7 | 6.77181E−06 |

TABLE 14-continued

Enrichment of regulons within the differentially expressed genes.

| Abbreviation | # in Regulon data | # Diff Exp Data | Enrichment pValue |
|---|---|---|---|
| rpoN | 102 | 31 | 1.0113E-05 |
| fis | 89 | 28 | 1.32647E-05 |
| modE | 42 | 17 | 1.81405E-05 |
| leuO | 5 | 5 | 5.07727E-05 |
| narP | 41 | 16 | 5.47495E-05 |
| b2087 | 6 | 5 | 0.000269664 |
| dcuR | 6 | 5 | 0.000269664 |
| iscR | 26 | 11 | 0.000357452 |
| betI | 4 | 4 | 0.000367989 |
| marA | 23 | 10 | 0.000511536 |
| hns | 112 | 28 | 0.001041019 |
| gcvA | 5 | 4 | 0.001636855 |
| zur | 3 | 3 | 0.002663011 |
| ydeO | 3 | 3 | 0.002663011 |
| lldR | 3 | 3 | 0.002663011 |
| pdhR | 12 | 6 | 0.003060986 |
| fruR | 33 | 11 | 0.003574705 |

Table 14 - Part 2: Wild-type E4 aerobic

| Abbreviation | # in Regulon data | # Diff Exp Data | Enrichment pValue |
|---|---|---|---|
| rpoS | 132 | 71 | 3.12428E-12 |
| arcA | 143 | 57 | 4.46854E-12 |
| fur | 77 | 37 | 6.7385E-12 |
| appY | 9 | 9 | 1.56696E-08 |
| gadX | 21 | 14 | 3.13303E-08 |
| gadE | 31 | 16 | 4.93351E-07 |
| rpoD | 1148 | 206 | 6.75894E-07 |
| gadW | 8 | 7 | 6.06153E-06 |
| b2087 | 6 | 6 | 6.34934E-06 |
| hns | 112 | 33 | 7.6898E-06 |
| csiR | 5 | 5 | 4.68422E-05 |
| iscR | 26 | 12 | 5.83984E-05 |
| cysB | 22 | 10 | 0.000288008 |
| crp | 385 | 76 | 0.000310547 |
| leuO | 5 | 4 | 0.001537815 |
| marA | 23 | 9 | 0.00213101 |
| zur | 3 | 3 | 0.002537549 |
| mprA | 3 | 3 | 0.002537549 |
| ydeO | 3 | 3 | 0.002537549 |
| lldR | 3 | 3 | 0.002537549 |
| dcuR | 6 | 4 | 0.004114833 |
| rbsR | 6 | 4 | 0.004114833 |
| oxyR | 17 | 7 | 0.004807659 |

Table 14 - Part 3: E4 aerobic and anaerobic

| Abbreviation | # in Regulon data | # Diff Exp Data | Enrichment pValue |
|---|---|---|---|
| narL | 95 | 28 | 6.73472E-12 |
| fhlA | 29 | 17 | 7.05336E-12 |
| ihfB | 200 | 40 | 1.40028E-11 |
| ihfA | 200 | 40 | 1.40028E-11 |
| fnr | 250 | 45 | 1.89954E-11 |
| rpoD | 1148 | 111 | 1.21473E-08 |
| iscR | 26 | 11 | 1.28164E-07 |
| rstA | 10 | 7 | 3.11218E-07 |
| narP | 41 | 13 | 4.87115E-07 |
| rpoN | 102 | 20 | 2.40414E-06 |
| fur | 77 | 17 | 2.56701E-06 |
| appY | 9 | 6 | 3.63859E-06 |
| cysB | 22 | 8 | 2.72744E-05 |
| leuO | 5 | 4 | 6.62178E-05 |
| ompR | 15 | 6 | 0.000158169 |
| modE | 42 | 10 | 0.000163217 |
| rbsR | 6 | 4 | 0.000189057 |
| nsrR | 16 | 6 | 0.000240161 |
| arcA | 143 | 19 | 0.001015701 |
| treR | 2 | 2 | 0.00375887 |
| cusR | 6 | 3 | 0.003986618 |
| birA | 3 | 2 | 0.0108183 |
| cadC | 3 | 2 | 0.0108183 |

Table 14 - Part 4: Wild-type and E4 anaerobic

| Abbreviation | # in Regulon data | # Diff Exp Data | Enrichment pValue |
|---|---|---|---|
| rpoS | 132 | 55 | 2.61691E-12 |
| fliA | 49 | 37 | 4.87343E-12 |
| flhC | 76 | 35 | 4.9295E-12 |
| flhD | 76 | 35 | 4.9295E-12 |
| hns | 112 | 36 | 1.23884E-11 |
| lrp | 57 | 24 | 5.56361E-11 |
| gadE | 31 | 14 | 2.22865E-07 |
| ihfB | 200 | 42 | 3.43887E-07 |
| ihfA | 200 | 42 | 3.43887E-07 |
| oxyR | 17 | 10 | 5.56749E-07 |
| ompR | 15 | 9 | 1.69221E-06 |
| csiR | 5 | 5 | 7.4944E-06 |
| gadW | 8 | 6 | 1.6644E-05 |
| gadX | 21 | 9 | 5.90837E-05 |
| rpoD | 1148 | 139 | 0.000276692 |
| leuO | 5 | 4 | 0.000368874 |
| fnr | 250 | 40 | 0.000509491 |
| arcA | 143 | 26 | 0.000746665 |
| cadC | 3 | 3 | 0.000847064 |
| rcsA | 19 | 7 | 0.001200234 |
| rcsB | 19 | 7 | 0.001200234 |
| rstA | 10 | 5 | 0.001260007 |
| betI | 4 | 3 | 0.003148945 |
| lrhA | 4 | 3 | 0.003148945 |

TABLE 15

Whole-genome expression and qPCR comparison for selected genes in the ECOM4LA strain.

| Gene Name | Gene Abbreviation | b-number | Affimetrix Fold | qPCR Fold |
|---|---|---|---|---|
| NADH menaquinone oxidoreductase | yieF | b3717 | 2.47 up | 9.5 up |
|  | wrbA | b1004 | 9.1 up | 47.5 up |
| Fumarate reductase | frdABCD | b4150-b4154 | 3.6 up | 110.0 up |
| Succinate dehydrogenase | shdABCD | b0721-b0724 | 25.35 down | 27.8 down |

Example 10

Redox-Coupled Platform Strain for Production of Commodity Chemicals

Figure 13:
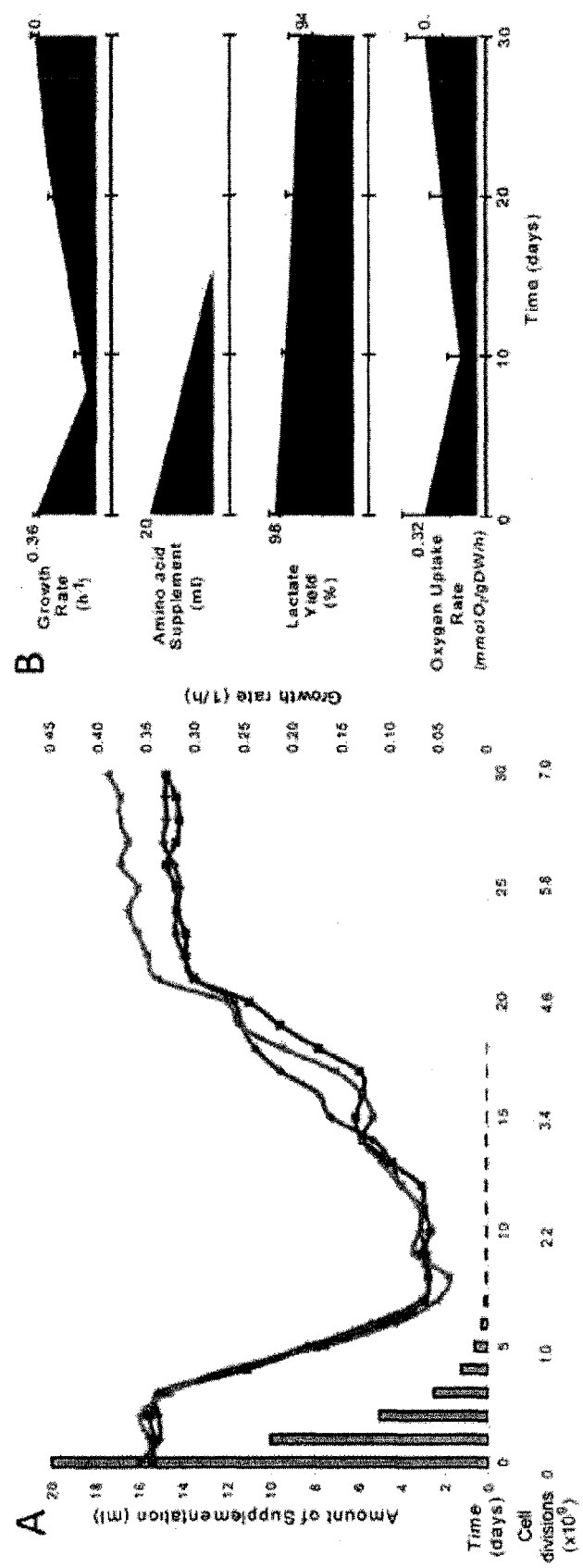
FIG. 13: Phenotypic characteristics of ECOM4 populations during evolution. Growth rate measurements (A) and phenotypic characteristics (B) for three evolved ECOM4 populations are shown as a function of time of evolution. The EZ amino acid supplement amount (in ml) is shown with green bars. The total number of cell divisions for the entire period of adaptation is presented on a secondary abscissa.

The ECOM4 strain developed through the deletion of three cytochrome oxidases (cyd, cyo, cbd) and quinol monooygynase (ygiN) enzymes can be utilized for production of commodity chemicals. Upon deletion of the aforementioned enzymes the resulted strain acquired the ability to produce lactic acid from glucose with nearly 100% efficiency. The inability to use molecular oxygen as an electron acceptor and to utilize electron transport chain to transfer electron away from the NADH forced the strain to rely on lactate dehydrogenase (LdhA) as means of recycling NADH to $NAD^+$ and transferring electrons from pyruvate to lactic acid. The need to oxidize NADH via lactate dehydrogenase couples the flux through this reaction to growth, making this enzyme essential for survival and therefore ensuring the flux through it during the exponential and stationary phase (FIG. 13).

Figure 14:
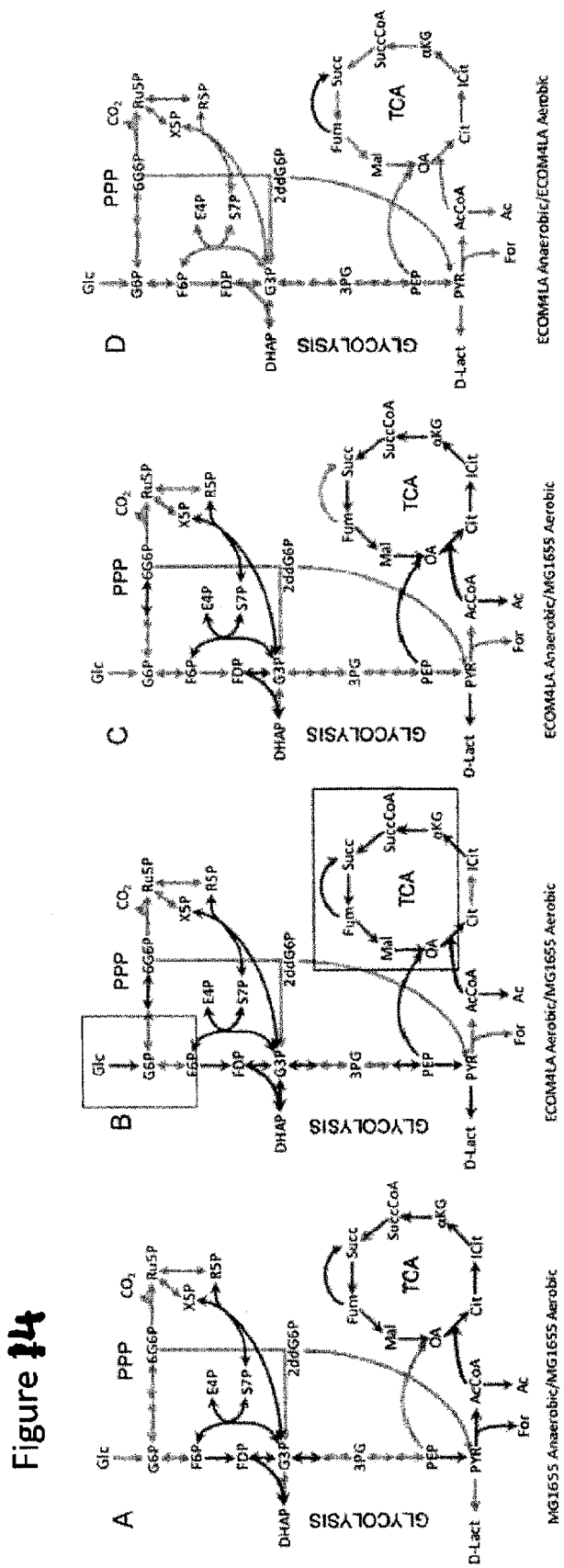
FIG. 14: Transcriptomics analysis of the ECOM4LA and MG1655 strains under oxic and anoxic conditions. Gene expression values of 2 fold and higher (p<0.05) were mapped onto the metabolic map of central metabolism. Red—at least 2-fold upregulation; Green—at least 2-fold downregulation; Yellow—no change. Panels: A—gene expression in anaerobic WT is compared to aerobic WT; B—Aerobic ECOM4LA is compared to aerobic WT; C—anaerobic ECOM4LA is compared to aerobic WT; D—anaerobic ECOM4LA is compared to aerobic ECOM4LA. Boxes in panel B enclose branching areas of metabolism for which relative metabolic flux are illustrated in FIG. 4

Data herein demonstrate the lactate dehydrogenase in ECOM4 strain can be substituted for another heterologus enzyme to ensure production of other chemicals such as: L-lactic acid, L-alanine. The scheme of the use of this invention is depicted in FIG. 14. The lactate production pathway is preferably replaced with either one step conversion of pyruvate to desired product (such as: L-alanine) or multi-step pathway from pyruvate to other product (such as: 2,3-butanediol) as long as the is a NADH dependent reaction (step) to ensure flux through the pathway and recycling of the NADH.

We demonstrate that the flux through the native D-lactate dehydrogenase can be directed towards a heterologus reaction (L-lactate dehydrogenase from the *Lactococcus lactis*) to ensure production of the high-purity racemic (D/L) lactate mixture suitable for polylactic acid (PLA) production (Example 11).

Example 11

Production of the High Purity Racemic Lactic Acid Mixture by Respiratory Deficient *E. coli* Mutant Harboring Heterogeneous L-Lactate Dehydrogenase The microbial production of D-(−)- and L-(+)-lactic acid is rapidly expanding, allowing increased production of polylactic acid (PLA), a renewable, biodegradable plastic. The physical properties of PLA can be adjusted for a specific application by controlling the ratio of L-(+) and D-(−) isomers (1). Production of the racemic lactic acid mixture by an evolved respiratory deficient *E. coli* mutant harboring L-(+)-lactate dehydrogenase from *L. lactis* is reported in this work. Cytochrome oxidases (cydAB, cyoABCD, cbdAB) and quinol monooxygenase (ygiN) were removed from the genome of *E. coli* K-12 MG1655 creating the ECOM4 strain (2). The ECOM4 exhibited reduced oxygen uptake rate by nearly 98%, which led to the activation of the fermentative metabolism under oxic and anoxic conditions. The resulting strain homofermented glucose to D-lactate under an- and aerobic conditions with over 95% yield and an aerobic cell specific production rate of 48.6 mmol/g-dwt/hr, and a volumetric productivity of 1.6 gram/L/hr at even modest cell densities. The ECOM4 mutant was used to harbor L-(+)-lactate dehydrogenase gene (ldh) from *Lactococcus lactis*. The recombinant strain was able to metabolize glucose to D- and L-lactate simultaneously with comparable yields. Previous analysis showed that the native lactate dehydrogenase (ldhA) was upregulated over 5 fold in ECOM4 strain (3). Comparable expression of L-(+)-lactate dehydrogenase gene was ensured by an IPTG inducible promoter. The inducible promoter was used to vary the dosage of ldh gene, and therefore vary the ratio of D-(−) and L-(+) isomers in the final mixture. These results demonstrate that the central metabolism of *E. coli* can be reoriented to the simultaneous production of an indigenous (D-lactate) and nonindegenous (L-lactate) fermentation product.

Figure 18:
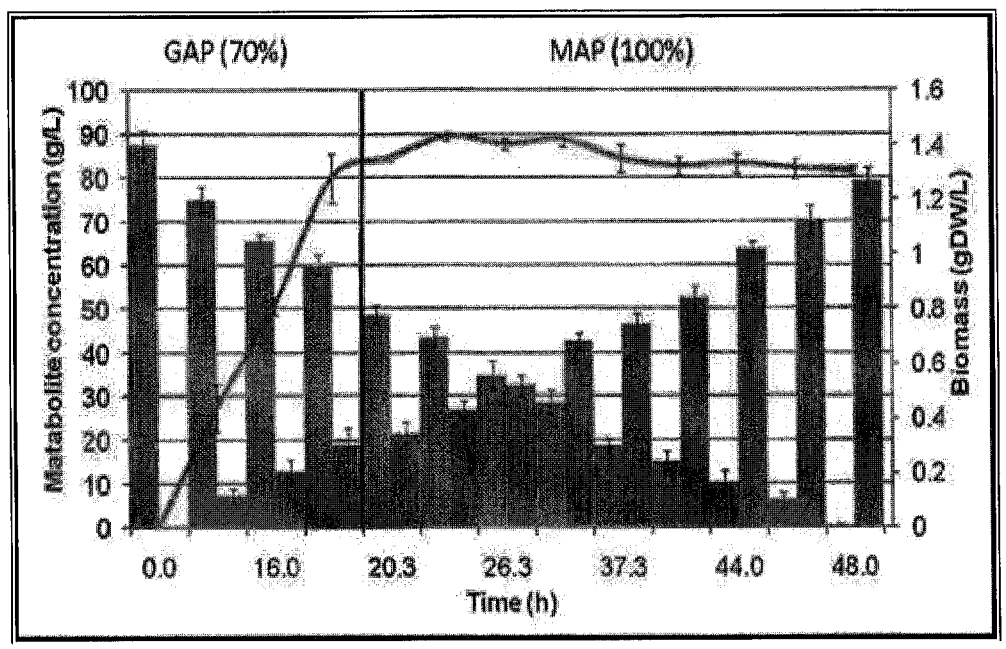
FIG. 18: Batch culture of ECOM4LA strain. During batch fermentation the ECOM4LA strain produced D-lactic acid at 70% efficiency during the growth phase (GAP—Growth Associated Production) and at 100% efficiency during the stationary phase (MAP—Maintenance Associated Production). Blue bars—glucose consumed (gram/L); Red bars—lactate produced (gram/L); Green line—biomass (gDW/L).
Figure 19:
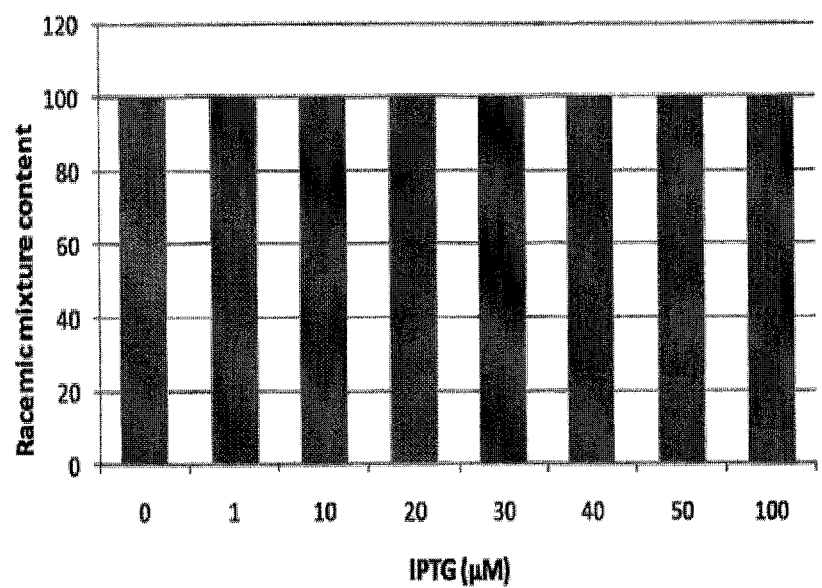
FIG. 19: Composition of racemic mixture depends on the amount of IPTG added. Percentage of (D-) and (L-) lactate produced by ECOM4DL mutant with ldh (L-lactate dehydrogenase) with respect to amount of IPTG added. Bars show total amount of lactate produced, red part—L-lactate; blue part—D-lactate.
Figure 20:
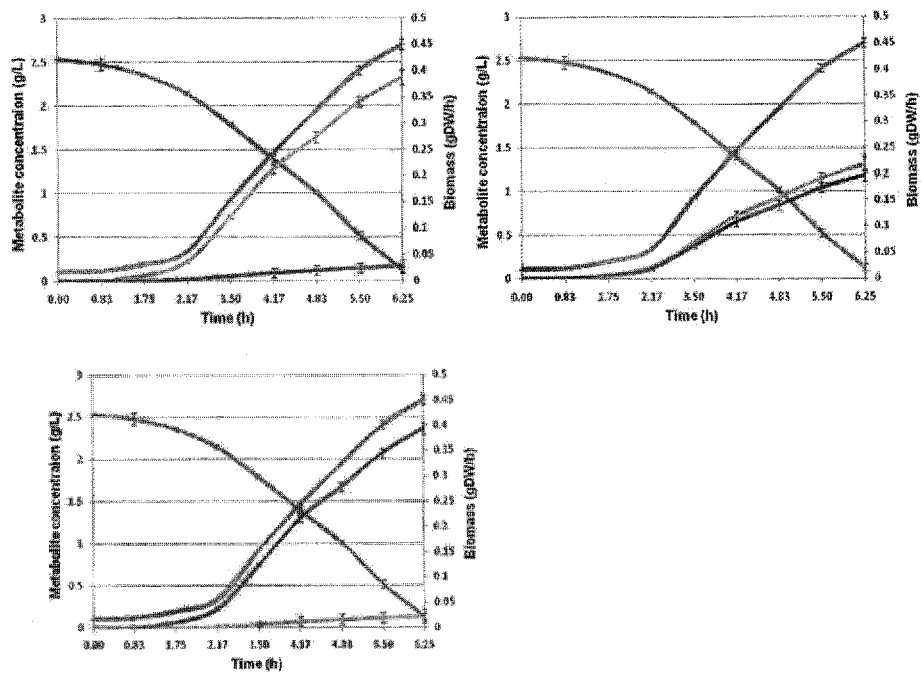
FIG. 20: Growth profile of the ECOM4DL with different level of induction: Aerobic batch with 2.5 g/L glucose in M9 minimal media YE supplemented. Orange—glucose; Green—D-lactate; Red—L-lactate; Blue—Biomass. A: no induction B: 10 μM IPTG induction C: 100 μM IPTG induction.

The ECOM4 strain was further improved to include additional production capabilities. The ECOM4 strain (cydAB-cyoABCDcbdABygiN) was genetically modified to produce a racemic mixture of D (−) and L(+) lactic acid. Originally the ECOM4 strain produced dextrorotatory isomer (D-) of lactic acid as a result of carbohydrate fermentation under both oxic and anoxic growth conditions. The production efficiency was nearly 100% and productivity was between 1.4-1.7 gram/L/h at moderate cell densities. In order to engineer the ECOM4 strain to produce racemic lactate mixture, suitable for PLA production we introduced the L-lactate dehydrogenase (EC: 1.1.1.27) from the *Lactococcus Lactis* bacteria. The L-lactate dehydrogenase was cloned into the pGEX-6-1 vector and introduced into the ECOM4 mutant by electroporation. The resulted strain exhibited dual antibiotic resistance (Amp/Kan) for selection. The recombinant strain was able to metabolize glucose to D- and L-lactate simultaneously with comparable yields. Previous analysis showed that the native lactate dehydrogenase (ldhA) was upregulated over 5 fold in ECOM4 strain. Comparable expression of L-(+)-lactate dehydrogenase gene was ensured by an IPTG inducible promoter. The inducible promoter was used to vary the dosage of ldh gene, and therefore vary the ratio of D-(−) and L-(+) isomers in the final mixture (FIG. 18-20). Production rates for D- and L-isomers were both measured and were on the order of 17-21 mmol/gDW/h for each stereoisomer for a total lactate secretion rate of 34-42 mmol/gDW/h.

Example 12

Production of the High Purity Amino Acid L-Alanine by Respiratory Deficient *E. coli* Mutant Harboring an Additional Copy of L-Alanine Dehydrogenase The ECOM4 strain was further modified to produce L-alanine from glucose. To this end, we introduced an additional copy of the alanine dehydrogenase (dadA) instead of the lactate dehydrogenase (ldhA). The bacterial Alanine dehydrogenase (EC: 1.4.5.-) encoded by dadA was cloned into the pGEX-6-1 plasmid and transformed into ECOM4 strain in the similar fashion as described for the racemic mixture. The new strain was named ECOM4A (ECOM4: alanine producer). The ECOM4A strain produced L-alanine from glucose with the following yield and productivity: 70+/−2.54% and 27.3+/−0.46 mmol/gDW/h respectively. The alanine dehydrogenase was expressed using the similar expression system: pGEX-6p-1 plasmid with the IPTG induction. Low levels of induction (20 μM IPTG) was sufficient to produce enough of alanine dehydrogenase to sustain the elevated glycolytic flux from glucose to pyruvate. We observed trace amounts of pyruvate present in the fermentation broth in mid-log growth phase; however, no pyruvate was detected at the end of fermentation. The growth of the ECOM4A strain during alanine fermentation with 20 μM IPTG induction was 0.18+/−0.08 h-i.

REFERENCES DISCUSSED IN THE ABOVE "BRIEF DESCRIPTION OF THE INVENTION"

1. Portnoy, V. A., Herrgard M. J. Palsson, B, O. 2008. Aerobic Fermentation of D-Glucose by an Evolved Cytochrome Oxidase Deficient *Escherichia coli* Strain. Appl Environ Microbiol, Appl Environ Microbiol. 2008 December; 74(24):7561-9.
2. Cherepanov, P. P., and W. Wackernagel. 1995. Gene disruption in *Escherichia coli*: TcR and KmR cassettes with the option of Flp-catalyzed excision of the antibiotic-resistance determinant. Gene 158:9-14.
3. Datsenko, K. A., and B. L. Wanner. 2000. One-step inactivation of chromosomal genes in *Escherichia coli* K-12 using PCR products. Proc Natl Acad Sci USA 97:6640-6645.
4. Calhoun, M. W., K. L. Oden, R. B. Gennis, M. J. de Mattos, and O. M. Neijssel. 1993. Energetic efficiency of *Escherichia coli*: effects of mutations in components of the aerobic respiratory chain. J Bacteriol 175:3020-3025.
5. Shioi, J., R. C. Tribhuwan, S. T. Berg, and B. L. Taylor. 1988. Signal transduction in chemotaxis to oxygen in *Escherichia coli* and *Salmonella typhimurium*. J Bacteriol 170:5507-5511.
6. Wendisch V F, Bott M, Eikmanns B J. 2006. Metabolic engineering of *Escherichia coli* and *Corynebacterium glutamicum* for biotechnological production of organic acids and amino acids. Curr Opin Microbiol. 9(3):268-74
7. Chang D E, Jung H C, Rhee J S, Pan J G. 1999. Homofermentative production of D- or L-lactate in metabolically engineered *Escherichia coli* RR1. Appl Environ Microbiol. 65(4):1384-9.

8. Zhu Y, Eiteman M A, DeWitt K, Altman E. 2007. Homolactate fermentation by metabolically engineered *Escherichia coli* strains. Appl Environ Microbiol. 73(2):456-64.
9. Hua Q, Joyce A R, Palsson B Ø, Fong S S. 2007. Metabolic characterization of *Escherichia coli* strains adapted to growth on lactate. Appl Environ Microbiol. 73(14):4639-47.
10. Fong, S. S., A. P. Burgard, C. D. Herring, E. M. Knight, F. R. Blattner, C. D. Maranas, and B. O. Palsson. 2005. In silico design and adaptive evolution of *Escherichia coli* for production of lactic acid. Biotechnol Bioeng 91:643-648

REFERENCES DISCUSSED IN EXAMPLES 5-9

1. Adams, M. A., and Z. Jia. 2005. Structural and biochemical evidence for an enzymatic quinone redox cycle in *Escherichia coli*: identification of a novel quinol monooxygenase. J Biol Chem 280:8358-8363.
2. Alexeeva, S., K. J. Hellingwerf, and M. J. Teixeira de Mattos. 2003. Requirement of ArcA for redox regulation in *Escherichia coli* under microaerobic but not anaerobic or aerobic conditions. J Bacteriol 185:204-209.
3. Barrett, T., D. B. Troup, S. E. Wilhite, P. Ledoux, D. Rudnev, C. Evangelista, I. F. Kim, A. Soboleva, M. Tomashevsky, K. A. Marshall, K. H. Phillippy, P. M. Sherman, R. N. Muertter, and R. Edgar. 2009. NCBI GEO: archive for high-throughput functional genomic data. Nucleic Acids Res 37:D885-890.
4. Bekker, M., S. Alexeeva, W. Laan, G. Sawers, J. Teixeira de Mattos, and K. Hellingwerf. The ArcBA two-component system of *Escherichia coli* is regulated by the redox state of both the ubiquinone and the menaquinone pool. J Bacteriol 192:746-754.
5. Bekker, M., G. Kramer, A. F. Hartog, M. J. Wagner, C. G. de Koster, K. J. Hellingwerf, and M. J. de Mattos. 2007. Changes in the redox state and composition of the quinone pool of *Escherichia coli* during aerobic batch-culture growth. Microbiology 153:1974-1980.
6. Brondsted, L., and T. Atlung. 1994. Anaerobic regulation of the hydrogenase 1 (hya) operon of *Escherichia coli*. J Bacteriol 176:5423-5428.
7. Cho, B. K., E. M. Knight, and B. O. Poisson. 2006. PCR-based tandem epitope tagging system for *Escherichia coli* genome engineering. Biotechniques 40:67-72.
8. Compan, I., and D. Touati. 1994. Anaerobic activation of arcA transcription in *Escherichia coli*: roles of Fnr and ArcA. Mol Microbiol 11:955-964.
9. Covert, M. W., E. M. Knight, J. L. Reed, M. J. Herrgard, and B. O. Palsson. 2004. Integrating high-throughput and computational data elucidates bacterial networks. Nature 429:92-96.
10. Datsenko, K. A., and B. L. Wanner. 2000. One-step inactivation of chromosomal genes in *Escherichia coli* K-12 using PCR products. Proc Natl Acad Sci USA 97:6640-6645.
11. Edgar, R., M. Domrachev, and A. E. Lash. 2002. Gene Expression Omnibus: NCBI gene expression and hybridization array data repository. Nucleic Acids Res 30:207-210.
12. Feist, A. M., C. S. Henry, J. L. Reed, M. Krummenacker, A. R. Joyce, P. D. Karp, L. J. Broadbelt, V. Hatzimanikatis, and B. O. Palsson. 2007. A genome-scale metabolic reconstruction for *Escherichia coli* K-12 MG1655 that accounts for 1260 ORFs and thermodynamic information. Mol Syst Biol 3:121.
13. Fischer, E., and U. Sauer. 2003. Metabolic flux profiling of *Escherichia coli* mutants in central carbon metabolism using GC-MS. Eur J Biochem 270:880-891.
14. Fong, S. S., A. P. Burgard, C. D. Herring, E. M. Knight, F. R. Blattner, C. D. Maranas, and B. O. Palsson. 2005. In silico design and adaptive evolution of *Escherichia coli* for production of lactic acid. Biotechnol Bioeng 91:643-648.
15. Gama-Castro, S., V. Jimenez-Jacinto, M. Peralta-Gil, A. Santos-Zavaleta, M. I. Penaloza-Spinola, B. Contreras-Moreira, J. Segura-Salazar, L. Muniz-Rascado, I. Martinez-Flores, H. Salgado, C. Bonavides-Martinez, C. Abreu-Goodger, C. Rodriguez-Penagos, J. Miranda-Rios, E. Morett, E. Merino, A. M. Huerta, L. Trevino-Quintanilla, and J. Collado-Vides. 2008. RegulonDB (version 6.0): gene regulation model of *Escherichia coli* K-12 beyond transcription, active (experimental) annotated promoters and Textpresso navigation. Nucleic Acids Res 36:D120-124.
16. Georgellis, D., O. Kwon, and E. C. Lin. 2001. Quinones as the redox signal for the arc two-component system of bacteria. Science 292:2314-2316.
17. Gunsalus, R. P., and S. J. Park. 1994. Aerobic-anaerobic gene regulation in *Escherichia coli*: control by the ArcAB and Fnr regulons. Res Microbiol 145:437-50.
18. Herring, C. D., A. Raghunathan, C. Honisch, T. Patel, M. K. Applebee, A. R. Joyce, T. J. Albert, F. R. Blattner, D. van den Boom, C. R. Cantor, and B. O. Palsson. 2006. Comparative genome sequencing of *Escherichia coli* allows observation of bacterial evolution on a laboratory timescale. Nat Genet. 38:1406-1412.
19. Iuchi, S., and E. C. Lin. 1993. Adaptation of *Escherichia coli* to redox environments by gene expression. Mol Microbiol 9:9-15.
20. Iuchi, S., and E. C. Lin. 1988. arcA (dye), a global regulatory gene in *Escherichia coli* mediating repression of enzymes in aerobic pathways. Proc Natl Acad Sci USA 85:1888-1892.
21. Iverson, T. M., C. Luna-Chavez, G. Cecchini, and D. C. Rees. 1999. Structure of the *Escherichia coli* fumarate reductase respiratory complex. Science 284:1961-1966.
22. Jervis, A. J., J. C. Crack, G. White, P. J. Artymiuk, M. R. Cheesman, A. J. Thomson, N. E. Le Brun, and J. Green. 2009. The $O_2$ sensitivity of the transcription factor FNR is controlled by Ser24 modulating the kinetics of [4Fe-4S] to [2Fe-2S] conversion. Proc Natl Acad Sci USA 106:4659-4664.
23. Kanehisa, M., S. Goto, M. Furumichi, M. Tanabe, and M. Hirakawa. KEGG for representation and analysis of molecular networks involving diseases and drugs. Nucleic Acids Res 38:D355-360.
24. Kang, Y., K. D. Weber, Y. Qiu, P. J. Kiley, and F. R. Blattner. 2005. Genomewide expression analysis indicates that FNR of *Escherichia coli* K-12 regulates a large number of genes of unknown function. J Bacteriol 187:1135-1160.
25. Karp, P. D., I. M. Keseler, A. Shearer, M. Latendresse, M. Krummenacker, S. M. Paley, I. Paulsen, J. Collado-Vides, S. Gama-Castro, M. Peralta-Gil, A. Santos-Zavaleta, M. I. Penaloza-Spinola, C. Bonavides-Martinez, and J. Ingraham. 2007. Multidimensional annotation of the *Escherichia coli* K-12 genome. Nucleic Acids Res 35:7577-7590.
26. Keseler, I. M., C. Bonavides-Martinez, J. Collado-Vides, S. Gama-Castro, R. P. Gunsalus, D. A. Johnson, M. Krummenacker, L. M. Nolan, S. Paley, I. T. Paulsen, M. Peralta-Gil, A. Santos-Zavaleta, A. G. Shearer, and P. D. Karp. 2009. EcoCyc: a comprehensive view of *Escherichia coli* biology. Nucleic Acids Res 37:D464-470.

27. Lee, K. H., J. H. Park, T. Y. Kim, H. U. Kim, and S. Y. Lee. 2007. Systems metabolic engineering of *Escherichia coli* for L-threonine production. Mol Syst Biol 3:149.
28. Lee, S. J., D. Y. Lee, T. Y. Kim, B. H. Kim, J. Lee, and S. Y. Lee. 2005. Metabolic engineering of *Escherichia coli* for enhanced production of succinic acid, based on genome comparison and in silico gene knockout simulation. Appl Environ Microbiol 71:7880-7887.
29. Lynch, A. S., and E. C. Lin. 1996. Transcriptional control mediated by the ArcA two-component response regulator protein of *Escherichia coli*: characterization of DNA binding at target promoters. J Bacteriol 178:6238-6249.
30. Murray, E. L., and T. Conway. 2005. Multiple regulators control expression of the Entner-Doudoroff aldolase (Eda) of *Escherichia coli*. J Bacteriol 187:991-1000.
31. Nanchen, A., T. Fuhrer, and U. Sauer. 2007. Determination of metabolic flux ratios from 13C-experiments and gas chromatography-mass spectrometry data: protocol and principles. Methods Mol Biol 358:177-197.
32. Neidhardt, F. (ed.). 1996. *Escherichia coli* and *Salmonella*, Second Edition ed, vol. 1. ASM Press Washington, D.C.
33. Portnoy, V. A., M. J. Herrgard, and B. O. Palsson. 2008. Aerobic fermentation of D-glucose by an evolved cytochrome oxidase-deficient *Escherichia coli* strain. Appl Environ Microbiol 74:7561-7569.
34. Salmon, K., S. P. Hung, K. Mekjian, P. Baldi, G. W. Hatfield, and R. P. Gunsalus. 2003. Global gene expression profiling in *Escherichia coli* K12. The effects of oxygen availability and FNR. J Biol Chem 278:29837-29855.
35. Scott, C., J. D. Partridge, J. R. Stephenson, and J. Green. 2003. DNA target sequence and FNR-dependent gene expression. FEBS Lett 541:97-101.
36. Shestopalov, A. I., A. V. Bogachev, R. A. Murtazina, M. B. Viryasov, and V. P. Skulachev. 1997. Aeration-dependent changes in composition of the quinone pool in *Escherichia coli*. Evidence of post-transcriptional regulation of the quinone biosynthesis. FEBS Lett 404:272-274.
37. Spiro, S., and J. R. Guest. 1991. Adaptive responses to oxygen limitation in *Escherichia coli*. Trends Biochem Sci 16:310-314.
38. Spiro, S., and J. R. Guest. 1990. FNR and its role in oxygen-regulated gene expression in *Escherichia coli*. FEMS Microbiol Rev 6:399-428.
39. Storey, J. D., and R. Tibshirani. 2003. Statistical significance for genomewide studies. Proc Natl Acad Sci USA 100:9440-9445.
40. Sutton, V. R., E. L. Mettert, H. Beinert, and P. J. Kiley. 2004. Kinetic analysis of the oxidative conversion of the [4Fe-4S]2+ cluster of FNR to a [2Fe-2S]2+ Cluster. J Bacteriol 186:8018-8025.
41. Szyperski, T. 1995. Biosynthetically directed fractional 13C-labeling of proteinogenic amino acids. An efficient analytical tool to investigate intermediary metabolism. Eur J Biochem 232:433-448.
42. van Winden, W. A., C. Wittmann, E. Heinzle, and J. J. Heijnen. 2002. Correcting mass isotopomer distributions for naturally occurring isotopes. Biotechnol Bioeng 80:477-479.
43. Yagi, T., and A. Matsuno-Yagi. 2003. The proton-translocating NADH-quinone oxidoreductase in the respiratory chain: the secret unlocked. Biochemistry 42:2266-2274.

REFERENCES DISCUSSED IN EXAMPLES 1-4

1. Adams, M. A., and Z. Jia. 2005. Structural and biochemical evidence for an enzymatic quinone redox cycle in *Escherichia coli*: identification of a novel quinol monooxygenase. J Biol Chem 280:8358-8363.
2. Becker, S. A., A. M. Feist, M. L. Mo, G. Hannum, B. O. Palsson, and M. J. Herrgard. 2007. Quantitative prediction of cellular metabolism with constraint-based models: the COBRA Toolbox. Nat. Protoc 2:727-738.
3. Bekker, M., G. Kramer, A. F. Hartog, M. J. Wagner, C. G. de Koster, K. J. Hellingwerf, and M. J. de Mattos. 2007. Changes in the redox state and composition of the quinone pool of *Escherichia coli* during aerobic batch-culture growth. Microbiology 153:1974-1980.
4. Bell, S. L., and B. O. Palsson. 2004. Phenotype phase plane analysis using interior point methods. Computers & Chemical Engineering 29:481-486.
5. Calhoun, M. W., K. L. Oden, R. B. Gennis, M. J. de Mattos, and O. M. Neijssel. 1993. Energetic efficiency of *Escherichia coli*: effects of mutations in components of the aerobic respiratory chain. J Bacteriol 175:3020-3025.
6. Cherepanov, P. P., and W. Wackernagel. 1995. Gene disruption in *Escherichia coli*: TcR and KmR cassettes with the option of Flp-catalyzed excision of the antibiotic-resistance determinant. Gene 158:9-14.
7. Covert, M. W., E. M. Knight, J. L. Reed, M. J. Herrgard, and B. O. Palsson. 2004. Integrating high-throughput and computational data elucidates bacterial networks. Nature 429:92-96.
8. Dassa, J., H. Fsihi, C. Marck, M. Dion, M. Kieffer-Bontemps, and P. L. Boquet. 1991. A new oxygen-regulated operon in *Escherichia coli* comprises the genes for a putative third cytochrome oxidase and for pH 2.5 acid phosphatase (appA). Mol Gen Genet. 229:341-352.
9. Datsenko, K. A., and B. L. Wanner. 2000. One-step inactivation of chromosomal genes in *Escherichia coli* K-12 using PCR products. Proc Natl Acad Sci USA 97:6640-6645.
10. Edwards, J. S., R. U. Ibarra, and B. O. Palsson. 2001. In silico predictions of *Escherichia coli* metabolic capabilities are consistent with experimental data. Nat Biotechnol 19:125-130.
11. Edwards, J. S., and B. O. Palsson. 2000. Metabolic flux balance analysis and the in silico analysis of *Escherichia coli* K-12 gene deletions. BMC Bioinformatics 1:1.
12. Edwards, J. S., and B. O. Palsson. 2000. Robustness analysis of the *Escherichia coli* metabolic network. Biotechnol Prog 16:927-939.
13. Feist, A. M., C. S. Henry, J. L. Reed, M. Krummenacker, A. R. Joyce, P. D. Karp, L. J. Broadbelt, V. Hatzimanikatis, and B. O. Palsson. 2007. A genome-scale metabolic reconstruction for *Escherichia coli* K-12 MG1655 that accounts for 1260 ORFs and thermodynamic information. Mol Syst Biol 3:121.
14. Feist, A. M., and B. O. Palsson. 2008. The growing scope of applications of genome-scale metabolic reconstructions using *Escherichia coli*. Nat Biotechnol 26:659-667.
15. Fischer, E., and U. Sauer. 2003. Metabolic flux profiling of *Escherichia coli* mutants in central carbon metabolism using GC-MS. Eur J Biochem 270:880-891.
16. Fong, S. S., A. P. Burgard, C. D. Herring, E. M. Knight, F. R. Blattner, C. D. Maranas, and B. O. Palsson. 2005. In silico design and adaptive evolution of *Escherichia coli* for production of lactic acid. Biotechnol Bioeng 91:643-648.
17. Fong, S. S., A. Nanchen, B. O. Palsson, and U. Sauer. 2006. Latent pathway activation and increased pathway capacity enable *Escherichia coli* adaptation to loss of key metabolic enzymes. J Biol Chem 281:8024-8033.
18. Jaworowski, A., H. D. Campbell, M. I. Poulis, and I. G. Young. 1981. Genetic Identification and Purification of the Respiratory NADH Dehydrogenase of *Escherichia coli*. Biochemistry 20:2041-2047.
19. Kita, K., K. Konishi, and Y. Anraku. 1984. Terminal oxidases of *Escherichia coli* aerobic respiratory chain. II. Purification and properties of cytochrome b558-d complex from cells grown with limited oxygen and evidence of branched electron-carrying systems. J Biol Chem 259: 3375-3381.
20. Lee, K. H., J. H. Park, T. Y. Kim, H. U. Kim, and S. Y. Lee. 2007. Systems metabolic engineering of *Escherichia coli* for L-threonine production. Mol Syst Biol 3:149.
21. Lee, S. J., D. Y. Lee, T. Y. Kim, B. H. Kim, J. Lee, and S. Y. Lee. 2005. Metabolic engineering of *Escherichia coli* for enhanced production of succinic acid, based on genome comparison and in silico gene knockout simulation. Appl Environ Microbiol 71:7880-7887.
22. Neidhardt, F. (ed.). 1996. *Escherichia coli* and *Salmonella*, Second Edition ed, vol. 1. ASM Press Washington, D.C.
23. Neidhardt, F. C., P. L. Bloch, and D. F. Smith. 1974. Culture medium for enterobacteria. J Bacteriol 119:736-747.
24. Newton, G., and R. B. Gennis. 1991. In vivo assembly of the cytochrome d terminal oxidase complex of *Escherichia coli* from genes encoding the two subunits expressed on separate plasmids. Biochim Biophys Acta 1089:8-12.
25. Puustinen, A., M. Finel, T. Haltia, R. B. Gennis, and M. Wikstrom. 1991. Properties of the two terminal oxidases of *Escherichia coli*. Biochemistry 30:3936-3942.
26. Sambrook, J., and D. W. Russell. 2001. Molecular Cloning: A Laboratory Manual 3ed, vol. A2.2. Cold Spring Harbor Laboratory Press, New York.
27. Schilling, C. H., J. S. Edwards, D. Letscher, and B. O. Palsson. 2000. Combining pathway analysis with flux balance analysis for the comprehensive study of metabolic systems. Biotechnol Bioeng 71:286-306.
28. Shioi, J., R. C. Tribhuwan, S. T. Berg, and B. L. Taylor. 1988. Signal transduction in chemotaxis to oxygen in *Escherichia coli* and *Salmonella typhimurium*. J Bacteriol 170:5507-5511.
29. Sturr, M. G., T. A. Krulwich, and D. B. Hicks. 1996. Purification of a cytochrome bd terminal oxidase encoded by the *Escherichia coli* app locus from a delta cyo delta cyd strain complemented by genes from *Bacillus firmus* OF4. J Bacteriol 178:1742-1749.

REFERENCES CITED IN THE ABOVE "SUPPLEMENTARY MATERIALS TO EXAMPLES 1-4"

1. Conradt, H., M. Hohmann-Berger, H. P. Hohmann, H. P. Blaschkowski, and J. Knappe. 1984. Pyruvate formate-lyase (inactive form) and pyruvate formate-lyase activating enzyme of *Escherichia coli*: isolation and structural properties. Arch Biochem Biophys 228:133-42.
2. Fong, S. S., A. P. Burgard, C. D. Herring, E. M. Knight, F. R. Blattner, C. D. Maranas, and B. O. Palsson. 2005. In silico design and adaptive evolution of *Escherichia coli* for production of lactic acid. Biotechnol Bioeng 91:643-648.
3. Joyce, A. R., J. L. Reed, A. White, R. Edwards, A. Osterman, T. Baba, H. Mori, S. A. Lesely, B. O. Palsson, and S. Agarwalla. 2006. Experimental and computational assessment of conditionally essential genes in *Escherichia coli*. J Bacteriol 188:8259-71.
4. Knappe, J., and G. Sawers. 1990. A radical-chemical route to acetyl-CoA: the anaerobically induced pyruvate formate-lyase system of *Escherichia coli*. FEMS Microbiol Rev 6:383-98.
5. Rasmussen, L. J., P. L. Moller, and T. Atlung. 1991. Carbon metabolism regulates expression of the pfl (pyruvate formate-lyase) gene in *Escherichia coli*. J Bacteriol 173:6390-7.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. A transgenic *Escherichia coli* cell comprising an additional copy of *Escherichia coli* alanine dehydrogenase (DadA) gene, and a deletion in the endogenous cydA gene (SEQ ID NO: 1), cydB gene (SEQ ID NO: 2), cyoA gene (SEQ ID NO: 3), cyoB gene (SEQ ID NO: 4), cyoC gene (SEQ ID NO: 5), cyoD gene (SEQ ID NO: 6), cbdA gene (SEQ ID NO: 7), cbdB gene (SEQ ID NO: 8), ygiN gene (SEQ ID NO: 9), and ldhA gene, wherein said transgenic *Escherichia coli* cell
   a) has substantially the same level of growth in oxic conditions as the level of growth in anoxic conditions of the corresponding *Escherichia coli* cell that has no deletion of the endogenous cydA gene, endogenous cydB gene, endogenous cyoA gene, endogenous cyoB gene, endogenous cyoC gene, endogenous cyoD gene, endogenous cbdA gene, endogenous cbdB gene, and endogenous ygiN gene,
   b) is capable of converting glucose to D-lactate under oxic conditions and/or anoxic conditions,
   c) has substantially the same level of growth as said corresponding *Escherichia coli* in M9 minimal essential media that
      (i) comprises a carbon source consisting of glucose, and
      (ii) lacks amino acids Ala, Arg, Asn, Asp, Cys, Glu, Gln, Gly, His, Ile, Leu, Lys, Met, Phe, Pro, Ser, Thr, Trp, Tyr, and Val, and
   d) is capable of producing an increased level of alanine compared to the corresponding *Escherichia coli* cell that comprises the endogenous ldhA gene and that does not comprise a heterologous DNA sequence encoding DadA.

2. The transgenic *Escherichia coli* cell of claim 1, wherein said transgenic cell has reduced oxygen uptake in oxic conditions compared to said corresponding *Escherichia coli*.

3. The transgenic *Escherichia coli* cell of claim 1, wherein said transgenic cell produces increased levels of D-lactic acid, when cultured in the presence of glucose as substrate, under oxic conditions and/or anoxic conditions compared to D-lactic acid levels produced by said corresponding *Escherichia coli*.

4. The transgenic *Escherichia coli* cell of claim 1, wherein said transgenic cell produces altered levels of acetate, when cultured in the presence of glucose as substrate, under oxic conditions and/or anoxic conditions compared to acetate levels produced by said corresponding *Escherichia coli*.

5. The transgenic *Escherichia coli* cell of claim 1, wherein said transgenic cell has increased expression of at least one of endogenous sodA gene (SEQ ID NO:10), and endogenous sodB gene (SEQ ID NO:11) compared to said corresponding *Escherichia coli*.

6. The transgenic *Escherichia coli* cell of claim 1, wherein said transgenic cell further comprises a deletion of at least one of endogenous sodA gene (SEQ ID NO:10) and endogenous sodB gene (SEQ ID NO:11).

7. A method for producing a transgenic *Escherichia coli* cell comprising
   a) introducing an additional copy of *Escherichia coli* alanine dehydrogenase (DadA) gene into an *Escherichia coli* cell,
   b) deleting the endogenous cydA gene (SEQ ID NO: 1), cydB gene (SEQ ID NO: 2), cyoA gene (SEQ ID NO: 3), cyoB gene (SEQ ID NO: 4), cyoC gene (SEQ ID NO: 5), cyoD gene (SEQ ID NO: 6), cbdA gene (SEQ ID NO: 7), cbdB gene (SEQ ID NO: 8), ygiN gene (SEQ ID NO: 9), and ldhA gene from the genome of said *Escherichia coli* cell to produce a transgenic *Escherichia coli* cell, and
   c) culturing said transgenic *Escherichia coli* cell to produce a cultured *Escherichia coli* cell, wherein said culturing is in M9 minimal media that
      i) comprises a carbon source consisting of glucose, and
      ii) lacks amino acids Ala, Arg, Asn, Asp, Cys, Glu, Gln, Gly, His, Ile, Leu, Lys, Met, Phe, Pro, Ser, Thr, Trp, Tyr, and Val.

8. The method of claim 7, further comprising purifying said cultured *Escherichia coli* cell.

9. A method for producing an amino acid comprising culturing the transgenic *Escherichia coli* cell of claim 1 in M9 minimal essential medium that contains glucose, wherein said culturing is under conditions for production of an amino acid.

10. A method for producing 2,3-butanediol (2,3-BDO) comprising culturing the transgenic *Escherichia coli* cell of claim 1 in M9 minimal essential medium that contains glucose, wherein said culturing is under conditions for production of 2,3-BDO.

* * * * *